US005502040A

United States Patent [19]

O'Doherty

[11] Patent Number: 5,502,040
[45] Date of Patent: Mar. 26, 1996

[54] ANTICOCCIDIAL METHOD

[75] Inventor: George O. P. O'Doherty, Greenfield, Ind.

[73] Assignee: Eli Lilly and Company, Indianapolis, Ind.

[21] Appl. No.: 230,959

[22] Filed: Apr. 21, 1994

Related U.S. Application Data

[62] Division of Ser. No. 37,800, Mar. 26, 1993, Pat. No. 5,331,003.
[51] Int. Cl.[6] .......................... A61K 31/70; A61K 31/415
[52] U.S. Cl. .............................. 514/27; 514/394; 514/395
[58] Field of Search ............................ 514/27, 394, 395

[56] References Cited

U.S. PATENT DOCUMENTS

| 3,655,901 | 7/1972 | Jensen et al. | 514/388 |
|---|---|---|---|
| 3,705,238 | 12/1972 | Hamill et al. | 424/121 |
| 3,900,784 | 9/1976 | Peterson | 514/394 |
| 4,109,004 | 8/1978 | Percival | 514/395 |
| 4,407,946 | 10/1983 | Labeda et al. | 435/75 |
| 4,683,204 | 7/1987 | Boeck | 435/128 |
| 4,992,423 | 2/1991 | Cullen et al. | 514/27 |

OTHER PUBLICATIONS

*The Biology of the Coccidia*, (Peter L. Long ed., University Park Press 1982) Chapter 9, pp. 373–427.
Jeffers, T. K. Coccidia and intestinal coccidiomorphs, Vth International Coccidiosis Conference, Tours (France), 17–20 Oct. 1989. Ed. INRA Publ., 1989 (Les Colloques de l'INRA, No. 49), pp. 295–308. Anticoccidial drug resistance: a review with emphasis on the polyether ionophores.

Preston, P. N., *Chem. Heterocycl. Compd.*, 40 #1 (1981), pp. 1–285.

Joshi, K. C., et al., *J. Fluorine Chem.*, 56 #1 (1992), pp. 1–27.

Sharma, S., et al., *Prog. Drug Res.*, 27 (1983), pp. 85–161.

Preston, P. N., *Chem. Rev.*, 74 #3 (1974), pp. 279–314.

*Primary Examiner*—Marianne M. Cintins
*Assistant Examiner*—Kevin E. Weddington
*Attorney, Agent, or Firm*—Kathleen R. S. Page

[57] ABSTRACT

The present invention is directed to anticoccidial methods, animal feed premixes, and animal feeds, employing a specified o-phenylenediamine or benzimidazole. The present invention is also directed to anticoccidial methods, animal feed premixes, and animal feeds employing two active agents. In such combined therapy, a first substance is a polyether antibiotic, and the second substance is a designated o-phenylenediamine, benzimidazole, or benzimidazoline.

10 Claims, No Drawings

ANTICOCCIDIAL METHOD

This application is a division of application Ser. No. 08/037,800, filed Mar. 26, 1993, now U.S. Pat. No. 5,331,003.

BRIEF SUMMARY OF THE INVENTION

Coccidiosis is a protozoan disease of fowl and other animals. Uncontrolled, it is a devastating disease. Chemotherapeutics are known, such as the polyethers monensin and narasin, sold under the trademarks Coban® and Monteban®, respectively. However, there are various problems. Some chemotherapeutics cause undesirable side effects. Others, especially if used recurringly in a facility, lead to the development of reduced sensitivity or resistance to a particular chemotherapeutic or entire class of chemotherapeutics. For this reason, combinations are employed, such as the combination of narasin and nicarbazin, sold under the trademark Maxiban®. Also, "rotation" and "shuttle" regimens are used, in which different anticoccidial regimens are employed from one growout to the next, and during a growout. However, even with all of these available techniques, there is still a continuing need to discover new chemotherapeutic techniques for the control of coccidiosis.

It has now been discovered that certain phenylenediamines and benzimidazoles, more fully defined below, are efficacious against coccidiosis. These compounds can be employed to treat and/or prevent coccidiosis in fowl. They may be employed alone or, in a preferred embodiment, they are employed in combination with a polyether. In an especially preferred embodiment, the present combination therapy is used to prevent or treat coccidiosis attributable to a polyether-insensitive strain of Eimeria. The topic of drug insensitivity is well reviewed in Jeffers, T. K. Coccidia and intestinal coccidiomorphs, Vth International Coccidiosis Conference, Tours (France), 17–20 Oct. 1989. Ed. INRA Publ., 1989 (Les Colloques de l'INRA, no. 49), pages 295–308. Anticoccidial drug resistance: a review with emphasis on the polyether ionophores.

DETAILED DESCRIPTION OF THE INVENTION

The present invention is directed to a method of preventing or treating coccidiosis in a fowl which comprises administering to the fowl an effective amount of an active agent selected from compounds of the formulae

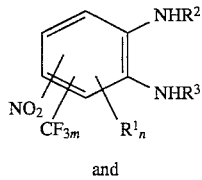

I

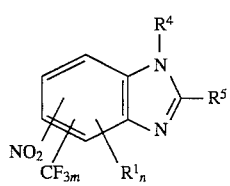

II wherein $R^1$ represents bromo or chloro, m represents an integer of 0 or 1 and n represents an integer of from 0 to 3, with the sum of m and n being an integer of from 1 to 3;

$R^2$ represents difluoroacetyl, chlorodifluoroacetyl, 2,2,3,3-tetrafluoropropionyl, or a perfluoroalkanoyl of from $C_2$ to $C_4$;

$R^3$ represents H, trichloroacetyl, or an independently selected $R^2$;

$R^4$ represents H, OH, $OCH_3$, or a group hydrolyzable to a foregoing $R^4$ moiety; and $R^5$ represents difluoromethyl, chlorodifluoromethyl, 1,1,2,2-tetrafluoroethyl, or a perfluoroalkyl of $C_1$–$C_3$;

or a physiologically acceptable salt of a Formula II compound.

The present invention is also directed to animal feed premixes and final animal feeds comprising an active agent as defined above.

Further, the invention is directed to anticoccidial methods comprising administering both an active agent as defined above, or a benzimidazoline as defined below, as well as a polyether antibiotic. Animal feed premixes and final animal feeds comprising both (1) a phenylenediamine, benzimidazole, or benzimidazoline, and (2) a polyether, are another aspect of the present invention. This combined therapy has unexpectedly been found to provide excellent control of coccidiosis attributable to polyether-insensitive strains.

The benzimidazoline compounds to be employed in this embodiment are of the formula

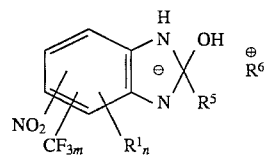

III wherein $R^1$, m, n, and $R^5$ have the same meanings set forth above; and $R^6$ represents sodium, potassium, lithium, silver, calcium, ammonium, or substituted ammonium derived from an organic amine which is as basic as, or more basic than, ammonia.

The compounds of Formula I, II, and III, are prepared in known procedures, and a large number of specific compounds are taught in the literature. The following U.S. patents Formula I: U.S. Pat. No. 3,557,211
U.S. Pat. No. 3,907,892
U.S. Pat. No. 3,989,840

Formula II: U.S. Pat. No. 3,980,784

Formula III: U.S. Pat. No. 4,265,901 teach the synthesis of many of the compounds to be employed in the present invention, and are hereby incorporated by reference. Several review articles exist and further illustrate the synthesis of compounds to be employed in the present invention:

Chem. Heterocycl. Compd. 40, #1 (1981), pages 1–285

J. Fluoro. Chem, 56, #1 (1992), pages 1–27

Prog. Drug Res. 27 (1983), pages 85–161

Chem. Rev. 74, #3 (1974), pages 279–314.

These also are hereby incorporated by reference.

Compounds of Formula I which can be employed in the present invention include the following:

| Example # | Name |
|---|---|
| 1 | 3-nitro-5-(trifluoromethyl)-$N^1$-(difluoroacetyl)-o-phenylenediamine |
| 2 | 3-nitro-5-chloro-$N^1,N^2$-bis(2,2,3,3-tetrafluoropropionyl)-o-phenylenediamine |
| 3 | 3-nitro-5-chloro-$N^1$-(2,2,3,3-tetrafluoropropionyl)-o-phenylenediamine |
| 4 | 3-nitro-5-(trifluoromethyl)-$N^1,N^2$-bis(2,2,3,3-tetrafluoropropionyl)-o-phenylenediamine |
| 5 | 3-nitro-5-(trifluoromethyl)-$N^1$-(2,2,3,3-tetrafluoropropionyl)-o-phenylenediamine |
| 6 | 3-nitro-5-(trifluoromethyl)-$N^1$-(2-(trifluoromethyl)-2,3,3,3-tetrafluoropropionyl)-o-phenylenediamine |
| 7 | 3-nitro-5-(trifluoromethyl)-$N^1,N^2$-bis(2-(trifluoromethyl)-2,3,3,3-tetrafluoropropionyl)-o-phenylenediamine |
| 8 | 5-nitro-3-(trifluoromethyl)-$N^1$-(perfluoropropionyl)-o-phenylenediamine |
| 9 | 3-nitro-5-(trifluoromethyl)-$N^1$-(perfluoro-n-butyryl)-o-phenylenediamine |
| 10 | 5-nitro-3-(trifluoromethyl)-$N^1$-(trifluoroacetyl)-o-phenylenediamine |
| 11 | 3-nitro-5-chloro-$N^1,N^2$-bis(trifluoroacetyl)-o-phenylenediamine |
| 12 | 3-nitro-5-(trifluoromethyl)-$N^1,N^2$-bis(trifluoroacetyl)-o-phenylenediamine |
| 13 | 3-nitro-5-chloro-$N^1$-(trifluoroacetyl)-o-phenylenediamine |
| 14 | 3-nitro-5-(trifluoromethyl)-$N^1$-(perfluoropropionyl)-o-phenylenediamine |
| 15 | 3-nitro-5-(trifluoromethyl)-$N^1$-(perfluoropropionyl)-$N^2$-(trifluoroacetyl)-o-phenylenediamine |
| 16 | 3-nitro-5-(trifluoromethyl)-$N^1$-(trifluoroacetyl)-o-phenylenediamine |
| 17 | 5-nitro-3-(trifluoromethyl)-$N^1$-(1,1,2,2-tetrafluoropropionyl)-o-phenylenediamine |
| 18 | 6-nitro-4-(trifluoromethyl)-$N^1$-(trifluoroacetyl)-$N^2$-(trichloroacetyl)-o-phenylenediamine |
| 19 | 6-nitro-4-(trifluoromethyl)-$N^1$-(perfluoropropionyl)-$N^2$-(trichloroacetyl)-o-phenylenediamine |
| 20 | 3-nitro-5-(trifluoromethyl)-$N^1$-(perfluoropropionyl)-$N^2$-(trichloroacetyl)-o-phenylenediamine |

Compounds of Formula II which can be employed in the present invention include the following:

| Example # | Name |
|---|---|
| 21 | 5-nitro-2,6-bis(trifluoromethyl)benzimidazole |
| 22 | 4-nitro-6-(trifluoromethyl)-2-(perfluoroethyl)benzimidazole |
| 23 | 4-nitro-2,6-bis(trifluoromethyl)benzimidazole |
| 24 | 6-nitro-5-chloro-2-(trifluoromethyl)benzimidazole |
| 25 | 4-nitro-6-chloro-2-(trifluoromethyl)benzimidazole |
| 26 | 4-nitro-6-(trifluoromethyl)-2-(difluoromethyl)benzimidazole |
| 27 | 5-nitro-4-chloro-2-(trifluoromethyl)benzimidazole |
| 28 | 7-nitro-4-chloro-2-(trifluoromethyl)benzimidazole |
| 29 | 4-nitro-2,6-bis(trifluoromethyl)benzimidazole sodium salt |
| 30 | 6-nitro-4-chloro-2-(trifluoromethyl)benzimidazole |
| 31 | 4-nitro-5-chloro-2-(trifluoromethyl)benzimidazole |
| 32 | 7-nitro-4,5-dichloro-2-(trifluoromethyl)benzimidazole |
| 33 | 4-nitro-5,6-dichloro-2-(trifluoromethyl)benzimidazole |
| 34 | 4-nitro-5,6-dichloro-2-(perfluoroethyl)benzimidazole |
| 35 | 4-nitro-7-bromo-2,6-bis(trifluoromethyl)benzimidazole |
| 36 | 4-nitro-6-(trifluoromethyl)-2-(chlorodifluoromethyl)benzimidazole |
| 37 | 4-nitro-2,6-bis(trifluoromethyl)-7-chlorobenzimidazole |
| 38 | 6-nitro-2,4-bis(trifluoromethyl)benzimidazole |
| 39 | 4-nitro-6-(trifluoromethyl)-2-(2,2,3,3-tetrafluoroethyl)benzimidazole |
| 40 | 7-nitro-5-chloro-2-(perfluoro-n-propyl)benzimidazole |
| 41 | 7-nitro-5-(trifluoromethyl)-2-(1-(trifluoromethyl)-2,3,3,3-tetrafluoroethyl)benzimidazole |
| 42 | 7-nitro-5-chloro-2-(2,2,3,3-tetrafluoroethyl)benzimidazole |
| 43 | 4-nitro-6-(trifluoromethyl)-2-(2,2,3,3-tetrafluoroethyl)benzimidazole, salt with tri-n-butylamine |
| 44 | 4-nitro-6-(trifluoromethyl)-2-(2,2,3,3-tetrafluoroethyl)benzimidazole, salt with tribenzylamine |
| 45 | 4-nitro-6-(trifluoromethyl)-2-(2,2,3,3-tetrafluoroethyl)benzimidazole, salt with decylamine |

-continued

| Example # | Name |
|---|---|
| 46 | 4-nitro-6-(trifluoromethyl)-2-(2,2,3,3-tetrafluoroethyl)benzimidazole, salt with phenethylamine |
| 47 | 4-nitro-6-(trifluoromethyl)-2-(2,2,3,3-tetrafluoroethyl)benzimidazole, salt with di-n-hexylamine |
| 48 | 4-nitro-6-(trifluoromethyl)-2-(2,2,3,3-tetrafluoroethyl)benzimidazole, salt with tri-n-propylamine |
| 49 | 4-nitro-6-(trifluoromethyl)-2-(2,2,3,3-tetrafluoroethyl)benzimidazole, salt with dodecylamine |
| 50 | 4-nitro-6-(trifluoromethyl)-2-(2,2,3,3-tetrafluoroethyl)benzimidazole, salt with triethylamine |
| 51 | 4-nitro-6-(trifluoromethyl)-2-(perfluoroethyl)benzimidazole, sodium salt |
| 52 | 4-nitro-6-(trifluoromethyl)-2-(2,2,3,3-tetrafluoroethyl)benzimidazole, tetra-n-heptylammonium salt |
| 53 | 4-nitro-6-(trifluoromethyl)-2-(2,2,3,3-tetrafluoroethyl)benzimidazole, tetra-n-butylammonium salt |
| 54 | 4-nitro-6-(trifluoromethyl)-2-(2,2,3,3-tetrafluoroethyl)benzimidazole, tetra-n-propylammonium salt |
| 55 | 4-nitro-6-(trifluoromethyl)-2-(2,2,3,3-tetrafluoroethyl)benzimidazole, benzyltrimethylammonium salt |
| 56 | 1-hydroxy-4-nitro-2,6-bis(trifluoromethyl)benzimidazole |
| 57 | 1-hydroxy-4-nitro-6-(trifluoromethyl)-2-(2,2,3,3-tetrafluoroethyl)benzimidazole |
| 58 | 1-hydroxy-4-nitro-6-(trifluoromethyl)-2-(chlorodifluoromethyl)benzimidazole |
| 59 | allyl 4-nitro-2,6-bis(trifluoromethyl)-1-benzimidazolecarboxylate |
| 60 | 4-nitrophenyl 4-nitro-2,6-bis(trifluoromethyl)-1-benzimidazolecarboxylate |
| 61 | 4-nitro-N,N-di(n-propyl)-2,6-bis(trifluoromethyl)thio-1-benzimidazolecarboxamide |
| 62 | 7-nitro-N,N-di(n-propyl)-2,5-bis(trifluoromethyl)thio-1-benzimidazolecarboxamide |
| 63 | 7-nitro-1-(piperidinothionocarbonyl)-2,5-bis(trifluoromethyl)benzimidazole |
| 64 | 4-nitro-1-(piperidinothionocarbonyl)-2,6-bis(trifluoromethyl)benzimidazole |
| 65 | N-ethyl-4-nitro-2,6-bis(trifluoromethyl)benzimidazole-1-thiocarboxanilide |
| 66 | N-ethyl-7-nitro-2,5-bis(trifluoromethyl)benzimidazole-1-thiocarboxanilide |
| 67 | ethyl 4-nitro-2,6-bis(trifluoromethyl)-1-benzimidazolecarboxylate |
| 68 | phenyl 4-nitro-2,6-bis(trifluoromethyl)-1-benzimidazolecarboxylate |
| 69 | phenyl 7-nitro-2,5-bis(trifluoromethyl)-1-benzimidazolecarboxylate |
| 70 | N,N-diethyl-4-nitro-2,6-bis(trifluoromethyl)thio-1-benzimidazolecarboxamide |
| 71 | 1-acetyl-7-nitro-2,5-bis(trifluoromethyl)benzimidazole |
| 72 | 1-acetyl-4-nitro-2,6-bis(trifluoromethyl)benzimidazole |
| 73 | 1-hexanoyl-7-nitro-2,5-bis(trifluoromethyl)benzimidazole |
| 74 | 1-hexanoyl-4-nitro-2,6-bis(trifluoromethyl)benzimidazole |
| 75 | 2,6-bis(trifluoromethyl)-4-nitro-1-(phenylsulfonyl)benzimidazole |
| 76 | 1-(p-anisoyl)-4-nitro-2,6-bis(trifluoromethyl)benzimidazole |
| 77 | 1-methoxy-4-nitro-2,6-bis(trifluoromethyl)benzimidazole |
| 78 | n-hexyl 4-nitro-2,6-bis(trifluoromethyl)-1-benzimidazolecarboxylate |
| 79 | isopropyl 4-nitro-2,6-bis(trifluoromethyl)-1-benzimidazolecarboxylate |
| 80 | 1-benzoyl-4-nitro-2,6-bis(trifluoromethyl)benzimidazole |
| 81 | 1-(4-chlorobenzoyl)-4-nitro-2,6-bis(trifluoromethyl)benzimidazole |
| 82 | N,N-dimethyl-4-nitro-2,6-bis(trifluoromethyl)thio-1-benzimidazolecarboxamide |
| 83 | N,N-dimethyl-7-nitro-2,5-bis(trifluoromethyl)thio-1-benzimidazolecarboxamide |
| 84 | 4-nitro-1-(4-nitrobenzoyl)2,6-bis(trifluoromethyl)benzimidazole |
| 85 | benzyl 2,6-bis(trifluoromethyl)-4-nitro-1-benzimidazolecarboxylate |
| 86 | benzyl 2,5-bis(trifluoromethyl)-7-nitro-1-benzimidazolecarboxylate |
| 87 | methyl 4-nitro-2,6-bis(trifluoromethyl)-1-benzimidazolecarboxylate |
| 88 | methyl 7-nitro-2,5-bis(trifluoromethyl)-1-benzimidazolecarboxylate |
| 89 | n-butyl 4-nitro-2,6-bis(trifluoromethyl)benzimidazole-1- |

| Example # | Name |
|---|---|
| | carboxylate |
| 90 | isopropyl 2-(chlorodifluoromethyl)-4-nitro-6-(trifluoromethyl)-1-benzimidazolecarboxylate |
| 91 | 4-nitro-2,6-bis(trifluoromethyl)-1-benzimidazolyl methylcarbamate |
| 92 | phenyl 2-(chlorodifluoromethyl)-4-nitro-6-(trifluoromethyl)-1-benzimidazolecarboxylate |
| 93 | benzyl 4-nitro-2-(1,1,2,2-tetrafluoroethyl)-6-(trifluoromethyl)-1-benzimidazolecarboxylate |
| 94 | 1-methoxy-4-nitro-2-(1,1,2,2-tetrafluoroethyl)-6-(trifluoromethyl)benzimidazole |
| 95 | 2-ethylhexyl 4-nitro-2-(1,1,2,2-tetrafluoroethyl)-6-(trifluoromethyl)-1-benzimidazolecarboxylate |
| 96 | octyl 7-nitro-2-(1,1,2,2-tetrafluoroethyl)-5-(trifluoromethyl)-1-benzimidazolecarboxylate |
| 97 | octyl 4-nitro-2-(1,1,2,2-tetrafluoroethyl)-6-(trifluoromethyl)-1-benzimidazolecarboxylate |
| 98 | ethyl 4-nitro-2-(1,1,2,2-tetrafluoroethyl)-6-(trifluoromethyl)-1-benzimidazolecarboxylate |
| 99 | isopropyl 4-nitro-2-(1,1,2,2-tetrafluoroethyl)-6-(trifluoromethyl)-1-benzimidazolecarboxylate |
| 100 | 1-(phenoxycarbonyloxy)-2-(chlorodifluoromethyl)-4-nitro-6-(trifluoromethyl)benzimidazole |
| 101 | 1-methoxy-2-(chlorodifluoromethyl)-4-nitro-6-(trifluoromethyl)benzimidazole |
| 102 | ethyl 2-(chlorodifluoromethyl)-4-nitro-6-(trifluoromethyl)-1-benzimidazolecarboxylate |
| 103 | N,N-dimethyl-2-(chlorodifluoromethyl)-7-nitro-5-(trifluoromethyl)-thio-1-benzimidazolecarboxamide |
| 104 | N,N-dimethyl-2-(chlorodifluoromethyl)-4-nitro-6-(trifluoromethyl)-thio-1-benzimidazolecarboxamide |
| 105 | methyl 4-nitro-2-(1,1,2,2-tetrafluoroethyl)-6-(trifluoromethyl)-1-benzimidazolecarboxylate |
| 106 | allyl 4-nitro-2-(1,1,2,2-tetrafluoroethyl)-6-(trifluoromethyl)-1-benzimidazolecarboxylate |
| 107 | allyl 2-(chlorodifluoromethyl)-4-nitro-6-(trifluoromethyl)-1-benzimidazolecarboxylate |
| 108 | 1-(phenylsulfonyl)-2-(1,1,2,2-tetrafluoroethyl)-4-nitro-6-(trifluoromethyl)benzimidazole |

Compounds of Formula III which can be employed in the present invention include the following:

| Example # | Name |
|---|---|
| 109 | 2-hydroxy-4-nitro-6-(trifluoromethyl)-2-(2,2,3,3-tetrafluoroethyl)benzimidazoline, sodium salt |
| 110 | 2-hydroxy-4-nitro-6-(trifluoromethyl)-2-(2,2,3,3-tetrafluoroethyl)benzimidazoline, tetra-n-butylammonium salt |
| 111 | 2-hydroxy-4-nitro-6-(trifluoromethyl)-2-(2,2,3,3-tetrafluoroethyl)benzimidazoline, tetraethylammonium salt |
| 112 | 2-hydroxy-4-nitro-6-(trifluoromethyl)-2-(2,2,3,3-tetrafluoroethyl)benzimidazoline, silver salt |
| 113 | 2-hydroxy-4-nitro-6-(trifluoromethyl)-2-(2,2,3,3-tetrafluoroethyl)benzimidazoline, sodium salt |
| 114 | 2-hydroxy-4-nitro-2,6-bis(trifluoromethyl)benzimidazoline, sodium salt |
| 115 | 2-hydroxy-4-nitro-2,6-bis(trifluoromethyl)benzimidazoline, triethylamine salt |
| 116 | 2-hydroxy-4-nitro-6-(trifluoromethyl)-2-(2,2,3,3-tetrafluoroethyl)benzimidazoline, lithium salt |
| 117 | 2-hydroxy-4-nitro-6-chloro-2-(difluoromethyl)benzimidazoline, hemicalcium salt |
| 118 | 2-hydroxy-4-nitro-6-(trifluoromethyl)-2-(2,2,3,3-tetrafluoroethyl)benzimidazoline, hemicalcium salt |

The polyethers are a known class of antibiotics showing common structural features. A review article is found in the Kirk-Othmer Encyclopedia of Chemical Technology—4th Ed., Volume #3, pages 306–322, and this article is incorporated herein by reference. As noted in this review article, the polyethers exhibit anticoccidial activity, and are presently the principal chemotherapeutics, worldwide, for the control of coccidiosis.

Representative polyethers which can be used in the present invention include the following; the noted reference patents are incorporated herein by reference.

| | |
|---|---|
| monensin | 3,501,568 |
| laidlomycin | |
| nigericin | |
| grisorixin | |
| dianemycin | |
| lenoremycin | |
| salinomycin | 3,857,948 |
| narasin | 4,038,384 |
| lonomycin | |
| antibiotic X206 | |
| allorixin | |
| septamycin | |
| antibiotic A204 | 3,705,238 |
| etheromycin | |
| lasalocid | 3,719,753 |
| isolasalocid | |
| lysocellin | |
| antibiotic A231 87 | 4,582,822 |
| portmicin (antibiotic A80190) | 4,683,204 |
| kijimicin | |
| antibiotic A82810 | EPO X-7412 |
| maduramicin factor A (X-4868A) | 4,407,946 |
| maduramicin factor C (LLC-23024B) | |
| semduramicin. | |

There are certain preferred embodiments of the present invention. A preferred embodiment of Formula I and II are compounds wherein the benzo ring is substituted by nitro and a single $CF_3$ (i.e., compounds wherein m=1 and n=0). In Formula I, the preference is for $R^2$ =trifluoroacetyl or (1,1,2,2-tetrafluoropropionyl) and $R^4$=H or the same moiety represented by $R^2$. In Formula II, the preference is for $R^5$=(1,1,2,2-tetrafluoroethyl). Especially preferred compounds are:

3-nitro-5-(trifluoromethyl)-$N^1$-(2,2,3,3-tetrafluoropropionyl)-o-phenylenediamine 4-nitro-6-(trifluoromethyl)-2-(2,2,3,3-tetrafluoroethyl)benzimidazole 1-hydroxy-4-nitro-6-(trifluoromethyl)-2-(2,2,3,3-tetrafluoroethyl)benzimidazole Among the benzimidazolines of Formula III, preferences are the same for the benzo substitution and $R^5$; a preferred salt is sodium ($R^6$). Thus, especially preferred compounds are 2-hydroxy-4-nitro-2,6-bis(trifluoromethyl)benzimidazoline, sodium salt 2-hydroxy-4-nitro-6-(trifluoromethyl)-2-(2,2,3,3-tetrafluoroethyl)benzimidazoline, sodium salt Among the polyethers, preferred compounds are antibiotic A204, portmicin, antibiotic A82810, maduramicin, and semduramicin.

Combined therapy with both (1) a phenylenediamine, benzimidazole, or benzimidazoline, and (2) a polyether, is a preferred embodiment of the present invention.

The present invention can be employed for the control of coccidiosis in any fowl. Chickens and turkeys are the species most commonly treated for coccidiosis but the present invention can also be used with other poultry species, such as ducks, geese, quail, pheasants and ostriches.

The present invention can be used to prevent or treat coccidiosis attributable to any species. The species which commonly cause coccidiosis in chickens are

*Eimeria acervulina*

*Eimeria brunetti*

*Eimeria maxima*

*Eimeria necatrix*

*Eimeria tenella*

The species which commonly cause coccidiosis in turkeys are

*Eimeria meleagrimitis*

*Eimeria gallopavonis*

*Eimeria adenoeides*

*Eimeria dispersa*

Coccidiosis in other poultry species is attributable to yet other protozoan species known to those skilled in the art.

The present invention is useful generally for the prevention and/or treatment of coccidiosis; however, it is particularly useful regarding those coccidiosis-causing species which are insensitive to the polyethers, or which, based on laboratory trials or intensive use experience, could become insensitive. Thus, the present invention presents a technique for controlling coccidiosis while reducing the risk of developing insensitivity or resistance to the polyethers.

The present invention is practiced in the usual fashion of anticoccidials, that is, because coccidiosis is a malady of the intestinal tract, an anticoccidial must be administered in a way to reach the intestinal tract. This is typically achieved by incorporating the present agents in the feed. Anticoccidials are sometimes administered via the drinking water, and this route is possible for the compounds of Formula I, II, and III, especially in their salt forms. However, because of their low solubility, the polyethers are not readily administered by this route. In the embodiment of the present invention which employs both a compound of Formula I, II, or III, as well as a polyether, the former can be administered by the feed and the latter via the drinking water. In the most preferred practice however, both are administered in the feed.

The present active agents are incorporated into an animal feed in the manner usual for anticoccidials. Typically, a compound of Formula I or II, or a compound of Formula I, II, and III as well as a polyether, are incorporated into a "premix." The premix contains the active agent or agents as well as physiologically acceptable carriers and feedstuffs. The premix is relatively concentrated and is adapted to be diluted with other carriers, vitamin and mineral supplements, and feedstuffs to form the final animal feed. Premixes which are intermediate in concentration of active agent between a first premix and the final animal feed are sometimes employed in the industry and can be used in implementing the present invention.

When employing a compound of Formula I or II as sole active agent, a premix desirably contains the agent at a concentration of from 0.1 to 50.0% by weight. Preferred premixes will generally contain a compound of Formula I or II at a concentration of from 0.5 to 25.0%; by weight. When employing both a compound of Formula I, II, or III, as well as a polyether, a premix desirably contains concentrations of from 0.2 to 25.0% by weight of each active agent. Combined therapy can also be obtained using one premix containing the compound of Formula I, II, or III, and a second premix containing the polyether. Both mixes are added to carriers, vitamin and mineral supplements, and feedstuffs to yield a single animal feed containing both active agents. The identity of the other components of the premix and ultimate animal feed is not critical; exemplary formulations are listed below.

Various compounds to be employed in accordance with the present invention were evaluated in a standardized chicken battery test. In this test, the respective compound was mixed well with a small portion of a basal diet, to constitute a premix, and the resulting premix was added to a large amount of the same basal diet. This resulted in the ultimate diet fed to the chickens, containing the respective compound.

The battery test was conducted with Peterson×Hubbard cockerel chicks, beginning when the chicks were approximately nine days old. There were generally four chicks per pen and three or four pens per treatment. All chicks were housed in stainless steel wire cages, 13"×21"×9". The respective diet and water were provided ad libitum beginning at approximately day nine. All birds except those of a non-infected control group were infected with two or three species of Eimeria; infection was by crop intubation of sporulated oocysts, usually two days after the trial began (in some tests, one day after the trial began). The chicks were maintained on the trial for approximately nine days at which time they were killed and the intestinal tracts evaluated for the degree of lesions attributable to coccidiosis. Other parameters evaluated during the test were mortality, weight gain, and feed/gain.

The composition of the basal feed was as follows[1]:

| Ingredients | % |
| --- | --- |
| Corn, Yellow, Ground | 53.42 |
| Soybean Meal (49%) | 31.73 |
| Animal Fat | 2.83 |
| Fish Meal-Menhaden | 5.00 |
| Corn Distillers Dried Solubles | 4.00 |
| Dicalcium Phosphate | 1.28 |
| Ground Limestone | 0.62 |
| Vitamin Premix TK-01 (1.03)[2] | 0.50 |
| Salt (NaCl) | 0.30 |
| Trace Mineral Premix TK-01 (1.02)[3] | 0.10 |
| Methionine Hydroxy Analog | 0.17 |
| Selenium Premix[3] | 0.05 |
| Total | 100.00 |

[1]Final feed is in mash form.

| Ingredients | % |
| --- | --- |

[2]Vitamin premix provides 3000 IU of Vitamin A, 900 ICU of Vitamin $D_3$, 40 mg of Vitamin E, 0.7 mg of Vitamin K, 1000 mg of choline, 70 mg of niacin, 4 mg of pantothenic acid, 4 mg of ribovlavin, 0.10 mg of Vitamin $B_{12}$, 0.10 mg of biotin and 125 mg of ethoxyquin per kg of complete feed.
[3]Trace mineral premixes provide 75 mg of Mn, 50 mg of Zn, 25 mg of Fe, 1 mg of I, and 0.10 mg of Se per kg of complete feed.

CALCULATED ANALYSIS

| | | | | | |
| --- | --- | --- | --- | --- | --- |
| Crude Protein, | % | 23.50 | Vitamin K, | mg/kg | 0.70 |
| ME, | Kcal/kg | 3100.00 | Choline, | mg/kg | 2178.00 |
| ME/CP Ratio | | 132.00 | Niacin, | mg/kg | 96.50 |
| Fat, | % | 5.70 | Pant. Acid, | mg/kg | 12.60 |
| Fiber, | % | 2.70 | Riboflavin, | mg/kg | 6.40 |
| Ash, | % | 6.00 | Thiamine, | mg/kg | 2.80 |
| Calcium, | % | 0.85 | Folic Acid, | mg/kg | 1.50 |
| Total P, | % | 0.77 | Biotin, | mcg/kg | 296.00 |
| Vitamin. A, | IU/kg | 4765.00 | Vit. $B_{12}$, | mcg/kg | 107.00 |
| Vitamin $D_3$, | ICU/kg | 900.00 | Vitamin B6, | mg/kg | 7.60 |
| Vitamin E, | mg/kg | 56.50 | | | |
| Xanthophyll, | mg/kg | 8.30 | Linoleic Acid, | % | 1.30 |
| Manganese, | mg/kg | 101.30 | Iron, | mg/kg | 119.90 |
| Copper, | mg/kg | 17.20 | Zinc, | mg/kg | 85.40 |
| Selenium | mcg/kg | 251.00 | Magnesium, | mg/kg | 2003.00 |
| Potassium, | mg/kg | 9072.00 | Sodium, | mg/kg | 1670.00 |
| Iodine, | mg/kg | 1.00 | Arginine, | % | 1.685 |
| Lysine, | % | 1.41 | Glycine, | % | 1.400 |
| Methionine, | % | 0.56 | Cystine, | % | 0.356 |
| TSAA, | % | 0.920 | Tryptophan, | % | 0.333 |

Results of trials in accordance with the present invention are reported in the following tables. "#" columns refer to the number of pens. Mortality is reported using both (1) due to all causes, and (2) due to coccidiosis, only. Weight gain is calculated only for surviving chicks. In most experiments, feed:gain ratio was calculated using only pens in which no mortality occurred. However, in some experiments, an adjusted feed:gain ratio was calculated by correcting for mortality. To determine what method was used to calculate feed:gain, compare the number of pens used to calculate mortality with the number of pens used to calculate feed:gain. If no mortality occurred within a particular treatment group, then all pens were used to calculate feed:gain ratio and no adjustment was necessary. If mortality occurred in a particular treatment group and there are fewer pens used for feed:gain than for mortality, then feed:gain was calculated using only pens in which mortality did not occur. However, if mortality occurred and the number of pens used to calculate mortality is equal to the number of pens used to calculate feed:gain, then an adjusted feed:gain ratio was calculated. Statistical analyses were by the Student-Newman-Keul's Multiple Range Test, using Gerbhardt's Algorithm for unequal sample size. Means within a column with no common superscript letter differ ($P<0.05$).

EXPERIMENT NO. 1
Statistical Analyses of Percent Mortality, Weight Gain, Feed/Gain,
Intestinal and Cecal Lesion Scores of broiler cockerels inoculated with
*E. acervulina* and *E. tenella*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 3 | 0.0 b | 3 | 0.0 a | 3 | 232.3 a | 3 | 1.584 b–c | 3 | 0.00 d | 3 | 0.00 e |
| IC | | | | | | | | | | | | |
| 0 | 3 | 8.3 b | 3 | 8.3 a | 3 | 221.6 a–b | 2 | 1.733 a–c | 3 | 6.00 a | 3 | 3.33 a |
| A82810 | | | | | | | | | | | | |
| 2 | 3 | 0.0 b | 3 | 0.0 a | 3 | 202.7 b | 3 | 1.908 a | 3 | 6.08 a | 3 | 3.33 a |
| 4 | 3 | 0.0 b | 3 | 0.0 a | 3 | 221.4 a–b | 3 | 1.819 a–c | 3 | 3.83 a–c | 3 | 3.08 a–b |
| 8 | 3 | 0.0 b | 3 | 0.0 a | 3 | 231.8 a–b | 3 | 1.718 a–c | 3 | 1.50 c–d | 3 | 2.92 a–c |
| Example No. 57 | | | | | | | | | | | | |
| 3 | 3 | 8.3 b | 3 | 8.3 a | 3 | 217.1 a–b | 2 | 1.879 a–b | 3 | 5.33 a–b | 3 | 3.42 a |
| 6 | 3 | 8.3 b | 3 | 8.3 a | 3 | 221.8 a–b | 2 | 1.715 a–c | 3 | 2.75 b–d | 3 | 2.92 a–c |
| 12 | 3 | 16.7 b | 3 | 0.0 a | 3 | 235.6 a–b | 2 | 1.906 a–c | 3 | 0.00 d | 3 | 0.33 e |
| A82810 + Example No. 57 | | | | | | | | | | | | |
| 2+3 | 3 | 16.7 b | 3 | 16.7 a | 3 | 193.1 b | 2 | 1.926 a | 3 | 4.08 a–c | 3 | 3.33 a |
| 2+6 | 3 | 8.3 b | 3 | 0.0 a | 3 | 239.8 a–b | 2 | 1.769 a–c | 3 | 0.58 d | 3 | 2.56 a–d |
| 2+12 | 3 | 16.7 b | 3 | 0.0 a | 3 | 224.6 a–b | 1 | 1.843 a–c | 3 | 0.00 d | 3 | 0.83 e |
| 4+3 | 3 | 0.0 b | 3 | 0.0 a | 3 | 255.4 a–b | 3 | 1.675 a–c | 3 | 1.00 c–d | 3 | 2.58 a–d |
| 4+6 | 3 | 8.3 b | 3 | 0.0 a | 3 | 248.9 a–b | 2 | 1.692 a–c | 3 | 0.00 d | 3 | 1.56 b–e |
| 4+12 | 3 | 75.0 a | 3 | 0.0 a | 3 | 220.9 a–b | | | 3 | 1.50 c–d | 3 | 1.17 d–e |
| 8+3 | 3 | 0.0 b | 3 | 0.0 a | 3 | 269.8 a | 3 | 1.546 c | 3 | 0.58 d | 3 | 1.33 c–e |
| 8+6 | 3 | 8.3 b | 3 | 0.0 a | 3 | 257.4 a–b | 2 | 1.710 a–c | 3 | 0.25 d | 3 | 0.92 e |
| 8+12 | 3 | 41.7 b | 3 | 0.0 a | 3 | 238.6 a–b | 1 | 1.958 a–c | 3 | 0.00 d | 3 | 0.33 e |

EXPERIMENT NO. 2
Statistical Analyses of Percent Mortality, Weight Gain, Feed/Gain,
Intestinal and Cecal Lesion Scores of broiler cockerels inoculated with
*E. maxima* and *E. tenella*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 3 | 8.3 a | 3 | 0.0 a | 3 | 236.8 a | 2 | 1.537 b | 3 | 0.00 d | 3 | 0.00 c |
| IC | | | | | | | | | | | | |
| 0 | 3 | 25.0 a | 3 | 16.7 a | 3 | 134.1 d–e | | | 3 | 7.50 a–b | 3 | 3.44 a |
| A82810 | | | | | | | | | | | | |
| 2 | 3 | 8.3 a | 3 | 8.3 a | 3 | 154.6 e | 2 | 2.332 a | 3 | 8.75 a | 3 | 3.42 a |
| 4 | 3 | 0.0 a | 3 | 0.0 a | 3 | 172.2 d–e | 3 | 2.053 a–b | 3 | 7.83 a–b | 3 | 3.08 a |
| 8 | 3 | 0.0 a | 3 | 0.0 a | 3 | 230.0 a–d | 3 | 1.669 b | 3 | 8.00 a–b | 3 | 3.08 a |
| Example No. 57 | | | | | | | | | | | | |
| 3 | 3 | 0.0 a | 3 | 0.0 a | 3 | 180.0 d–e | 3 | 2.06 a–b | 3 | 8.35 a | 3 | 3.50 a |
| 6 | 3 | 8.3 a | 3 | 8.3 a | 3 | 184.6 c–e | 2 | 2.079 a–b | 3 | 8.42 a | 3 | 3.58 a |
| 8 | 3 | 41.7 a | 3 | 0.0 a | 3 | 235.8 a–d | i | 1.725 a–b | 3 | 3.00 c–d | 3 | 1.25 b–c |
| A82810 + Example No. 59 | | | | | | | | | | | | |
| 2+3 | 3 | 0.0 a | 3 | 0.0 a | 3 | 201.2 b–e | 3 | 1.870 a–b | 3 | 7.00 a–b | 3 | 3.33 a |
| 2+6 | 3 | 8.3 a | 3 | 0.0 a | 3 | 249.8 a–c | 2 | 1.626 b | 3 | 1.00 d | 3 | 1.03 b–c |
| 2+12 | 3 | 16.7 a | 3 | 0.0 a | 3 | 215.7 a–e | 1 | 1.881 a–b | 3 | 0.00 d | 3 | 0.33 c |
| 4+3 | 3 | 25.0 a | 3 | 0.0 a | 3 | 229.0 a–d | 1 | 1.698 a–b | 3 | 7.78 a–b | 3 | 3.06 a |
| 4+6 | 3 | 0.0 a | 3 | 0.0 a | 3 | 245.8 a–c | 3 | 1.693 b | 3 | 1.58 d | 3 | 2.08 a–b |
| 4+12 | 3 | 41.7 a | 3 | 0.0 a | 2 | 211.3 a–e | 1 | 1.808 a–b | 2 | 0.00 d | 2 | 0.00 c |
| 8+3 | 3 | 8.3 a | 3 | 0.0 a | 3 | 258.3 a–b | 2 | 1.608 b | 3 | 4.83 b–c | 3 | 2.06 a–b |
| 8+6 | 3 | 8.3 a | 3 | 0.0 a | 3 | 255.5 a–b | 2 | 1.513 b | 3 | 1.00 d | 3 | 0.50 c |
| 8+12 | 3 | 25.0 a | 3 | 0.0 a | 3 | 215.2 a–e | 1 | 1.813 a–b | 3 | 0.00 d | 3 | 0.00 c |

EXPERIMENT NO. 3
Statistical Analyses of Percent Mortality, Weight Gain, Feed/Gain,
Intestinal and Cecal Lesion Scores of broiler cockerels inoculated with
E. tenella and E. acervulina

| Treatment | Mortality Mean | | | | Wt. Gain | | Feed/Gain | | Lesion Scores Intestinal | | Cecal | |
|---|---|---|---|---|---|---|---|---|---|---|---|---|
| PPM | # | Total % | # | % DTC | # | Mean | # | Mean | # | Mean | # | Mean |
| NC | | | | | | | | | | | | |
| 0 | 3 | 0.0 b | 3 | 0.0 b | 3 | 274.8 a | 3 | 1.549 b | 3 | 0.00 d | 3 | 0.00 d |
| IC | | | | | | | | | | | | |
| 0 | 3 | 16.7 b | 3 | 16.7 a | 3 | 195.2 b | 1 | 2.305 a–b | 3 | 5.25 a | 3 | 3.67 a |
| A82810 | | | | | | | | | | | | |
| 2 | 3 | 0.0 b | 3 | 0.0 b | 3 | 228.6 a–b | 3 | 1.886 a–b | 3 | 2.00 b | 3 | 2.67 b |
| 4 | 3 | 0.0 b | 3 | 0.0 b | 3 | 255.2 a | 3 | 1.762 b | 3 | 1.25 c | 3 | 3.42 a–b |
| 8 | 3 | 0.0 b | 3 | 0.0 b | 3 | 244.2 a | 3 | 1.772 b | 3 | 1.17 c | 3 | 3.33 a–b |
| Example No. 113 | | | | | | | | | | | | |
| 6 | 3 | 0.0 b | 3 | 0.0 b | 3 | 244.7 a | 3 | 1.747 b | 3 | 0.58 d | 3 | 1.50 c |
| 12 | 3 | 0.0 b | 3 | 0.0 b | 3 | 182.1 b | 3 | 2.105 a–b | 3 | 0.00 d | 3 | 0.17 d |
| A82810 + Example No. 113 | | | | | | | | | | | | |
| 2+6 | 3 | 0.0 b | 3 | 0.0 b | 3 | 254.5 a | 3 | 1.722 b | 3 | 0.00 d | 3 | 0.58 d |
| 2+12 | 3 | 8.3 b | 3 | 0.0 b | 3 | 192.3 b | 2 | 2.125 a–b | 3 | 0.00 d | 3 | 0.00 d |
| 4+6 | 3 | 0.0 b | 3 | 0.0 b | 3 | 251.8 a | 3 | 1.731 b | 3 | 0.00 d | 3 | 0.75 d |
| 4+12 | 3 | 16.7 b | 3 | 0.0 b | 3 | 193.9 b | 1 | 2.006 a–b | 3 | 0.00 d | 3 | 0.19 d |
| 8+6 | 3 | 8.3 b | 3 | 0.0 b | 3 | 254.0 a | 2 | 1.839 a–b | 3 | 0.00 d | 3 | 0.39 d |
| 8+12 | 3 | 0.0 b | 3 | 0.0 b | 3 | 185.7 b | 3 | 2.323 a | 3 | 0.00 d | 3 | 0.00 d |
| 8+24 | 1 | 75.0 a | 1 | 0.0 b | 1 | 67.0 c | | | 1 | 0.00 d | 1 | 0.00 d |

EXPERIMENT NO. 4
Statistical Analyses of Percent Mortality, Weight Gain, Feed/Gain,
Intestinal and Cecal Lesion Scores of broiler cockerels inoculated with
E. tenella and E. maxima

| Treatment | Mortality Mean | | | | Wt. Gain | | Feed/Gain | | Lesion Scores Intestinal | | Cecal | |
|---|---|---|---|---|---|---|---|---|---|---|---|---|
| PPM | # | Total % | # | % DTC | # | Mean | # | Mean | # | Mean | # | Mean |
| NC | | | | | | | | | | | | |
| 0 | 3 | 0.0 c | 3 | 0.0 b | 3 | 295.8 a | 3 | 1.578 d | 3 | 0.00 c | 3 | 0.00 c |
| IC | | | | | | | | | | | | |
| 0 | 3 | 33.3 b–c | 3 | 33.3 a | 3 | 170.3 b–d | | | 3 | 5.33 b | 3 | 3.75 a |
| A82810 | | | | | | | | | | | | |
| 2 | 3 | 41.7 b | 3 | 41.7 a | 3 | 138.4 d | | | 3 | 6.42 b | 3 | 3.75 a |
| 4 | 3 | 25.0 b–c | 3 | 16.7 b | 3 | 160.0 c–d | 1 | 2.368 a | 3 | 7.17 a–b | 3 | 3.56 a |
| 8 | 3 | 0.0 c | 3 | 0.0 b | 3 | 208.3 b–d | 3 | 1.978 a–c | 3 | 8.67 a | 3 | 3.58 a |
| Example No. 113 | | | | | | | | | | | | |
| 6 | 3 | 0.0 c | 3 | 0.0 b | 3 | 242.4 a–c | 3 | 1.681 c–d | 3 | 2.42 c | 3 | 1.08 b |
| 12 | 3 | 16.7 b–c | 3 | 0.0 b | 3 | 180.4 b–d | 2 | 2.130 a–b | 3 | 0.00 c | 3 | 0.00 c |
| A82810 + Example No. 113 | | | | | | | | | | | | |
| 2+6 | 3 | 0.0 c | 3 | 0.0 b | 3 | 251.0 a–b | 3 | 1.771 b–d | 3 | 0.17 c | 3 | 0.83 b–c |
| 2+12 | 3 | 0.0 c | 3 | 0.0 b | 3 | 198.3 b–d | 3 | 2.011 a–c | 3 | 0.00 c | 3 | 0.00 c |
| 4+6 | 3 | 0.0 c | 3 | 0.0 b | 3 | 241.7 a–c | 3 | 1.783 b–d | 3 | 0.00 c | 3 | 0.25 c |
| 4+12 | 3 | 0.0 c | 3 | 0.0 b | 3 | 190.3 b–d | 3 | 2.149 a–b | 3 | 0.00 c | 3 | 0.00 c |
| 4+24 | 2 | 75.0 a | 2 | 0.0 b | 2 | 72.8 e | | | 2 | 0.00 c | 2 | 0.00 c |
| 8+6 | 3 | 0.0 c | 3 | 0.0 b | 3 | 242.3 a–c | 3 | 1.782 b–d | 3 | 0.08 c | 3 | 0.25 c |
| 8+12 | 3 | 8.3 c | 3 | 0.0 b | 3 | 163.0 c–d | 2 | 2.235 a | 3 | 0.00 c | 3 | 0.00 c |

EXPERIMENT NO. 5
Statistical Analyses of Percent Mortality, Weight Gain, Feed/Gain,
Intestinal and Cecal Lesion Scores of broiler cockerels inoculated with
*E. acervulina* and *E. tenella*

| Treatment | Mortality Mean | | | | | | Wt. Gain | | Feed/Gain | | Lesion Scores | | | | | |
|---|---|---|---|---|---|---|---|---|---|---|---|---|---|---|---|---|
| | | | | | | | | | | | Intestinal | | | Cecal | | |
| PPM | # | Total % | | # | % DTC | | # | Mean | # | Mean | # | Mean | | # | Mean | |
| NC | | | | | | | | | | | | | | | | |
| 0 | 3 | 0.0 | a | 3 | 0.0 | a | 3 | 252.6 a | 3 | 1.677 | 1 | 3 | 0.00 c | 3 | 0.00 | e |
| IC | | | | | | | | | | | | | | | | |
| 0 | 3 | 0.0 | a | 3 | 0.0 | a | 3 | 205.6 a | 3 | 2.059 a | 3 | 5.67 a | 3 | 2.92 | a–b |
| A82810 | | | | | | | | | | | | | | | | |
| 2 | 3 | 0.0 | a | 3 | 0.0 | a | 3 | 226.1 a | 3 | 1.894 a | 3 | 4.83 a | 3 | 2.02 | a–b |
| 4 | 3 | 8.3 | a | 3 | 0.0 | a | 3 | 254.1 a | 2 | 1.612 a | 3 | 1.42 b–c | 3 | 3.11 | a–b |
| 8 | 3 | 0.0 | a | 3 | 0.0 | a | 3 | 252.5 a | 3 | 1.802 a | 3 | 0.92 b–c | 3 | 1.83 | a–d |
| Example No. 57 | | | | | | | | | | | | | | | | |
| 2 | 3 | 16.7 | a | 3 | 0.0 | a | 3 | 212.4 a | 1 | 1.878 a | 3 | 5.00 a | 3 | 3.44 | a |
| 4 | 3 | 16.7 | a | 3 | 0.0 | a | 3 | 208.2 a | 1 | 2.025 a | 3 | 4.06 a | 3 | 3.06 | a–b |
| 8 | 3 | 16.7 | a | 3 | 8.3 | a | 3 | 233.7 a | 1 | 1.829 a | 3 | 1.28 b–c | 3 | 3.39 | a–b |
| A82810 + Example No. 57 | | | | | | | | | | | | | | | | |
| 2+2 | 3 | 8.3 | a | 3 | 8.3 | a | 3 | 225.5 a | 2 | 1.862 a | 3 | 3.17 a–b | 3 | 2.58 | a–c |
| 2+4 | 3 | 8.3 | a | 3 | 0.0 | a | 3 | 236.0 a | 2 | 1.735 a | 3 | 1.14 b–c | 3 | 2.25 | a–d |
| 2+8 | 3 | 16.7 | a | 3 | 0.0 | a | 3 | 214.6 a | 1 | 1.915 a | 3 | 0.08 c | 3 | 0.86 | c–e |
| 4+2 | 3 | 0.0 | a | 3 | 0.0 | a | 3 | 232.2 a | 3 | 1.723 a | 3 | 1.92 b–c | 3 | 2.00 | a–d |
| 4+4 | 3 | 0.0 | a | 3 | 0.0 | a | 3 | 221.8 a | 3 | 1.903 a | 3 | 0.42 b–c | 3 | 2.00 | a–d |
| 4+8 | 3 | 8.3 | a | 3 | 0.0 | a | 3 | 236.4 a | 2 | 1.715 a | 3 | 0.00 c | 3 | 0.58 | d–e |
| 8+2 | 3 | 0.0 | a | 3 | 0.0 | a | 3 | 245.3 a | 3 | 1.714 a | 3 | 0.67 b–c | 3 | 1.50 | a–e |
| 8+4 | 3 | 0.0 | a | 3 | 0.0 | a | 3 | 259.0 a | 3 | 1.624 a | 3 | 0.33 b–c | 3 | 1.58 | a–e |
| 8+8 | 3 | 0.0 | a | 3 | 0.0 | a | 3 | 248.5 a | 3 | 1.660 a | 3 | 0.00 c | 3 | 0.00 | e |

EXPERIMENT NO. 6
Statistical Analyses of Percent Mortality, Weight Gain, Feed/Gain,
Intestinal and Cecal Lesion Scores of broiler cockerels inoculated with
*E. maxima* and *E. tenella*

| Treatment | Mortality Mean | | | | | | Wt. Gain | | Feed/Gain | | Lesion Scores | | | | | |
|---|---|---|---|---|---|---|---|---|---|---|---|---|---|---|---|---|
| | | | | | | | | | | | Intestinal | | | Cecal | | |
| PPM | # | Total % | | # | % DTC | | # | Mean | # | Mean | # | Mean | | # | Mean | |
| NC | | | | | | | | | | | | | | | | |
| 0 | 3 | 8.3 | b | 3 | 0.0 | b | 3 | 254.8 a | 2 | 1.806 a | 3 | 0.00 c | 3 | 0.22 | c |
| IC | | | | | | | | | | | | | | | | |
| 0 | 3 | 0.0 | b | 3 | 0.0 | b | 3 | 165.6 b–c | 3 | 2.182 a | 3 | 8.92 a | 3 | 3.00 | a |
| A82810 | | | | | | | | | | | | | | | | |
| 2 | 3 | 8.3 | b | 3 | 8.3 | b | 3 | 195.1 a–c | 2 | 1.957 a | 3 | 8.25 a | 3 | 3.25 | a |
| 4 | 3 | 8.3 | b | 3 | 0.0 | b | 3 | 189.8 a–c | 2 | 2.083 a | 3 | 7.39 a | 3 | 3.19 | a |
| 8 | 3 | 0.0 | b | 3 | 0.0 | b | 3 | 217.9 a–b | 3 | 1.863 a | 3 | 8.83 a | 3 | 2.67 | a |
| Example No. 57 | | | | | | | | | | | | | | | | |
| 2 | 3 | 41.7 | a | 3 | 33.3 | a | 3 | 126.4 c | | | 3 | 8.33 a | 3 | 3.50 | a |
| 4 | 3 | 8.3 | b | 3 | 8.3 | b | 3 | 177.8 a–c | 2 | 2.048 a | 3 | 8.25 a | 3 | 3.08 | a |
| 8 | 3 | 0.0 | b | 3 | 0.0 | b | 3 | 217.2 a–b | 3 | 1.860 a | 3 | 6.50 a–b | 3 | 2.50 | a–b |
| A82810 + Example No. 57 | | | | | | | | | | | | | | | | |
| 2+2 | 3 | 8.3 | b | 3 | 0.0 | b | 3 | 178.3 a–c | 2 | 2.170 a | 3 | 8.50 a | 3 | 3.17 | a |
| 2+4 | 3 | 0.0 | b | 3 | 0.0 | b | 3 | 221.8 a–b | 3 | 1.840 a | 3 | 5.67 a–b | 3 | 3.00 | a |
| 2+8 | 3 | 8.3 | b | 3 | 0.0 | b | 3 | 226.6 a–b | 2 | 1.798 a | 3 | 0.89 c | 3 | 1.08 | c |
| 4+2 | 3 | 8.3 | b | 3 | 0.0 | b | 3 | 226.5 a–b | 3 | 1.728 a | 3 | 7.50 a | 3 | 3.06 | a |
| 4+4 | 3 | 0.0 | b | 3 | 0.0 | b | 3 | 242.6 a–b | 3 | 1.713 a | 3 | 6.17 a–b | 3 | 2.25 | a–b |
| 4+8 | 3 | 8.3 | b | 3 | 0.0 | b | 3 | 248.1 a–b | 2 | 1.721 a | 3 | 0.00 c | 3 | 0.25 | c |
| 8+2 | 3 | 0.0 | b | 3 | 0.0 | b | 3 | 226.8 a–b | 3 | 1.750 a | 3 | 4.33 a–b | 3 | 0.83 | c |
| 8+4 | 3 | 0.0 | b | 3 | 0.0 | b | 3 | 231.5 a–b | 3 | 1.756 a | 3 | 2.58 b–c | 3 | 1.42 | b–c |
| 8+8 | 3 | 16.7 | b | 3 | 0.0 | b | 3 | 238.6 a–b | 1 | 1.730 a | 3 | 0.00 c | 3 | 0.33 | c |

EXPERIMENT NO. 7
Statistical Analyses of Percent Mortality, Weight Gain, Feed/Gain, Intestinal and Cecal Lesion Scores of broiler cockerels inoculated with *E. tenella* and *E. acervulina*

| Treatment PPM | Mortality Mean # | Total % | | # | % DTC | | Wt. Gain # | Mean | | Feed/Gain # | Mean | | Intestinal # | Mean | | Cecal # | Mean | |
|---|---|---|---|---|---|---|---|---|---|---|---|---|---|---|---|---|---|---|
| NC | | | | | | | | | | | | | | | | | | |
| 0 | 3 | 0.0 | a | 3 | 0.0 | a | 3 | 299.0 | a | 3 | 1.549 | e | 3 | 0.00 | e | 3 | 0.08 | f |
| IC | | | | | | | | | | | | | | | | | | |
| 0 | 3 | 8.3 | a | 3 | 8.3 | a | 3 | 221.4 | c-e | 2 | 1.922 | a-b | 3 | 5.58 | a | 3 | 3.42 | a |
| A82810 | | | | | | | | | | | | | | | | | | |
| 2 | 3 | 0.0 | a | 3 | 0.0 | a | 3 | 234.4 | b-e | 3 | 1.814 | a-d | 3 | 2.83 | c-d | 3 | 2.92 | a-b |
| 4 | 3 | 0.0 | a | 3 | 0.0 | a | 3 | 264.3 | a-c | 3 | 1.667 | b-e | 3 | 4.33 | b | 3 | 3.00 | a-b |
| 8 | 3 | 0.0 | a | 3 | 0.0 | a | 3 | 270.5 | a-c | 3 | 1.645 | c-e | 3 | 1.67 | d-e | 3 | 3.00 | a-b |
| Example No. 113 | | | | | | | | | | | | | | | | | | |
| 2 | 3 | 0.0 | a | 3 | 0.0 | a | 3 | 211.5 | d-e | 3 | 1.868 | a-c | 3 | 3.50 | b-c | 3 | 3.08 | a-b |
| 4 | 3 | 0.0 | a | 3 | 0.0 | a | 3 | 251.8 | a-e | 3 | 1.685 | b-e | 3 | 0.42 | e | 3 | 2.17 | b-c |
| 8 | 3 | 0.0 | a | 3 | 0.0 | a | 3 | 231.3 | b-e | 3 | 1.813 | a-d | 3 | 0.00 | e | 3 | 0.75 | d-f |
| A82810 + Example No. 113 | | | | | | | | | | | | | | | | | | |
| 2+2 | 3 | 16.7 | a | 3 | 0.0 | a | 3 | 270.2 | a-c | 1 | 1.780 | a-e | 3 | 1.42 | d-e | 3 | 3.06 | a-b |
| 2+4 | 3 | 0.0 | a | 3 | 0.0 | a | 3 | 257.1 | a-d | 3 | 1.712 | b-e | 3 | 0.42 | e | 3 | 1.67 | c-d |
| 2+8 | 3 | 0.0 | a | 3 | 0.0 | a | 3 | 231.2 | b-e | 3 | 1.758 | b-e | 3 | 0.00 | e | 3 | 0.00 | f |
| 4+2 | 3 | 8.3 | a | 3 | 0.0 | a | 3 | 267.2 | a-c | 2 | 1.590 | d-e | 3 | 0.83 | e | 3 | 2.19 | b-c |
| 4+4 | 3 | 8.3 | a | 3 | 0.0 | a | 3 | 277.9 | a-b | 2 | 1.566 | d-e | 3 | 0.11 | e | 3 | 0.50 | e-f |
| 4+8 | 3 | 0.0 | a | 3 | 0.0 | a | 3 | 229.5 | b-e | 3 | 1.799 | a-d | 3 | 0.00 | e | 3 | 0.42 | e-f |
| 8+2 | 3 | 0.0 | a | 3 | 0.0 | a | 3 | 284.8 | a | 3 | 1.530 | e | 3 | 0.08 | e | 3 | 1.17 | d-e |
| 8+4 | 3 | 0.0 | a | 3 | 0.0 | a | 3 | 267.0 | a-c | 2 | 1.629 | d-e | 3 | 0.00 | e | 3 | 0.75 | d-f |
| 8+8 | 3 | 16.7 | a | 3 | 0.0 | a | 3 | 205.6 | e | 2 | 2.014 | a | 3 | 0.00 | e | 3 | 0.00 | f |

EXPERIMENT NO. 8
Statistical Analyses of Percent Mortality, Weight Gain, Feed/Gain, Intestinal and Cecal Lesion Scores of broiler cockerels inoculated with *E. maxima* and *E. tenella*

| Treatment PPM | Mortality Mean # | Total % | | # | % DTC | | Wt. Gain # | Mean | | Feed/Gain # | Mean | | Intestinal # | Mean | | Cecal # | Mean | |
|---|---|---|---|---|---|---|---|---|---|---|---|---|---|---|---|---|---|---|
| NC | | | | | | | | | | | | | | | | | | |
| 0 | 3 | 0.0 | a | 3 | 0.0 | b | 3 | 258.2 | a-b | 3 | 1.727 | b | 3 | 0.33 | d | 3 | 0.00 | d |
| IC | | | | | | | | | | | | | | | | | | |
| 0 | 3 | 25.0 | a | 3 | 25.0 | a | 3 | 162.7 | d | 1 | 2.379 | a | 3 | 8.58 | a | 3 | 3.08 | a-b |
| A82810 | | | | | | | | | | | | | | | | | | |
| 2 | 3 | 0.0 | a | 3 | 0.0 | b | 3 | 174.8 | c-d | 3 | 2.205 | a-b | 3 | 8.83 | a | 3 | 2.92 | a-b |
| 4 | 3 | 0.0 | a | 3 | 0.0 | b | 3 | 202.3 | a-d | 3 | 2.001 | a-b | 3 | 8.92 | a | 3 | 3.25 | a |
| 8 | 3 | 0.0 | a | 3 | 0.0 | b | 3 | 216.0 | a-d | 3 | 1.976 | a-b | 3 | 8.42 | a | 3 | 3.33 | a |
| Example No. 113 | | | | | | | | | | | | | | | | | | |
| 2 | 3 | 16.7 | a | 3 | 8.3 | b | 3 | 176.7 | c-d | 1 | 2.207 | a-b | 3 | 8.44 | a | 3 | 2.86 | a-b |
| 4 | 3 | 8.3 | a | 3 | 0.0 | b | 3 | 231.1 | a-d | 2 | 1.789 | a-b | 3 | 7.67 | a | 3 | 2.75 | a-b |
| 8 | 3 | 0.0 | a | 3 | 0.0 | b | 3 | 230.3 | a-d | 3 | 1.834 | a-b | 3 | 1.42 | c-d | 3 | 0.42 | c-d |
| A82810 + Example No. 113 | | | | | | | | | | | | | | | | | | |
| 2+2 | 3 | 0.0 | a | 3 | 0.0 | b | 3 | 246.1 | a-c | 3 | 1.711 | b | 3 | 8.17 | a | 3 | 3.08 | a-b |
| 2+4 | 3 | 8.3 | a | 3 | 0.0 | b | 3 | 243.0 | a-c | 2 | 1.743 | a-b | 3 | 1.42 | c-d | 3 | 1.31 | c |
| 2+8 | 3 | 8.3 | a | 3 | 0.0 | b | 3 | 220.9 | a-d | 2 | 1.791 | a-b | 3 | 0.00 | d | 3 | 0.17 | d |
| 4+2 | 3 | 0.0 | a | 3 | 0.0 | b | 3 | 276.3 | a | 3 | 1.636 | b | 3 | 5.25 | b | 3 | 2.08 | b |
| 4+4 | 3 | 0.0 | a | 3 | 0.0 | b | 3 | 258.8 | a-b | 3 | 1.668 | b | 3 | 0.58 | d | 3 | 0.92 | c-d |
| 4+8 | 3 | 0.0 | a | 3 | 0.0 | b | 3 | 232.0 | a-d | 3 | 1.776 | a-b | 3 | 0.33 | d | 3 | 0.17 | d |
| 8+2 | 3 | 0.0 | a | 3 | 0.0 | b | 3 | 258.9 | a-b | 3 | 1.707 | b | 3 | 3.17 | c | 3 | 1.08 | c-d |
| 8+4 | 3 | 0.0 | a | 3 | 0.0 | b | 3 | 259.3 | a-b | 3 | 1.634 | b | 3 | 0.00 | d | 3 | 0.00 | d |
| 8+8 | 3 | 0.0 | a | 3 | 0.0 | b | 3 | 192.9 | b-d | 3 | 2.100 | a-b | 3 | 0.42 | d | 3 | 0.00 | d |

EXPERIMENT NO. 9
Statistical Analyses of Percent Mortality, Weight Gain, Feed/Gain,
Intestinal and Cecal Lesion Scores of broiler cockerels inoculated with
*E. tenella* and *E. acervulina*

| Treatment | Mortality Mean | | | | Wt. Gain | | Feed/Gain | | Lesion Scores Intestinal | | Cecal | | | | | |
|---|---|---|---|---|---|---|---|---|---|---|---|---|---|---|---|---|
| PPM | # | Total % | | # | % DTC | | # | Mean | | # | Mean | | # | Mean | | # | Mean | |
| NC | | | | | | | | | | | | | | | | | |
| 0 | 3 | 8.3 | b | 3 | 0.0 | b | 3 | 323.5 | a | 2 | 1.410 | c | 3 | 0.00 | b | 3 | 0.00 | f |
| IC | | | | | | | | | | | | | | | | | |
| 0 | 3 | 16.7 | b | 3 | 16.7 | a | 3 | 248.1 | b–d | 1 | 1.927 | a–b | 3 | 7.25 | a | 3 | 3.75 | a |
| A82810 + Example No. 23 | | | | | | | | | | | | | | | | | |
| 2+2 | 3 | 0.0 | b | 3 | 0.0 | b | 3 | 265.0 | a–d | 3 | 1.714 | a–c | 3 | 0.75 | b | 3 | 3.42 | a |
| 2+4 | 3 | 0.0 | b | 3 | 0.0 | b | 3 | 257.9 | b–d | 3 | 1.622 | b–c | 3 | 0.17 | b | 3 | 2.00 | b–c |
| 2+8 | 3 | 0.0 | b | 3 | 0.0 | b | 3 | 252.2 | b–d | 3 | 1.691 | a–c | 3 | 0.00 | b | 3 | 0.58 | e–f |
| 4+2 | 3 | 8.3 | b | 3 | 8.3 | b | 3 | 292.5 | a–c | 2 | 1.482 | b–c | 3 | 0.00 | b | 3 | 1.83 | b–d |
| 4+4 | 3 | 0.0 | b | 3 | 0.0 | b | 3 | 290.2 | a–c | 3 | 1.566 | b–c | 3 | 0.00 | b | 3 | 1.42 | c–f |
| 4+8 | 3 | 0.0 | b | 3 | 0.0 | b | 3 | 265.3 | a–d | 3 | 1.623 | b–c | 3 | 0.00 | b | 3 | 0.42 | f |
| 8+2 | 3 | 0.0 | b | 3 | 0.0 | b | 3 | 300.8 | a–b | 3 | 1.555 | b–c | 3 | 0.00 | b | 3 | 0.00 | f |
| 8+4 | 3 | 0.0 | b | 3 | 0.0 | b | 3 | 292.3 | a–c | 3 | 1.565 | b–c | 3 | 0.00 | b | 3 | 0.25 | f |
| 8+8 | 3 | 0.0 | b | 3 | 0.0 | b | 3 | 244.3 | b–d | 3 | 1.772 | a–c | 3 | 0.00 | b | 3 | 0.00 | f |
| A82810 + Example No. 39 | | | | | | | | | | | | | | | | | |
| 2+2 | 3 | 8.3 | b | 3 | 0.0 | b | 3 | 303.9 | a–b | 2 | 1.578 | b–c | 3 | 0.28 | b | 3 | 2.83 | a–b |
| 2+4 | 3 | 16.7 | b | 3 | 0.0 | b | 3 | 263.3 | a–d | 1 | 1.658 | a–c | 3 | 0.00 | b | 3 | 1.75 | b–e |
| 2+8 | 3 | 50.0 | a | 3 | 0.0 | b | 3 | 230.9 | c–d | | | | 3 | 0.00 | b | 3 | 0.22 | f |
| 4+2 | 3 | 0.0 | b | 3 | 0.0 | b | 3 | 280.3 | a–c | 3 | 1.554 | b–c | 3 | 0.00 | b | 3 | 1.08 | c–f |
| 4+4 | 3 | 8.3 | b | 3 | 0.0 | b | 3 | 275.5 | a–c | 2 | 1.644 | b–c | 3 | 0.00 | b | 3 | 0.72 | d–f |
| 4+8 | 3 | 16.7 | b | 3 | .0.0 | b | 3 | 212.2 | d | 2 | 2.025 | a | 3 | 0.00 | b | 3 | 0.00 | f |
| 8+2 | 3 | 8.3 | b | 3 | 0.0 | b | 3 | 283.0 | a–c | 2 | 1.572 | b–c | 3 | 0.00 | b | 3 | 0.00 | f |
| 8+4 | 3 | 16.7 | b | 3 | 0.0 | b | 3 | 273.8 | a–c | 1 | 1.804 | a–c | 3 | 0.00 | b | 3 | 0.19 | f |
| 8+8 | 3 | 0.0 | b | 3 | 0.0 | b | 3 | 233.3 | c–d | 3 | 1.851 | a–b | 3 | 0.00 | b | 3 | 0.00 | f |

EXPERIMENT NO. 10
Statistical Analyses of Percent Mortality, Weight Gain, Feed/Gain,
Intestinal and Cecal Lesion Scores of broiler cockerels inoculated with
*E. tenella* and *E. maxima*

| Treatment | Mortality Mean | | | | Wt. Gain | | Feed/Gain | | Lesion Scores Intestinal | | Cecal | | | | | |
|---|---|---|---|---|---|---|---|---|---|---|---|---|---|---|---|---|
| PPM | # | Total % | | # | % DTC | | # | Mean | | # | Mean | | # | Mean | | # | Mean | |
| NC | | | | | | | | | | | | | | | | | |
| 0 | 3 | 0.0 | a | 3 | 0.0 | b | 3 | 317.3 | a | 3 | 1.487 | c–d | 3 | 0.42 | b | 3 | 0.00 | e |
| IC | | | | | | | | | | | | | | | | | |
| 0 | 3 | 16.7 | a | 3 | 16.7 | a | 3 | 246.0 | c–e | 1 | 1.955 | a | 3 | 5.50 | a | 3 | 3.83 | a |
| A82810 + Example No. 23 | | | | | | | | | | | | | | | | | |
| 2+2 | 3 | 0.0 | a | 3 | 0.0 | b | 3 | 302.6 | a–c | 3 | 1.547 | c–d | 3 | 1.33 | b | 3 | 2.58 | b |
| 2+4 | 3 | 0.0 | a | 3 | 0.0 | b | 3 | 302.8 | a–c | 3 | 1.485 | c–d | 3 | 0.83 | b | 3 | 2.00 | b–c |
| 2+8 | 3 | 0.0 | a | 3 | 0.0 | b | 3 | 262.5 | a–d | 3 | 1.641 | a–d | 3 | 0.42 | b | 3 | 0.83 | c–e |
| 4+2 | 3 | 0.0 | a | 3 | 0.0 | b | 3 | 307.1 | a–c | 3 | 1.456 | d | 3 | 0.83 | b | 3 | 1.58 | c–d |
| 4+4 | 3 | 0.0 | a | 3 | 0.0 | b | 3 | 304.1 | a–c | 3 | 1.560 | c–d | 3 | 0.83 | b | 3 | 0.42 | d–e |
| 4+8 | 3 | 0.0 | a | 3 | 0.0 | b | 3 | 263.2 | a–d | 3 | 1.640 | a–d | 3 | 0.08 | b | 3 | 0.25 | e |
| 8+2 | 3 | 8.3 | a | 3 | 0.0 | b | 3 | 301.1 | a–c | 3 | 1.480 | c–d | 3 | 0.00 | b | 3 | 0.00 | e |
| 8+4 | 3 | 0.0 | a | 3 | 0.0 | b | 3 | 286.3 | a–c | 3 | 1.606 | b–d | 3 | 0.33 | b | 3 | 0.00 | e |
| 8+8 | 3 | 8.3 | a | 3 | 0.0 | b | 3 | 252.4 | b–e | 2 | 1.766 | a–c | 3 | 0.00 | b | 3 | 0.00 | e |
| A82810 + Example No. 39 | | | | | | | | | | | | | | | | | |
| 2+2 | 3 | 8.3 | a | 3 | 0.0 | b | 3 | 292.1 | a–c | 2 | 1.512 | c–d | 3 | 4.19 | a | 3 | 3.42 | a |
| 2+4 | 3 | 8.3 | a | 3 | 0.0 | b | 3 | 267.8 | a–d | 2 | 1.657 | a–d | 3 | 1.61 | b | 3 | 1.19 | c–e |
| 2+8 | 3 | 25.0 | a | 3 | 0.0 | b | 3 | 221.5 | d–f | | | | 3 | 1.67 | b | 3 | 1.00 | c–e |
| 4+2 | 3 | 0.0 | a | 3 | 0.0 | b | 3 | 271.3 | a–d | 3 | 1.651 | a–d | 3 | 0.42 | b | 3 | 1.00 | c–e |
| 4+4 | 3 | 25.0 | a | 3 | 0.0 | b | 3 | 257.4 | a–e | 2 | 1.624 | a–d | 3 | 0.25 | b | 3 | 1.00 | c–e |
| 4+8 | 3 | 41.7 | a | 3 | 0.0 | b | 3 | 186.9 | f | 1 | 1.888 | a–b | 3 | 0.33 | b | 3 | 0.33 | e |
| 8+2 | 3 | 0.0 | a | 3 | 0.0 | b | 3 | 312.1 | a–b | 3 | 1.532 | c–d | 3 | 0.17 | b | 3 | 0.00 | e |
| 8+4 | 3 | 25.0 | a | 3 | 0.0 | b | 3 | 275.1 | a–d | 1 | 1.616 | a–d | 3 | 0.33 | b | 3 | 0.44 | d–e |
| 8+8 | 3 | 25.0 | a | 3 | 0.0 | b | 3 | 207.1 | e–f | 1 | 1.952 | a | 3 | 0.17 | b | 3 | 0.08 | e |

EXPERIMENT NO. 11
Statistical Analyses of Percent Mortality, Weight Gain, Feed/Gain,
Intestinal and Cecal Lesion Scores of broiler cockerels inoculated with
*E. tenella* and *E. acervulina*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 3 | 8.3 a | 3 | 0.0 a | 3 | 298.0 a–b | 2 | 1.427 d | 3 | 0.00 b | 3 | 0.00 b |
| IC | | | | | | | | | | | | |
| 0 | 3 | 0.0 a | 3 | 0.0 a | 3 | 249.6 b–e | 3 | 1.706 a–d | 3 | 5.25 a | 3 | 3.33 a |
| A82810 + Example No. 113 | | | | | | | | | | | | |
| 2+2 | 3 | 8.3 a | 3 | 0.0 a | 3 | 309.8 a | 2 | 1.456 c–d | 3 | 0.00 b | 3 | 0.58 b |
| 2+4 | 3 | 0.0 a | 3 | 0.0 a | 3 | 283.9 a–c | 3 | 1.585 b–d | 3 | 0.00 b | 3 | 0.00 b |
| 2+8 | 3 | 0.0 a | 3 | 0.0 a | 3 | 235.2 c–e | 3 | 1.787 a–b | 3 | 0.00 b | 3 | 0.00 b |
| 4+2 | 3 | 0.0 a | 3 | 0.0 a | 3 | 287.3 a–b | 3 | 1.496 b–d | 3 | 0.00 b | 3 | 0.00 b |
| 4+4 | 3 | 8.3 a | 3 | 0.0 a | 3 | 286.4 a–c | 2 | 1.557 b–d | 3 | 0.00 b | 3 | 0.00 b |
| 4+8 | 3 | 25.0 a | 3 | 0.0 a | 3 | 246.3 b–e | 2 | 1.703 a–d | 3 | 0.00 b | 3 | 0.00 b |
| 8+2 | 3 | 0.0 a | 3 | 0.0 a | 3 | 252.7 b–e | 3 | 1.630 b–d | 3 | 0.00 b | 3 | 0.00 b |
| 8+4 | 3 | 0.0 a | 3 | 0.0 a | 3 | 273.8 a–d | 3 | 1.559 b–d | 3 | 0.00 b | 3 | 0.00 b |
| 8+8 | 3 | 0.0 a | 3 | 0.0 a | 3 | 222.7 e | 3 | 1.736 a–d | 3 | 0.00 b | 3 | 0.00 b |
| A82810 + Example No. 39 | | | | | | | | | | | | |
| 2+2 | 3 | 8.3 a | 3 | 0.0 a | 3 | 308.4 a | 2 | 1.487 b–d | 3 | 0.00 b | 3 | 0.22 b |
| 2+4 | 3 | 8.3 a | 3 | 0.0 a | 3 | 255.2 b–e | 2 | 1.630 b–d | 3 | 0.00 b | 3 | 0.00 b |
| 2+8 | 3 | 8.3 a | 3 | 0.0 a | 3 | 213.1 e | 2 | 1.973 a | 3 | 0.00 b | 3 | 0.22 b |
| 4+2 | 3 | 0.0 a | 3 | 0.0 a | 3 | 281.3 a–c | 3 | 1.556 b–d | 3 | 0.00 b | 3 | 0.00 b |
| 4+4 | 3 | 8.3 a | 3 | 0.0 a | 3 | 274.9 a–d | 2 | 1.610 b–d | 3 | 0.00 b | 3 | 0.00 b |
| 4+8 | 3 | 0.0 a | 3 | 0.0 a | 3 | 230.2 d–e | 3 | 1.767 a–c | 3 | 0.00 b | 3 | 0.00 b |
| 8+2 | 3 | 0.0 a | 3 | 0.0 a | 3 | 280.8 a–c | 3 | 1.589 b–d | 3 | 0.00 b | 3 | 0.00 b |
| 8+4 | 3 | 0.0 a | 3 | 0.0 a | 3 | 275.9 a–d | 3 | 1.592 b–d | 3 | 0.00 b | 3 | 0.00 b |
| 8+8 | 3 | 8.3 a | 3 | 0.0 a | 3 | 213.9 e | 2 | 1.954 a | 3 | 0.00 b | 3 | 0.00 b |

EXPERIMENT NO. 12
Statistical Analyses of Percent Mortality, Weight Gain, Feed/Gain,
Intestinal and Cecal Lesion Scores of broiler cockerels inoculated with
*E. tenella* and *E. maxima*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 3 | 0.0 b | 3 | 0.0 b | 3 | 304.0 a–b | 3 | 1.463 c–d | 3 | 0.00 b | 3 | 0.00 c |
| IC | | | | | | | | | | | | |
| 0 | 3 | 33.3 a | 3 | 33.3 a | 3 | 161.9 f | | | 3 | 7.75 a | 3 | 3.67 a |
| A82810 + Example No. 113 | | | | | | | | | | | | |
| 2+2 | 3 | 0.0 b | 3 | 0.0 b | 3 | 289.5 a–c | 3 | 1.569 b–d | 3 | 0.75 b | 3 | 0.33 c |
| 2+4 | 3 | 0.0 b | 3 | 0.0 b | 3 | 300.6 a–b | 3 | 1.451 d | 3 | 0.00 b | 3 | 0.00 c |
| 2+8 | 3 | 0.0 b | 3 | 0.0 b | 3 | 254.5 b–d | 3 | 1.650 b–d | 3 | 0.00 b | 3 | 0.00 c |
| 4+2 | 3 | 0.0 b | 3 | 0.0 b | 3 | 291.4 a–c | 3 | 1.481 c–d | 3 | 0.00 b | 3 | 0.00 c |
| 4+4 | 3 | 0.0 b | 3 | 0.0 b | 3 | 292.4 a–c | 3 | 1.501 b–d | 3 | 0.00 b | 3 | 0.00 c |
| 4+8 | 3 | 0.0 b | 3 | 0.0 b | 3 | 258.3 b–d | 3 | 1.628 b–d | 3 | 0.00 b | 3 | 0.00 c |
| 8+2 | 3 | 0.0 b | 3 | 0.0 b | 3 | 291.7 a–c | 3 | 1.506 b–d | 3 | 0.17 b | 3 | 0.00 c |
| 8+4 | 3 | 0.0 b | 3 | 0.0 b | 3 | 276.1 a–c | 3 | 1.555 b–d | 3 | 0.00 b | 3 | 0.00 c |
| 8+8 | 3 | 0.0 b | 3 | 0.0 b | 3 | 253.5 b–d | 3 | 1.660 b–c | 3 | 0.00 b | 3 | 0.00 c |
| A82810 + Example No. 39 | | | | | | | | | | | | |
| 2+2 | 3 | 8.3 b | 3 | 0.0 b | 3 | 276.6 a–c | 2 | 1.596 b–d | 3 | 0.56 b | 3 | 0.72 b |
| 2+4 | 3 | 8.3 b | 3 | 0.0 b | 3 | 279.4 a–c | 2 | 1.548 b–d | 3 | 0.00 b | 3 | 0.00 c |
| 2+8 | 3 | 8.3 b | 3 | 0.0 b | 3 | 228.2 d–e | 2 | 1.891 a | 3 | 0.00 b | 3 | 0.00 c |
| 4+2 | 3 | 0.0 b | 3 | 0.0 b | 3 | 310.9 a | 3 | 1.462 c–d | 3 | 0.00 b | 3 | 0.00 c |
| 4+4 | 3 | 0.0 b | 3 | 0.0 b | 3 | 276.8 a–c | 3 | 1.554 b–d | 3 | 0.00 b | 3 | 0.00 c |
| 4+8 | 3 | 0.0 b | 3 | 0.0 b | 3 | 245.5 c–e | 3 | 1.723 b | 3 | 0.00 b | 3 | 0.00 c |
| 8+2 | 3 | 0.0 b | 3 | 0.0 b | 3 | 284.5 a–c | 3 | 1.540 b–d | 3 | 0.00 b | 3 | 0.00 c |
| 8+4 | 3 | 8.3 b | 3 | 0.0 b | 3 | 277.6 a–c | 2 | 1.565 b–d | 3 | 0.00 b | 3 | 0.00 c |
| 8+8 | 3 | 16.7 b | 3 | 0.0 b | 3 | 213.1 e | 1 | 1.782 a–b | 3 | 0.00 b | 3 | 0.00 c |

EXPERIMENT NO. 13
Statistical Analyses of Percent Mortality, Weight Gain, Feed/Gain, Intestinal and Cecal Lesion Scores of broiler cockerels inoculated with *E. tenella* and *E. acervulina*

| Treatment | | Mortality Mean | | | | | Wt. Gain | | | Feed/Gain | | | Lesion Scores Intestinal | | | Cecal | |
|---|---|---|---|---|---|---|---|---|---|---|---|---|---|---|---|---|---|
| PPM | # | Total % | | # | % DTC | | # | Mean | | # | Mean | | # | Mean | | # | Mean |
| NC | | | | | | | | | | | | | | | | | |
| 0 | 3 | 8.3 | a | 3 | 0.0 | a | 3 | 330.7 | a | 2 | 1.448 | d | 3 | 0.00 | f | 3 | 0.00 | c |
| IC | | | | | | | | | | | | | | | | | |
| 0 | 3 | 0.0 | a | 3 | 0.0 | a | 3 | 250.5 | d | 3 | 1.847 | a | 3 | 7.25 | a | 3 | 3.67 | a |
| SALINOMYCIN | | | | | | | | | | | | | | | | | |
| 8 | 3 | 0.0 | a | 3 | 0.0 | a | 3 | 254.7 | c–d | 3 | 1.752 | a–c | 3 | 5.33 | a–c | 3 | 3.08 | a–b |
| 16 | 3 | 8.3 | a | 3 | 0.0 | a | 3 | 279.6 | b–d | 2 | 1.620 | a–d | 3 | 2.97 | c–f | 3 | 3.72 | a |
| 32 | 3 | 0.0 | a | 3 | 0.0 | a | 3 | 287.0 | b–d | 3 | 1.604 | b–d | 3 | 1.83 | d–f | 3 | 3.25 | a–b |
| Example No. 39 | | | | | | | | | | | | | | | | | |
| 1 | 3 | 0.0 | a | 3 | 0.0 | a | 3 | 263.3 | b–d | 3 | 1.742 | a–c | 3 | 7.25 | a | 3 | 3.75 | a |
| 3 | 3 | 0.0 | a | 3 | 0.0 | a | 3 | 247.0 | d | 3 | 1.851 | a | 3 | 6.17 | a–b | 3 | 3.08 | a–b |
| 5 | 3 | 0.0 | a | 3 | 0.0 | a | 3 | 245.3 | d | 3 | 1.791 | a–b | 3 | 3.92 | b–e | 3 | 3.50 | a |
| SALINOMYCIN + Example 39 | | | | | | | | | | | | | | | | | |
| 8+1 | 3 | 0.0 | a | 3 | 0.0 | a | 3 | 270.3 | b–d | 3 | 1.706 | a–d | 3 | 4.42 | b–d | 3 | 3.75 | a |
| 8+3 | 3 | 8.3 | a | 3 | 0.0 | a | 3 | 275.2 | b–d | 2 | 1.713 | a–d | 3 | 2.86 | c–f | 3 | 3.19 | a–b |
| 8+5 | 3 | 0.0 | a | 3 | 0.0 | a | 3 | 266.1 | b–d | 3 | 1.684 | a–d | 3 | 2.00 | d–f | 3 | 2.83 | a–b |
| 16+1 | 3 | 8.3 | a | 3 | 0.0 | a | 3 | 273.1 | b–d | 2 | 1.684 | a–d | 3 | 2.53 | c–f | 3 | 3.83 | a |
| 16+3 | 3 | 0.0 | a | 3 | 0.0 | a | 3 | 284.8 | b–d | 3 | 1.599 | b–d | 3 | 1.25 | e–f | 3 | 3.33 | a |
| 16+5 | 3 | 0.0 | a | 3 | 0.0 | a | 3 | 295.8 | a–c | 3 | 1.559 | b–d | 3 | 1.00 | e–f | 3 | 2.92 | a–b |
| 32+1 | 3 | 8.3 | a | 3 | 0.0 | a | 3 | 296.7 | a–c | 2 | 1.536 | c–d | 3 | 1.14 | e–f | 3 | 2.67 | a–b |
| 32+3 | 3 | 0.0 | a | 3 | 0.0 | a | 3 | 303.6 | a–b | 3 | 1.535 | c–d | 3 | 0.75 | e–f | 3 | 1.83 | b |
| 32+5 | 3 | 0.0 | a | 3 | 0.0 | a | 3 | 298.5 | a–c | 3 | 1.568 | b–d | 3 | 0.42 | f | 3 | 0.25 | c |

EXPERIMENT NO. 14
Statistical Analyses of Percent Mortality, Weight Gain, Feed/Gain, Intestinal and Cecal Lesion Scores of broiler cockerels inoculated with *E. acervulina* and *E. tenella*

| Treatment | | Mortality Mean | | | | | Wt. Gain | | | Feed/Gain | | | Lesion Scores Intestinal | | | Cecal | |
|---|---|---|---|---|---|---|---|---|---|---|---|---|---|---|---|---|---|
| PPM | # | Total % | | # | % DTC | | # | Mean | | # | Mean | | # | Mean | | # | Mean |
| NC | | | | | | | | | | | | | | | | | |
| 0 | 3 | 0.0 | a | 3 | 0.0 | a | 3 | 319.9 | a | 3 | 1.403 | c | 3 | 0.00 | d | 3 | 0.00 | e |
| IC | | | | | | | | | | | | | | | | | |
| 0 | 3 | 0.0 | a | 3 | 0.0 | a | 3 | 227.6 | d | 3 | 1.837 | a | 3 | 7.50 | a | 3 | 2.92 | a |
| A82810 + Example No. 57 | | | | | | | | | | | | | | | | | |
| 2+2 | 3 | 0.0 | a | 3 | 0.0 | a | 3 | 262.3 | b–d | 3 | 1.622 | b–c | 3 | 4.75 | b | 3 | 2.83 | a |
| 2+4 | 3 | 16.7 | a | 3 | 0.0 | a | 3 | 251.8 | c–d | 2 | 1.609 | b–c | 3 | 1.33 | c–d | 3 | 1.58 | b–c |
| 2+8 | 3 | 0.0 | a | 3 | 0.0 | a | 3 | 274.6 | a–d | 3 | 1.552 | b–c | 3 | 0.00 | d | 3 | 0.75 | c–e |
| 4+2 | 3 | 0.0 | a | 3 | 0.0 | a | 3 | 288.7 | a–c | 3 | 1.473 | b–c | 3 | 0.83 | c–d | 3 | 1.42 | b–d |
| 4+4 | 3 | 0.0 | a | 3 | 0.0 | a | 3 | 278.9 | a–c | 3 | 1.486 | b–c | 3 | 0.33 | d | 3 | 1.50 | b–c |
| 4+8 | 3 | 8.3 | a | 3 | 0.0 | a | 3 | 279.3 | a–c | 3 | 1.573 | b–c | 3 | 0.00 | d | 3 | 0.25 | d–e |
| 8+2 | 3 | 0.0 | a | 3 | 0.0 | a | 3 | 304.1 | a–c | 3 | 1.419 | c | 3 | 0.00 | d | 3 | 0.17 | d–e |
| 8+4 | 3 | 0.0 | a | 3 | 0.0 | a | 3 | 289.2 | a–c | 3 | 1.483 | b–c | 3 | 0.00 | d | 3 | 0.17 | d–e |
| 8+8 | 3 | 25.0 | a | 3 | 0.0 | a | 3 | 269.2 | a–d | 1 | 1.541 | b–c | 3 | 0.00 | d | 3 | 0.00 | e |
| A82810 + Example No. 56 | | | | | | | | | | | | | | | | | |
| 2+2 | 3 | 0.0 | a | 3 | 0.0 | a | 3 | 252.2 | c–d | 3 | 1.667 | b | 3 | 5.00 | b | 3 | 3.25 | a |
| 2+4 | 3 | 0.0 | a | 3 | 0.0 | a | 3 | 284.3 | a–c | 3 | 1.541 | b–c | 3 | 2.33 | c | 3 | 2.33 | ab–b |
| 2+8 | 3 | 0.0 | a | 3 | 0.0 | a | 3 | 264.8 | b–d | 3 | 1.587 | b–c | 3 | 0.42 | d | 3 | 1.00 | c–e |
| 4+2 | 3 | 0.0 | a | 3 | 0.0 | a | 3 | 312.1 | a–b | 3 | 1.447 | b–c | 3 | 0.75 | c–d | 3 | 0.67 | c–e |
| 4+4 | 3 | 0.0 | a | 3 | 0.0 | a | 3 | 295.0 | a–c | 3 | 1.460 | b–c | 3 | 0.33 | d | 3 | 1.25 | b–e |
| 4+8 | 3 | 0.0 | a | 3 | 0.0 | a | 3 | 286.3 | a–c | 3 | 1.536 | b–c | 3 | 0.00 | d | 3 | 0.58 | c–e |
| 8+2 | 3 | 0.0 | a | 3 | 0.0 | a | 3 | 296.8 | a–c | 3 | 1.477 | b–c | 3 | 0.00 | d | 3 | 0.25 | d–e |
| 8+4 | 3 | 0.0 | a | 3 | 0.0 | a | 3 | 294.8 | a–c | 3 | 1.530 | b–c | 3 | 0.00 | d | 3 | 0.17 | d–e |
| 8+8 | 3 | 0.0 | a | 3 | 0.0 | a | 3 | 263.6 | b–d | 3 | 1.577 | b–c | 3 | 0.00 | d | 3 | 0.00 | e |

EXPERIMENT NO. 15
Statistical Analyses of Percent Mortality, Weight Gain, Feed/Gain,
Intestinal and Cecal Lesion Scores of broiler cockerels inoculated with
*E. maxima* and *E. tenella*

| Treatment | Mortality Mean | | | | | Wt. Gain | | Feed/Gain | | Lesion Scores | | | | |
|---|---|---|---|---|---|---|---|---|---|---|---|---|---|---|
| | | | | | | | | | | Intestinal | | | Cecal | |
| PPM | # | Total % | | # | % DTC | | # | Mean | # | Mean | # | Mean | # | Mean |
| NC | | | | | | | | | | | | | | |
| 0 | 3 | 0.0 | b | 3 | 0.0 | b | 3 | 300.7 a | 3 | 1.480 a | 3 | 0.00 b | 3 | 0.00 d |
| IC | | | | | | | | | | | | | | |
| 0 | 3 | 33.3 | a | 3 | 33.3 | a | 3 | 170.6 b | | | 3 | 8.17 a | 3 | 3.50 a |
| A82810 + Example No. 57 | | | | | | | | | | | | | | |
| 2+2 | 3 | 0.0 | b | 3 | 0.0 | b | 3 | 260.2 a | 3 | 1.617 a | 3 | 7.33 a | 3 | 2.92 a-b |
| 2+4 | 3 | 0.0 | b | 3 | 0.0 | b | 3 | 291.5 a | 3 | 1.484 a | 3 | 2.50 b | 3 | 1.50 c-d |
| 2+8 | 3 | 0.0 | b | 3 | 0.0 | b | 3 | 259.8 a | 3 | 1.621 a | 3 | 1.50 b | 3 | 1.08 c-d |
| 4+2 | 3 | 0.0 | b | 3 | 0.0 | b | 3 | 285.3 a | 3 | 1.575 a | 3 | 6.00 a | 3 | 2.25 b-c |
| 4+4 | 3 | 0.0 | b | 3 | 0.0 | b | 3 | 277.3 a | 3 | 1.501 a | 3 | 0.75 b | 3 | 0.42 d |
| 4+8 | 3 | 0.0 | b | 3 | 0.0 | b | 3 | 262.2 a | 3 | 1.576 a | 3 | 0.00 b | 3 | 0.00 d |
| 8+2 | 3 | 0.0 | b | 3 | 0.0 | b | 3 | 298.1 a | 3 | 1.424 a | 3 | 0.33 b | 3 | 0.08 d |
| 8+4 | 3 | 0.0 | b | 3 | 0.0 | b | 3 | 293.8 a | 3 | 1.474 a | 3 | 0.00 b | 3 | 0.00 d |
| 8+8 | 3 | 8.3 | b | 3 | 0.0 | b | 3 | 264.4 a | 2 | 1.514 a | 3 | 0.00 b | 3 | 0.00 d |
| A82810 + Example No. 56 | | | | | | | | | | | | | | |
| 2+2 | 3 | 0.0 | b | 3 | 0.0 | b | 3 | 259.8 a | 3 | 1.626 a | 3 | 8.67 a | 3 | 3.58 a |
| 2+4 | 3 | 16.7 | b | 3 | 0.0 | b | 3 | 300.2 a | 1 | 1.449 a | 3 | 3.56 b | 3 | 2.31 b-c |
| 2+8 | 3 | 0.0 | b | 3 | 0.0 | b | 3 | 289.1 a | 3 | 1.442 a | 3 | 0.00 b | 3 | 0.33 d |
| 4+2 | 3 | 0.0 | b | 3 | 0.0 | b | 3 | 282.5 a | 3 | 1.475 a | 3 | 7.42 a | 3 | 2.17 b-c |
| 4+4 | 3 | 0.0 | b | 3 | 0.0 | b | 3 | 302.9 a | 3 | 1.420 a | 3 | 0.75 b | 3 | 0.83 d |
| 4+8 | 3 | 0.0 | b | 3 | 0.0 | b | 3 | 286.3 a | 3 | 1.516 a | 3 | 1.50 b | 3 | 0.25 d |
| 8+2 | 3 | 8.3 | b | 3 | 0.0 | b | 3 | 298.6 a | 2 | 1.451 a | 3 | 0.00 b | 3 | 0.00 d |
| 8+4 | 3 | 0.0 | b | 3 | 0.0 | b | 3 | 293.2 a | 3 | 1.476 a | 3 | 0.00 b | 3 | 0.00 d |
| 8+8 | 3 | 0.0 | b | 3 | 0.0 | b | 3 | 279.2 a | 3 | 1.525 a | 3 | 0.00 b | 3 | 0.17 d |

EXPERIMENT NO. 16
Statistical Analyses of Percent Mortality, Weight Gain, Feed/Gain,
Intestinal and Cecal Lesion Scores of broiler cockerels inoculated with
*E. tenella* and *E. acervulina*

| Treatment | Mortality Mean | | | | | | Wt. Gain | | Feed/Gain | | Lesion Scores | | | | |
|---|---|---|---|---|---|---|---|---|---|---|---|---|---|---|---|
| | | | | | | | | | | | Intestinal | | Cecal | | |
| PPM | # | Total % | | # | % DTC | | # | Mean | # | Mean | # | Mean | | # | Mean |
| NC | | | | | | | | | | | | | | | |
| 0 | 3 | 0.0 | e | 3 | 0.0 | e | 3 | 299.3 a | 3 | 1.539 d | 3 | 0.00 c | | 3 | 0.00 e |
| IC | | | | | | | | | | | | | | | |
| 0 | 3 | 16.7 | a-e | 3 | 8.3 | a-e | 3 | 199.4 e-j | 1 | 2.069 a-d | 3 | 8.81 a | | 3 | 3.11 a-c |
| A204 | | | | | | | | | | | | | | | |
| 2 | 3 | 8.3 | a-e | 3 | 8.3 | a-e | 3 | 190.3 f-j | 2 | 2.427 a | 3 | 7.00 a-b | | 3 | 3.58 a |
| 4 | 3 | 0.0 | e | 3 | 0.0 | e | 3 | 215.1 c-i | 3 | 1.936 a-d | 3 | 8.00 a-b | | 3 | 3.58 a |
| 6 | 3 | 25.0 | a-c | 3 | 16.7 | a-d | 3 | 152.5 j | 1 | 2.215 a-b | 3 | 7.06 a-b | | 3 | 3.75 a |
| 8 | 3 | 8.3 | a-e | 3 | 8.3 | a-e | 3 | 181.6 h-j | 2 | 2.044 a-d | 3 | 7.58 a-b | | 3 | 3.50 a |
| Example No. 56 | | | | | | | | | | | | | | | |
| 2 | 3 | 33.3 | a | 3 | 25.0 | a-b | 3 | 178.0 i-j | | | 3 | 7.53 a-b | | 3 | 3.75 a |
| 4 | 3 | 8.3 | a-e | 3 | 0.0 | e | 3 | 175.0 i-j | 2 | 2.124 a-d | 3 | 6.83 a-b | | 3 | 3.36 a-b |
| 6 | 3 | 25.0 | a-c | 3 | 25.0 | a-b | 3 | 206.7 d-i | 1 | 2.110 a-d | 3 | 6.33 a-b | | 3 | 3.67 a |
| 8 | 3 | 16.7 | a-e | 3 | 16.7 | a-d | 3 | 200.6 e-j | 1 | 2.095 a-d | 3 | 1.75 c | | 3 | 3.75 a |
| A204 + Example No. 56 | | | | | | | | | | | | | | | |
| 2+2 | 3 | 8.3 | a-e | 3 | 0.0 | e | 3 | 188.1 g-j | 2 | 2.128 a-d | 3 | 8.06 a-b | | 3 | 3.36 a-b |
| 2+4 | 3 | 0.0 | e | 3 | 0.0 | e | 3 | 222.4 b-i | 3 | 2.003 a-d | 3 | 7.17 a-b | | 3 | 3.42 a-b |
| 2+6 | 3 | 16.7 | a-e | 3 | 0.0 | e | 3 | 216.2 c-i | 1 | 2.172 a-c | 3 | 6.31 a-b | | 3 | 3.61 a |
| 2+8 | 3 | 0.0 | e | 3 | 0.0 | e | 3 | 240.9 b-g | 3 | 1.834 a-d | 3 | 0.00 c | | 3 | 2.42 a-d |
| 4+2 | 3 | 16.7 | a-e | 3 | 8.3 | a-e | 3 | 184.8 h-j | 3 | 2.056 a-d | 3 | 7.42 a-b | | 3 | 3.72 a |
| 4+4 | 3 | 0.0 | e | 3 | 0.0 | e | 3 | 233.4 b-h | 3 | 1.855 a-d | 3 | 5.92 a-b | | 3 | 3.92 a |
| 4+6 | 3 | 8.3 | a-e | 3 | 8.3 | a-e | 3 | 240.7 b-g | 2 | 2.050 a-d | 3 | 0.50 c | | 3 | 2.75 a-d |
| 4+8 | 3 | 0.0 | e | 3 | 0.0 | e | 3 | 25.38 a-e | 3 | 1.715 b-d | 3 | 0.00 c | | 3 | 1.75 b-d |
| 6+2 | 3 | 16.7 | a-e | 3 | 8.3 | a-e | 3 | 261.3 a-d | 2 | 1.764 a-d | 3 | 7.11 a-b | | 3 | 3.67 a |

-continued

| | | | | | | | | | | | | | | | | | |
|---|---|---|---|---|---|---|---|---|---|---|---|---|---|---|---|---|---|
| 6+4 | 3 | 8.3 | a–e | 3 | 8.3 | a–e | 3 | 247.8 | b–e | 2 | 1.874 | a–d | 3 | 1.25 | c | 3 | 2.67 | a–d |
| 6+6 | 3 | 0.0 | e | 3 | 0.0 | e | 3 | 263.8 | a–c | 3 | 1.716 | b–d | 3 | 0.00 | c | 3 | 1.25 | d–e |
| 6+8 | 3 | 0.0 | e | 3 | 0.0 | e | 3 | 262.5 | a–d | 3 | 1.734 | b–d | 3 | 0.00 | c | 3 | 1.25 | d–e |
| 8+2 | 3 | 8.3 | a–e | 3 | 0.0 | e | 3 | 244.7 | b–f | 2 | 1.927 | a–d | 3 | 3.78 | b–c | 3 | 3.36 | a–b |
| 8+4 | 3 | 8.3 | a–e | 3 | 0.0 | e | 3 | 271.4 | a–c | 2 | 1.812 | a–d | 3 | 2.50 | c | 3 | 3.25 | a–b |
| 8+6 | 3 | 0.0 | e | 3 | 0.0 | e | 3 | 273.8 | a–b | 3 | 1.623 | c–d | 3 | 0.00 | c | 3 | 1.67 | c–d |
| 8+8 | 3 | 0.0 | e | 3 | 0.0 | e | 3 | 240.4 | b–g | 3 | 1.924 | a–d | 3 | 0.00 | c | 3 | 1.17 | d–e |

EXPERIMENT NO. 17
Statistical Analyses of Percent Mortality, Weight Gain, Feed/Gain, Intestinal and Cecal Lesion Scores of broiler cockerels inoculated with *E. maxima* and *E. tenella*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 3 | 8.3 a–e | 3 | 0.0 e | 3 | 320.3 a | 2 | 1.463 e | 3 | 0.67 f | 3 | 0.17 f |
| IC | | | | | | | | | | | | |
| 0 | 3 | 8.3 a–e | 3 | 0.0 e | 3 | 205.9 d–e | 2 | 2.041 a–d | 3 | 8.72 a | 3 | 3.56 a–b |
| A204 | | | | | | | | | | | | |
| 2 | 3 | 0.0 e | 3 | 0.0 e | 3 | 184.3 e | 3 | 2.159 a–b | 3 | 9.08 a | 3 | 3.67 a–b |
| 4 | 3 | 8.3 a–e | 3 | 8.3 a–e | 3 | 225.5 b–e | 2 | 1.857 a–e | 3 | 8.17 a | 3 | 3.92 a |
| 6 | 3 | 8.3 a–e | 3 | 8.3 a–e | 3 | 220.1 c–e | 2 | 2.108 a–c | 3 | 7.75 a | 3 | 3.67 a–b |
| 8 | 3 | 0.0 e | 3 | 0.0 e | 3 | 255.1 a–d | 3 | 1.751 a–e | 3 | 9.00 a | 3 | 3.33 a–b |
| Example No. 56 | | | | | | | | | | | | |
| 2 | 3 | 0.0 e | 3 | 0.0 e | 3 | 207.8 d–e | 3 | 1.929 a–e | 3 | 8.83 a | 3 | 3.58 a–b |
| 4 | 3 | 8.3 a–e | 3 | 0.0 e | 3 | 206.3 d–e | 2 | 2.087 a–d | 3 | 8.58 a | 3 | 3.50 a–b |
| 6 | 3 | 0.0 e | 3 | 0.0 e | 3 | 203.1 d–e | 3 | 2.192 a | 3 | 8.42 a | 3 | 3.67 a–b |
| 8 | 3 | 0.0 e | 3 | 0.0 e | 3 | 232.8 b–e | 3 | 1.881 a–e | 3 | 6.83 a–b | 3 | 3.50 a–b |
| A204 + Example No. 56 | | | | | | | | | | | | |
| 2+2 | 3 | 0.0 e | 3 | 0.0 e | 3 | 235.0 b–e | 3 | 1.955 a–d | 3 | 8.67 a | 3 | 3.00 a–b |
| 2+4 | 3 | 0.0 e | 3 | 0.0 e | 3 | 250.7 b–e | 3 | 1.818 a–e | 3 | 8.50 a | 3 | 3.50 a–b |
| 2+6 | 3 | 8.3 a–e | 3 | 8.3 a–e | 3 | 255.3 a–d | 2 | 1.743 b–e | 3 | 6.50 a–c | 3 | 3.67 a–b |
| 2+8 | 3 | 0.0 e | 3 | 0.0 e | 3 | 246.3 b–e | 3 | 1.837 a–e | 3 | 3.17 d–f | 3 | 1.83 c–d |
| 4+2 | 3 | 8.3 a–e | 3 | 8.3 a–e | 3 | 236.7 b–e | 2 | 1.801 a–e | 3 | 8.17 a | 3 | 3.58 a–b |
| 4+4 | 3 | 0.0 e | 3 | .0 e | 3 | 268.0 a–d | 3 | 1.743 b–e | 3 | 7.92 a | 3 | 3.08 a–b |
| 4+6 | 3 | 0.0 e | 3 | 0.0 e | 3 | 269.4 a–d | 3 | 1.728 b–e | 3 | 4.08 b–e | 3 | 2.17 b–d |
| 4+8 | 3 | 0.0 e | 3 | 0.0 e | 3 | 266.0 a–d | 3 | 1.804 a–e | 3 | 1.08 e–f | 3 | 0.33 e–f |
| 6+2 | 3 | 0.0 e | 3 | 0.0 e | 3 | 247.5 b–e | 3 | 1.843 a–e | 3 | 7.58 a | 3 | 3.25 a–b |
| 6+4 | 3 | 8.3 a–e | 3 | 8.3 a–e | 3 | 281.1 a–c | 2 | 1.685 b–e | 3 | 4.33 b–e | 3 | 2.75 a–c |
| 6+6 | 3 | 0.0 e | 3 | 0.0 e | 3 | 297.8 a–b | 3 | 1.635 d–e | 3 | 1.58 e–f | 3 | 1.50 d–e |
| 6+8 | 3 | 0.0 e | 3 | 0.0 e | 3 | 273.3 a–d | 3 | 1.708 b–e | 3 | 0.50 f | 3 | 0.50 e–f |
| 8+2 | 3 | 0.0 e | 3 | 0.0 e | 3 | 268.0 a–d | 3 | 1.757 a–e | 3 | 5.92 a–d | 3 | 3.83 a |
| 8+4 | 3 | 0.0 e | 3 | 0.0 e | 3 | 281.8 a–c | 3 | 1.636 c–e | 3 | 3.42 c–f | 3 | 3.42 a–b |
| 8+6 | 3 | 8.3 a–e | 3 | 0.0 e | 3 | 274.6 a–d | 2 | 1.634 d–e | 3 | 0.00 f | 3 | 0.50 e–f |
| 8+8 | 3 | 0.0 e | 3 | 0.0 e | 3 | 267.4 a–d | 3 | 1.758 a–e | 3 | 0.00 f | 3 | 0.33 e–f |

EXPERIMENT NO. 18
Statistical Analyses of Percent Mortality, Weight Gain, Feed/Gain, Intestinal and Cecal Lesion Scores of broiler cockerels inoculated with *E. acervulina* and *E. tenella*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 3 | 0.0 e | 3 | 0.0 e | 3 | 308.7 a | 3 | 1.488 c | 3 | 0.00 g | 3 | 0.00 d |
| IC | | | | | | | | | | | | |
| 0 | 3 | 0.0 e | 3 | 0.0 e | 3 | 224.2 b–e | 3 | 1.956 a–c | 3 | 7.92 a–b | 3 | 3.67 a–b |
| NARASIN | | | | | | | | | | | | |
| 10 | 3 | 33.3 a | 3 | 33.3 a | 3 | 235.9 b–e | | | 3 | 7.17 a–c | 3 | 3.67 a–b |
| 20 | 3 | 16.7 a–e | 3 | 8.3 a–e | 3 | 194.3 d–e | 1 | 2.162 a–b | 3 | 6.03 a–e | 3 | 3.64 a–b |
| 30 | 3 | 25.0 a–c | 3 | 25.0 a–c | 3 | 208.6 c–e | 1 | 1.819 a–c | 3 | 4.67 b–f | 3 | 3.83 a–b |
| 40 | 3 | 16.7 a–e | 3 | 16.7 a–e | 3 | 218.5 b–e | 1 | 1.959 a–c | 3 | 4.50 b–f | 3 | 3.92 a |

-continued

| Example No. 56 | | | | | | | | | | | | | | | | | | |
|---|---|---|---|---|---|---|---|---|---|---|---|---|---|---|---|---|---|---|
| 2 | 3 | 16.7 | a-e | 3 | 16.7 | a-e | 3 | 188.3 | e | 1 | 2.049 | a-c | 3 | 8.58 | a | 3 | 3.75 | a-b |
| 4 | 3 | 25.0 | a-c | 3 | 25.0 | a-c | 3 | 219.3 | b-e | | | | 3 | 7.06 | a-d | 3 | 3.69 | a-b |
| 6 | 3 | 0.0 | e | 3 | 0.0 | e | 3 | 193.4 | d-e | 3 | 2.193 | a | 3 | 5.67 | a-e | 3 | 3.42 | a-b |
| 8 | 3 | 8.3 | a-e | 3 | 0.0 | e | 3 | 220.5 | b-e | 2 | 2.025 | a-c | 3 | 1.33 | f-g | 3 | 2.89 | a-b |
| NARASIN + Example No. 56 | | | | | | | | | | | | | | | | | | |
| 10+2 | 3 | 8.3 | a-e | 3 | 8.3 | a-e | 3 | 224.3 | b-e | 2 | 2.044 | a-c | 3 | 6.00 | a-e | 3 | 3.58 | a-b |
| 10+4 | 3 | 8.3 | a-e | 3 | 0.0 | e | 3 | 224.4 | b-e | 2 | 1.852 | a-c | 3 | 2.14 | e-g | 3 | 3.56 | a-b |
| 10+6 | 3 | 8.3 | a-e | 3 | 8.3 | a-e | 3 | 221.8 | b-e | 2 | 1.893 | a-c | 3 | 3.42 | c-g | 3 | 3.67 | a-b |
| 10+8 | 3 | 16.7 | a-e | 3 | 16.7 | a-e | 3 | 252.3 | b-d | 1 | 1.727 | a-c | 3 | 0.92 | f-g | 3 | 3.58 | a-b |
| 20+2 | 3 | 0.0 | e | 3 | 0.0 | e | 3 | 225.9 | b-e | 3 | 1.907 | a-c | 3 | 3.33 | c-g | 3 | 3.42 | a-b |
| 20+4 | 3 | 0.0 | e | 3 | 0.0 | e | 3 | 239.2 | b-e | 3 | 1.819 | a-c | 3 | 3.17 | d-g | 3 | 3.33 | a-b |
| 20+6 | 3 | 0.0 | e | 3 | 0.0 | e | 3 | 264.0 | a-c | 3 | 1.659 | b-c | 3 | 1.17 | f-g | 3 | 3.00 | a-b |
| 20+8 | 3 | 0.0 | e | 3 | 0.0 | e | 3 | 263.4 | a-c | 3 | 1.691 | b-c | 3 | 0.00 | g | 3 | 2.75 | b |
| 30+2 | 3 | 8.3 | a-e | 3 | 8.3 | a-e | 3 | 208.4 | c-e | 2 | 1.859 | a-c | 3 | 4.92 | a-f | 3 | 3.67 | a-b |
| 30+4 | 3 | 0.0 | e | 3 | 0.0 | e | 3 | 264.6 | a-c | 3 | 1.732 | a-c | 3 | 1.42 | f-g | 3 | 3.75 | a-b |
| 30+6 | 3 | 0.0 | e | 3 | 0.0 | e | 3 | 263.4 | a-c | 3 | 1.734 | a-c | 3 | 0.25 | g | 3 | 2.75 | b |
| 30+8 | 3 | 8.3 | a-e | 3 | 0.0 | e | 3 | 249.9 | b-d | 3 | 1.690 | b-c | 3 | 0.00 | g | 3 | 1.56 | c |
| 40+2 | 3 | 0.0 | e | 3 | 0.0 | e | 3 | 246.1 | b-e | 3 | 1.736 | a-c | 3 | 2.17 | e-g | 3 | 3.67 | a-b |
| 40+4 | 3 | 0.0 | e | 3 | 0.0 | e | 3 | 270.1 | a-b | 3 | 1.643 | b-c | 3 | 0.92 | f-g | 3 | 3.25 | a-b |
| 40+6 | 3 | 0.0 | e | 3 | 0.0 | e | 3 | 240.0 | b-e | 3 | 1.861 | a-c | 3 | 0.00 | g | 3 | 3.42 | a-b |
| 40+8 | 3 | 8.3 | a-e | 3 | 0.0 | e | 3 | 261.2 | a-c | 2 | 1.804 | a-c | 3 | 0.00 | g | 3 | 1.44 | c |

EXPERIMENT NO. 19
Statistical Analyses of Percent Mortality, Weight Gain, Feed/Gain,
Intestinal and Cecal Lesion Scores of broiler cockerels inoculated with
*E. maxima* and *E. tenella*

| Treatment | Mortality Mean | | | | | | Wt. Gain | | | Feed/Gain | | | Lesion Scores | | | | | |
|---|---|---|---|---|---|---|---|---|---|---|---|---|---|---|---|---|---|---|
| | | | | | | | | | | | | | Intestinal | | | Cecal | | |
| PPM | # | Total % | | # | % DTC | | # | Mean | | # | Mean | | # | Mean | | # | Mean | |
| NC | | | | | | | | | | | | | | | | | | |
| 0 | 3 | 0.0 | e | 3 | 0.0 | e | 3 | 313.9 | a | 3 | 1.422 | d | 3 | 0.00 | f | 3 | 0.00 | d |
| IC | | | | | | | | | | | | | | | | | | |
| 0 | 3 | 8.3 | a-e | 3 | 8.3 | a-e | 3 | 202.3 | c-e | 2 | 1.791 | a-d | 3 | 9.00 | a | 3 | 3.67 | a-b |
| NARASIN | | | | | | | | | | | | | | | | | | |
| 10 | 3 | 8.3 | a-e | 3 | 8.3 | a-e | 3 | 240.9 | a-e | 2 | 1.803 | a-d | 3 | 7.92 | a-b | 3 | 3.75 | a-b |
| 20 | 3 | 8.3 | a-e | 3 | 8.3 | a-e | 3 | 215.7 | b-e | 2 | 1.946 | a-c | 3 | 7.83 | a-b | 3 | 3.50 | a-b |
| 30 | 3 | 0.0 | e | 3 | 0.0 | e | 3 | 227.8 | b-e | 3 | 1.778 | b-d | 3 | 7.92 | a-b | 3 | 3.92 | a-b |
| 40 | 3 | 8.3 | a-e | 3 | 0.0 | e | 3 | 218.6 | b-e | 2 | 1.694 | b-d | 3 | 8.28 | a-b | 3 | 3.69 | a-b |
| Example No. 56 | | | | | | | | | | | | | | | | | | |
| 2 | 3 | 8.3 | a-e | 3 | 0.0 | e | 3 | 190.3 | d-e | 2 | 2.030 | a-b | 3 | 8.67 | a-b | 3 | 3.72 | a-b |
| 4 | 3 | 0.0 | e | 3 | 0.0 | e | 3 | 190.2 | e | 3 | 2.107 | a | 3 | 8.42 | a-b | 3 | 3.75 | a-b |
| 6 | 2 | 37.5 | a | 2 | 25.0 | a | 2 | 236.5 | a-e | | | | 2 | 8.88 | a-b | 2 | 3.88 | a-b |
| 8 | 3 | 0.0 | e | 3 | 0.0 | e | 3 | 224.0 | b-e | 3 | 1.922 | a-c | 3 | 8.00 | a-b | 3 | 3.83 | a-b |
| NARASIN + Example No. 56 | | | | | | | | | | | | | | | | | | |
| 10+2 | 3 | 16.7 | a-b | 3 | 8.3 | a-e | 3 | 206.9 | b-e | 2 | 1.987 | a-c | 3 | 9.00 | a | 3 | 3.92 | a-b |
| 10+4 | 3 | 0.0 | e | 3 | 0.0 | e | 3 | 244.0 | a-e | 3 | 1.699 | b-d | 3 | 6.83 | a-b | 3 | 3.50 | a-b |
| 10+6 | 3 | 8.3 | a-e | 3 | 8.3 | a-e | 3 | 250.6 | a-e | 2 | 1.704 | b-d | 3 | 5.25 | a-d | 3 | 3.92 | a-b |
| 10+8 | 3 | .0 | e | 3 | 0.0 | e | 3 | 232.8 | b-e | 3 | 1.772 | b-d | 3 | 4.17 | b-e | 3 | 2.75 | a-c |
| 20+2 | 3 | 8.3 | a-e | 3 | 0.0 | e | 3 | 203.5 | b-e | 2 | 1.783 | a-d | 3 | 8.92 | a | 3 | 3.83 | a-b |
| 20+4 | 3 | 8.3 | a-e | 3 | 0.0 | e | 3 | 268.1 | a-e | 2 | 1.623 | b-d | 3 | 6.78 | a-b | 3 | 3.64 | a-b |
| 20+6 | 3 | 0.0 | e | 3 | 0.0 | e | 3 | 267.2 | a-e | 3 | 1.615 | c-d | 3 | 4.17 | b-e | 3 | 3.50 | a-b |
| 20+8 | 3 | 8.3 | a-e | 3 | 0.0 | e | 3 | 258.1 | a-e | 2 | 1.801 | a-d | 3 | 1.17 | e-f | 3 | 2.56 | a-c |
| 30+2 | 3 | 8.3 | a-e | 3 | 0.0 | e | 3 | 229.6 | b-e | 2 | 1.746 | b-d | 3 | 8.72 | a-b | 3 | 3.75 | a-b |
| 30+4 | 3 | 0.0 | e | 3 | 0.0 | e | 3 | 267.9 | a-e | 3 | 1.601 | c-d | 3 | 6.42 | a-c | 3 | 3.75 | a-b |
| 30+6 | 3 | 0.0 | e | 3 | 0.0 | e | 3 | 270.9 | a-e | 3 | 1.612 | c-d | 3 | 2.00 | d-f | 3 | 2.83 | a-c |
| 30+8 | 3 | 8.3 | a-e | 3 | 8.3 | a-e | 3 | 278.4 | a-b | 2 | 1.570 | c-d | 3 | 0.92 | e-f | 3 | 2.17 | c |
| 40+2 | 3 | 8.3 | a-e | 3 | 0.0 | e | 3 | 268.0 | a-e | 2 | 1.616 | b-d | 3 | 5.42 | a-d | 3 | 3.39 | a-b |
| 40+4 | 3 | 0.0 | e | 3 | 0.0 | e | 3 | 265.5 | a-e | 3 | 1.547 | d | 3 | 3.00 | c-f | 3 | 3.25 | a-c |
| 40+6 | 3 | 0.0 | e | 3 | 0.0 | e | 3 | 276.0 | a-c | 3 | 1.621 | b-d | 3 | 0.00 | f | 3 | 2.42 | b-c |
| 40+8 | 3 | 8.3 | a-e | 3 | 0.0 | e | 3 | 271.1 | a-d | 2 | 1.580 | c-d | 3 | 0.00 | f | 3 | 0.67 | d |

EXPERIMENT NO. 20
Statistical Analyses of Percent Mortality, Weight Gain, Feed/Gain, Intestinal and Cecal Lesion Scores of broiler cockerels inoculated with *E. tenella* and *E. acervulina*

| Treatment | Mortality Mean | | | | Wt. Gain | | Feed/Gain | | Lesion Scores Intestinal | | Cecal | |
|---|---|---|---|---|---|---|---|---|---|---|---|---|
| PPM | # | Total % | # | % DTC | # | Mean | # | Mean | # | Mean | # | Mean |
| NC | | | | | | | | | | | | |
| 0 | 3 | 0.0 e | 3 | 0.0 e | 3 | 287.3 a | 3 | 1.598 d | 3 | 0.00 e | 3 | 0.00 e |
| IC | | | | | | | | | | | | |
| 0 | 3 | 8.3 a–e | 3 | 0.0 e | 3 | 216.7 c–e | 2 | 1.855 a–d | 3 | 5.42 a–c | 3 | 3.92 a–d |
| NARASIN | | | | | | | | | | | | |
| 10 | 3 | 16.7 a–c | 3 | 0.0 e | 3 | 221.0 b–e | 1 | 2.028 a | 3 | 4.28 a–d | 3 | 4.00 a–d |
| 20 | 3 | 8.3 a–e | 3 | 0.0 e | 3 | 234.3 a–e | 2 | 1.963 a–c | 3 | 2.83 a–e | 3 | 3.92 a–d |
| 30 | 3 | 8.3 a–e | 3 | 0.0 e | 3 | 250.4 a–d | 2 | 1.849 a–d | 3 | 2.86 a–e | 3 | 3.64 a–d |
| 40 | 3 | 0.0 e | 3 | 0.0 e | 3 | 219.5 b–e | 3 | 1.773 a–d | 3 | 1.42 d–e | 3 | 3.50 a–d |
| Example No. 56 | | | | | | | | | | | | |
| 2 | 3 | 25.0 a | 3 | 16.7 a | 3 | 213.1 e | | | 3 | 6.06 a | 3 | 3.92 a–d |
| 4 | 3 | 0.0 e | 3 | 0.0 e | 3 | 218.8 b–e | 3 | 2.014 a–b | 3 | 5.67 a–b | 3 | 4.00 a–d |
| 6 | 3 | 0.0 e | 3 | 0.0 e | 3 | 214.4 d–e | 3 | 1.969 a–c | 3 | 2.08 b–e | 3 | 3.83 a–d |
| 8 | 3 | 0.0 e | 3 | 0.0 e | 3 | 225.8 b–e | 3 | 1.990 a–c | 3 | 0.75 d–e | 3 | 3.17 b–d |
| NARASIN + Example No. 56 | | | | | | | | | | | | |
| 10+2 | 3 | 8.3 a–e | 3 | 0.0 e | 3 | 220.2 b–e | 2 | 1.954 a–c | 3 | 2.50 b–e | 3 | 4.00 a–d |
| 10+4 | 3 | 0.0 e | 3 | 0.0 e | 3 | 241.5 a–e | 3 | 1.850 a–d | 3 | 2.33 b–e | 3 | 3.67 a–d |
| 10+6 | 3 | 8.3 a–e | 3 | 8.3 a–c | 3 | 248.2 a–e | 2 | 1.808 a–d | 3 | 1.75 c–e | 3 | 4.00 a–d |
| 10+8 | 3 | 0.0 e | 3 | 0.0 e | 3 | 239.8 a–e | 3 | 1.862 a–d | 3 | 0.42 d–e | 3 | 2.92 d |
| 20+2 | 3 | 0.0 e | 3 | 0.0 e | 3 | 244.3 a–e | 3 | 1.905 as–d | 3 | 2.67 a–e | 3 | 3.58 a–d |
| 20+4 | 3 | 8.3 a–e | 3 | 0.0 e | 3 | 240.4 a–e | 2 | 1.923 a–d | 3 | 2.69 a–e | 3 | 3.78 a–d |
| 20+6 | 3 | 0.0 e | 3 | 0.0 e | 3 | 241.1 a–e | 3 | 1.824 a–d | 3 | 0.83 d–e | 3 | 3.75 a–d |
| 20+8 | 3 | 0.0 e | 3 | 0.0 e | 3 | 248.0 a–e | 3 | 1.775 a–d | 3 | 0.67 d–e | 3 | 3.83 a–d |
| 30+2 | 3 | 0.0 e | 3 | 0.0 e | 3 | 234.4 a–e | 3 | 1.777 a–d | 3 | 2.42 b–e | 3 | 3.42 a–d |
| 30+4 | 3 | 8.3 a–e | 3 | 0.0 e | 3 | 239.8 b–e | 2 | 1.702 c–d | 3 | 1.81 c–e | 3 | 3.92 a–d |
| 30+6 | 3 | 16.7 a–c | 3 | 8.3 a–c | 3 | 228.6 b–e | 1 | 1.894 a–d | 3 | 1.39 d–e | 3 | 3.92 a–d |
| 30+8 | 3 | 0.0 e | 3 | 0.0 e | 3 | 235.3 a–e | 3 | 1.837 a–d | 3 | 0.50 d–e | 3 | 3.08 c–d |
| 40+2 | 3 | 0.0 e | 3 | 0.0 e | 3 | 244.4 a–e | 3 | 1.750 a–d | 3 | 1.83 c–e | 3 | 3.67 a–d |
| 40+4 | 3 | 8.3 a–e | 3 | 0.0 e | 3 | 234.8 a–e | 2 | 1.887 a–d | 3 | 1.47 d–e | 3 | 3.92 a–d |
| 40+6 | 3 | 0.0 e | 3 | 0.0 e | 3 | 253.6 a–c | 3 | 1.723 a–d | 3 | 0.33 d–e | 3 | 3.67 a–d |
| 40+8 | 3 | 0.0 e | 3 | 0.0 e | 3 | 265.4 a–b | 3 | 1.715 b–d | 3 | 0.17 e | 3 | 3.58 a–d |

EXPERIMENT NO. 21
Statistical Analyses of Percent Mortality, Weight Gain, Feed/Gain, Intestinal and Cecal Lesion Scores of broiler cockerels inoculated with *E. maxima* and *E. tenella*

| Treatment | Mortality Mean | | | | Wt. Gain | | Feed/Gain | | Lesion Scores Intestinal | | Cecal | |
|---|---|---|---|---|---|---|---|---|---|---|---|---|
| PPM | # | Total % | # | % DTC | # | Mean | # | Mean | # | Mean | # | Mean |
| NC | | | | | | | | | | | | |
| 0 | 3 | 8.3 b–e | 3 | 0.0 e | 3 | 298.5 a | 2 | 1.460 c | 3 | 0.00 e | 3 | 0.00 e |
| IC | | | | | | | | | | | | |
| 0 | 3 | 25.0 a–d | 3 | 25.0 a–d | 3 | 138.8 d–e | | | 3 | 8.33 a–c | 3 | 3.75 a–c |
| NARASIN | | | | | | | | | | | | |
| 10 | 3 | 0.0 e | 3 | 0.0 e | 3 | 148.0 d–e | 3 | 2.458 b | 3 | 8.75 a–c | 3 | 3.75 a–c |
| 20 | 3 | 8.3 b–e | 3 | 0.0 e | 3 | 146.6 d–e | 2 | 2.283 b–c | 3 | 8.75 a–c | 3 | 3.64 a–c |
| 30 | 3 | 16.7 b–e | 3 | 16.7 a–e | 3 | 158.2 c–e | 1 | 2.618 b | 3 | 8.08 a–c | 3 | 3.67 a–c |
| 40 | 3 | 16.7 b–e | 3 | 16.7 a–e | 3 | 182.1 b–e | 1 | 2.137 b–c | 3 | 8.08 a–c | 3 | 3.58 a–c |
| Example No. 56 | | | | | | | | | | | | |
| 2 | 3 | 8.3 b–e | 3 | 0.0 e | 3 | 122.9 e | 2 | 3.397 a | 3 | 8.17 a–c | 3 | 3.92 a–c |
| 4 | 3 | 25.0 a–d | 3 | 25.0 a–d | 3 | 135.6 d–e | 1 | 2.095 b–c | 3 | 8.92 a–c | 3 | 3.83 a–c |
| 6 | 3 | 8.3 b–e | 3 | 8.3 a–e | 3 | 135.1 d–e | 2 | 2.570 b | 3 | 9.00 a | 3 | 3.75 a–c |
| 8 | 3 | 0.0 e | 3 | 0.0 e | 3 | 200.8 b–e | 3 | 2.071 b–c | 3 | 8.92 a–c | 3 | 3.58 a–c |

| | | | | | | | | | | | | | | | | | |
|---|---|---|---|---|---|---|---|---|---|---|---|---|---|---|---|---|---|
| NARASIN + Example No. 56 | | | | | | | | | | | | | | | | | |
| 10+2 | 3 | 25.0 | a–d | 3 | 25.0 | a–d | 3 | 179.2 | b–e | 1 | 2.052 | b–c | 3 | 8.83 | a–c | 3 | 3.50 | b–c |
| 10+4 | 3 | 8.3 | b–e | 3 | 8.3 | a–e | 3 | 169.8 | b–e | 2 | 2.222 | b–c | 3 | 8.50 | a–c | 3 | 3.92 | a–c |
| 10+6 | 3 | 0.0 | e | 3 | 0.0 | e | 3 | 213.6 | b–e | 3 | 1.958 | b–c | 3 | 8.58 | a–c | 3 | 3.67 | a–c |
| 10+8 | 3 | 0.0 | e | 3 | 0.0 | e | 3 | 218.6 | b–d | 3 | 1.872 | b–c | 3 | 8.83 | a–c | 3 | 3.50 | b–c |
| 20+2 | 3 | 50.0 | a | 3 | 25.0 | a–d | 3 | 198.7 | b–e | | | | 3 | 8.22 | a–c | 3 | 4.00 | a–b |
| 20+4 | 3 | 8.3 | b–e | 3 | 8.3 | a–e | 3 | 180.3 | b–e | 2 | 1.996 | b–c | 3 | 7.67 | a–c | 3 | 3.83 | a–c |
| 20+6 | 3 | 0.0 | e | 3 | 0.0 | e | 3 | 187.1 | b–e | 3 | 2.041 | b–c | 3 | 8.50 | a–c | 3 | 3.67 | a–c |
| 20+8 | 3 | 0.0 | e | 3 | 0.0 | e | 3 | 216.7 | b–d | 3 | 1.857 | b–c | 3 | 6.75 | b–c | 3 | 3.00 | c |
| 30+2 | 3 | 0.0 | e | 3 | 0.0 | e | 3 | 181.8 | b–e | 3 | 2.170 | b–c | 3 | 8.75 | a–c | 3 | 3.75 | a–c |
| 30+4 | 3 | 8.3 | b–e | 3 | 8.3 | a–e | 3 | 219.5 | b–d | 2 | 1.803 | b–c | 3 | 8.33 | a–c | 3 | 4.00 | a–b |
| 30+6 | 3 | 8.3 | b–e | 3 | 0.0 | e | 3 | 253.7 | a–b | 2 | 1.680 | b–c | 3 | 8.08 | a–c | 3 | 3.50 | b–c |
| 30+8 | 3 | 8.3 | b–e | 3 | 0.0 | e | 3 | 230.3 | b–d | 2 | 1.817 | b–c | 3 | 6.14 | c | 3 | 3.58 | a–c |
| 40+2 | 3 | 8.3 | b–e | 3 | 0.0 | e | 3 | 198.7 | b–e | 2 | 2.186 | b–c | 3 | 8.42 | a–c | 3 | 3.75 | a–c |
| 40+4 | 3 | 0.0 | e | 3 | 0.0 | e | 3 | 208.8 | b–e | 3 | 1.832 | b–c | 3 | 8.17 | a–c | 3 | 3.75 | a–c |
| 40+6 | 3 | 0.0 | e | 3 | 0.0 | e | 3 | 226.9 | b–d | 3 | 1.817 | b–c | 3 | 7.67 | a–c | 3 | 3.50 | b–c |
| 40+8 | 3 | 0.0 | e | 3 | 0.0 | e | 3 | 242.8 | a–c | 3 | 1.743 | b–c | 3 | 3.17 | d | 3 | 1.83 | d |

EXPERIMENT NO. 22
Statistical Analyses of Percent Mortality, Weight Gain, Feed/Gain,
Intestinal and Cecal Lesion Scores of broiler cockerels inoculated with
*E. tenella* and *E. acervulina*

| Treatment | Mortality Mean | | | | | | Wt. Gain | | Feed/Gain | | | Lesion Scores | | | | | |
|---|---|---|---|---|---|---|---|---|---|---|---|---|---|---|---|---|---|
| | | | | | | | | | | | | Intestinal | | | Cecal | | |
| PPM | # | Total % | | # | % DTC | | # | Mean | # | Mean | | # | Mean | | # | Mean | |
| NC | | | | | | | | | | | | | | | | | |
| 0 | 3 | 0.0 | e | 3 | 0.0 | e | 3 | 286.4 | a | 3 | 1.487 | d | 3 | 0.00 | e | 3 | 0.00 | f |
| IC | | | | | | | | | | | | | | | | | | |
| 0 | 3 | 8.3 | a–e | 3 | 8.3 | a–e | 3 | 217.7 | b–e | 2 | 1.827 | a–d | 3 | 5.50 | a–b | 3 | 3.75 | a |
| NARASIN | | | | | | | | | | | | | | | | | | |
| 10 | 3 | 16.7 | a–d | 3 | 16.7 | a–d | 3 | 178.0 | e | 2 | 2.100 | a | 3 | 6.17 | a–b | 3 | 3.75 | a |
| 20 | 3 | 8.3 | a–e | 3 | 8.3 | a–e | 3 | 188.7 | d–e | 2 | 1.725 | a–d | 3 | 4.17 | a–d | 3 | 3.42 | a–c |
| 30 | 3 | 0.0 | e | 3 | 0.0 | e | 3 | 195.5 | b–e | 3 | 1.873 | a–d | 3 | 3.58 | b–d | 3 | 3.33 | a–c |
| 40 | 3 | 8.3 | a–e | 3 | 0.0 | e | 3 | 232.2 | a–e | 2 | 1.757 | a–d | 3 | 2.69 | c–e | 3 | 3.81 | a |
| Example No. 57 | | | | | | | | | | | | | | | | | | |
| 2 | 3 | 16.7 | a–d | 3 | 16.7 | a–d | 3 | 195.4 | c–e | 1 | 1.911 | a–d | 3 | 6.58 | a | 3 | 3.92 | a |
| 4 | 3 | 8.3 | a–e | 3 | 0.0 | e | 3 | 196.6 | b–e | 2 | 2.019 | a–b | 3 | 4.78 | a–c | 3 | 3.92 | a |
| 6 | 3 | 0.0 | e | 3 | 0.0 | e | 3 | 223.1 | a–e | 3 | 1.757 | a–d | 3 | 2.08 | c–e | 3 | 3.67 | a |
| 8 | 3 | 0.0 | e | 3 | 0.0 | e | 3 | 224.3 | a–e | 3 | 1.731 | a–d | 3 | 1.58 | d–e | 3 | 3.83 | a |
| NARASIN + Example No. 57 | | | | | | | | | | | | | | | | | | |
| 10+2 | 3 | 25.0 | a | 3 | 25.0 | a | 3 | 213.9 | b–e | | | | 3 | 4.00 | a–d | 3 | 3.67 | a |
| 10+4 | 3 | 0.0 | e | 3 | 0.0 | e | 3 | 214.5 | b–e | 3 | 1.785 | a–d | 3 | 2.25 | c–e | 3 | 3.75 | a |
| 10+6 | 3 | 16.7 | a–d | 3 | 16.7 | a–d | 3 | 248.8 | a–d | 2 | 1.689 | a–d | 3 | 0.67 | e | 3 | 3.42 | a–c |
| 10+8 | 3 | 0.0 | e | 3 | 0.0 | e | 3 | 241.1 | a–e | 3 | 1.771 | a–d | 3 | 0.00 | e | 3 | 2.92 | a–c |
| 20+2 | 3 | 8.3 | a–e | 3 | 8.3 | a–e | 3 | 203.4 | b–e | 2 | 1.919 | a–c | 3 | 3.92 | a–d | 3 | 3.58 | a |
| 20+4 | 3 | 0.0 | e | 3 | 0.0 | e | 3 | 241.4 | a–e | 3 | 1.683 | b–d | 3 | 0.75 | e | 3 | 3.50 | a–b |
| 20+6 | 3 | 8.3 | a–e | 3 | 8.3 | a–e | 3 | 255.4 | a–d | 2 | 1.667 | b–d | 3 | 0.08 | e | 3 | 3.42 | a–c |
| 20+8 | 3 | 0.0 | e | 3 | 0.0 | e | 3 | 240.1 | a–e | 3 | 1.642 | b–d | 3 | 0.00 | e | 3 | 3.00 | a–c |
| 30+2 | 3 | 0.0 | e | 3 | 0.0 | e | 3 | 243.6 | a–e | 3 | 1.645 | b–d | 3 | 1.75 | d–e | 3 | 3.67 | a |
| 30+4 | 3 | 0.0 | e | 3 | 0.0 | e | 3 | 253.0 | a–d | 3 | 1.593 | c–d | 3 | 0.08 | e | 3 | 2.75 | a–c |
| 30+6 | 3 | 0.0 | e | 3 | 0.0 | e | 3 | 254.6 | a–d | 3 | 1.614 | c–d | 3 | 0.08 | e | 3 | 2.42 | b–d |
| 30+8 | 3 | 0.0 | e | 3 | 0.0 | e | 3 | 246.3 | a–d | 3 | 1.616 | c–d | 3 | 0.00 | e | 3 | 1.67 | d–e |
| 40+2 | 3 | 0.0 | e | 3 | 0.0 | e | 3 | 239.8 | a–e | 3 | 1.645 | b–d | 3 | 1.58 | d–e | 3 | 3.67 | a |
| 40+4 | 3 | 0.0 | e | 3 | 0.0 | e | 3 | 263.3 | a–b | 3 | 1.591 | c–d | 3 | 0.00 | e | 3 | 3.42 | a–c |
| 40+6 | 3 | 0.0 | e | 3 | 0.0 | e | 3 | 256.5 | a–d | 3 | 1.589 | c–d | 3 | 0.00 | e | 3 | 2.33 | c–d |
| 40+8 | 3 | 8.3 | a–e | 3 | 0.0 | e | 3 | 259.4 | a–c | 2 | 1.684 | b–d | 3 | 0.08 | e | 3 | 1.50 | e |

-continued

EXPERIMENT NO. 23
Statistical Analyses of Percent Mortality, Weight Gain, Feed/Gain, Intestinal and Cecal Lesion Scores of broiler cockerels inoculated with *E. maxima* and *E. tenella*

| Treatment | | Mortality Mean | | | | | Wt. Gain | | Feed/Gain | | Intestinal (Lesion) | | Cecal (Lesion) | |
|---|---|---|---|---|---|---|---|---|---|---|---|---|---|---|
| PPM | # | Total % | | # | % DTC | | # | Mean | # | Mean | # | Mean | # | Mean |
| NC | | | | | | | | | | | | | | |
| 0 | 3 | 0.0 | e | 3 | 0.0 | e | 3 | 362.3 a | 3 | 1.289 f | 3 | 0.33 e | 3 | 0.00 g |
| IC | | | | | | | | | | | | | | |
| 0 | 3 | 16.7 | a–b | 3 | 16.7 | a–b | 3 | 172.8 f | 2 | 1.976 a | 3 | 8.42 a | 3 | 3.67 a–b |
| NARASIN | | | | | | | | | | | | | | |
| 10 | 3 | 8.3 | a–e | 3 | 8.3 | a–e | 3 | 193.8 e–f | 2 | 1.779 a–d | 3 | 8.42 a | 3 | 3.83 a–b |
| 20 | 3 | 8.3 | a–e | 3 | 8.3 | a–e | 3 | 234.5 b–f | 2 | 1.682 a–f | 3 | 8.92 a | 3 | 3.58 a–b |
| 30 | 3 | 8.3 | a–e | 3 | 0.0 | e | 3 | 253.0 b–e | 2 | 1.639 a–f | 3 | 8.75 a | 3 | 3.64 a–b |
| 40 | 3 | 0.0 | e | 3 | 0.0 | e | 3 | 211.0 d–f | 3 | 1.655 a–f | 3 | 8.92 a | 3 | 3.75 a–b |
| Example No. 57 | | | | | | | | | | | | | | |
| 2 | 3 | 8.3 | a–e | 3 | 8.3 | a–e | 3 | 178.3 e–f | 2 | 1.933 a–b | 3 | 8.58 a | 3 | 3.58 a–b |
| 4 | 3 | 0.0 | e | 3 | 0.0 | e | 3 | 212.0 d–f | 3 | 1.793 a–c | 3 | 8.83 a | 3 | 3.67 a–b |
| 6 | 3 | 8.3 | a–e | 3 | 8.3 | a–e | 3 | 225.3 c–f | 2 | 1.706 a–e | 3 | 8.25 a | 3 | 3.42 a–b |
| 8 | 3 | 0.0 | e | 3 | 0.0 | e | 3 | 246.6 b–f | 3 | 1.635 a–f | 3 | 7.58 a–b | 3 | 3.58 a–b |
| NARASIN + Example No. 57 | | | | | | | | | | | | | | |
| 10+2 | 3 | 16.7 | a–b | 3 | 16.7 | a–b | 3 | 250.7 b–e | 2 | 1.659 a–f | 3 | 7.58 a–b | 3 | 3.67 a–b |
| 10+4 | 3 | 0.0 | e | 3 | 0.0 | e | 3 | 241.4 b–f | 3 | 1.544 c–f | 3 | 7.75 a–b | 3 | 3.50 a–b |
| 10+6 | 3 | 0.0 | e | 3 | 0.0 | e | 3 | 280.3 b–d | 3 | 1.447 d–f | 3 | 7.75 a–b | 3 | 3.58 a–b |
| 10+8 | 3 | 0.0 | e | 3 | 0.0 | e | 3 | 301.3 a–c | 3 | 1.428 d–f | 3 | 1.67 d–e | 3 | 1.67 d–f |
| 20+2 | 3 | 0.0 | e | 3 | 0.0 | e | 3 | 247.7 b–f | 3 | 1.613 b–f | 3 | 8.67 a | 3 | 3.75 a–b |
| 20+4 | 3 | 0.0 | e | 3 | 0.0 | e | 3 | 291.6 a–d | 3 | 1.453 d–f | 3 | 6.50 a–c | 3 | 2.92 a–c |
| 20+6 | 3 | 0.0 | e | 3 | 0.0 | e | 3 | 309.9 a–c | 3 | 1.401 d–f | 3 | 3.25 b–e | 3 | 2.25 c–e |
| 20+8 | 3 | 0.0 | e | 3 | 0.0 | e | 3 | 303.3 a–c | 3 | 1.429 d–f | 3 | 1.42 d–e | 3 | 1.42 e–f |
| 30+2 | 3 | 0.0 | e | 3 | 0.0 | e | 3 | 272.3 b–d | 3 | 1.430 d–f | 3 | 7.42 a–b | 3 | 3.92 a |
| 30+4 | 3 | 8.3 | a–e | 3 | 8.3 | a–e | 3 | 294.7 a–c | 2 | 1.495 c–f | 3 | 3.42 b–e | 3 | 2.48 b–d |
| 30+6 | 3 | 0.0 | e | 3 | 0.0 | e | 3 | 314.3 a–b | 3 | 1.372 e–f | 3 | 3.00 c–e | 3 | 2.08 c–e |
| 30+8 | 3 | 0.0 | e | 3 | 0.0 | e | 3 | 296.4 a–c | 3 | 1.429 d–f | 3 | 1.17 d–e | 3 | 0.75 f–g |
| 40+2 | 3 | 0.0 | e | 3 | 0.0 | e | 3 | 274.0 b–d | 3 | 1.378 e–f | 3 | 5.50 a–d | 3 | 3.92 a |
| 40+4 | 3 | 0.0 | e | 3 | 0.0 | e | 3 | 286.6 a–d | 3 | 1.451 d–f | 3 | 2.00 d–e | 3 | 2.17 c–e |
| 40+6 | 3 | 0.0 | e | 3 | 0.0 | e | 3 | 308.1 a–c | 3 | 1.383 d–f | 3 | 0.83 d–e | 3 | 1.58 d–f |
| 40+8 | 3 | 0.0 | e | 3 | 0.0 | e | 3 | 292.9 a–d | 3 | 1.428 d–f | 3 | 0.83 d–e | 3 | 0.67 f–g |

EXPERIMENT NO. 24
Statistical Analyses of Percent Mortality, Weight Gain, Feed/Gain, Intestinal and Cecal Lesion Scores of broiler cockerels inoculated with *E. acervulina* and *E. tenella*

| Treatment | | Mortality Mean | | | | | Wt. Gain | | Feed/Gain | | Intestinal (Lesion) | | Cecal (Lesion) | |
|---|---|---|---|---|---|---|---|---|---|---|---|---|---|---|
| PPM | # | Total % | | # | % DTC | | # | Mean | # | Mean | # | Mean | # | Mean |
| NC | | | | | | | | | | | | | | |
| 0 | 3 | 8.3 | a | 3 | 0.0 | a | 3 | 308.4 a | 2 | 1.433 b | 3 | 0.00 e | 3 | 0.00 e |
| IC | | | | | | | | | | | | | | |
| 0 | 3 | 16.7 | a | 3 | 16.7 | a | 3 | 209.7 b–c | 1 | 1.796 a–b | 3 | 6.75 a | 3 | 3.75 a–b |
| NARASIN | | | | | | | | | | | | | | |
| 60 | 3 | 16.7 | a | 3 | 16.7 | a | 3 | 258.7 a–c | 2 | 1.693 a–b | 3 | 2.75 b–e | 3 | 4.00 a |
| 80 | 3 | 0.0 | a | 3 | 0.0 | a | 3 | 230.9 a–c | 3 | 1.741 a–b | 3 | 0.83 c–e | 3 | 3.75 a–b |
| Example No. 57 | | | | | | | | | | | | | | |
| 2 | 3 | 8.3 | a | 3 | 8.3 | a | 3 | 228.6 a–c | 2 | 1.749 a–b | 3 | 4.75 a–b | 3 | 3.58 a–b |
| 4 | 3 | 0.0 | a | 3 | 0.0 | a | 3 | 245.9 a–c | 3 | 1.799 a–b | 3 | 3.17 b–d | 3 | 3.92 a |
| 8 | 3 | 0.0 | a | 3 | 0.0 | a | 3 | 250.3 a–c | 3 | 1.747 a–b | 3 | 0.92 c–e | 3 | 3.25 a–b |
| Example No. 56 | | | | | | | | | | | | | | |
| 2 | 3 | 8.3 | a | 3 | 8.3 | a | 3 | 192.5 c | 2 | 1.914 a | 3 | 6.00 a | 3 | 3.75 a–b |
| 4 | 3 | 16.7 | a | 3 | 8.3 | a | 3 | 236.2 a–c | 1 | 1.764 a–b | 3 | 6.92 a | 3 | 3.75 a–b |
| 8 | 3 | 8.3 | a | 3 | 8.3 | a | 3 | 238.7 a–c | 2 | 1.776 a–b | 3 | 3.33 b–c | 3 | 3.17 a–b |

-continued

| | | | | | | | | | | | | | | | | | | | |
|---|---|---|---|---|---|---|---|---|---|---|---|---|---|---|---|---|---|---|---|
| NARASIN + Example No. 57 | | | | | | | | | | | | | | | | | | | |
| 60+2 | 3 | 0.0 | a | 3 | 0.0 | a | 3 | 252.0 | a-c | 3 | 1.740 | a-b | 3 | 1.33 | c-e | 3 | 3.92 | a |
| 60+4 | 3 | 0.0 | a | 3 | 0.0 | a | 3 | 270.9 | a-c | 3 | 1.612 | a-b | 3 | 0.42 | d-e | 3 | 3.92 | a |
| 60+8 | 3 | 0.0 | a | 3 | 0.0 | a | 3 | 266.3 | a-c | 3 | 1.640 | a-b | 3 | 0.00 | e | 3 | 1.17 | d |
| 80+2 | 3 | 16.7 | a | 3 | 16.7 | a | 3 | 255.1 | a-c | 3 | 1.676 | a-b | 3 | 2.33 | c-e | 3 | 3.92 | a |
| 80+4 | 3 | 0.0 | a | 3 | 0.0 | a | 3 | 253.3 | a-c | 3 | 1.648 | a-b | 3 | 0.25 | e | 3 | 3.83 | a |
| 80+8 | 3 | 0.0 | a | 3 | 0.0 | a | 3 | 274.5 | a-c | 3 | 1.645 | a-b | 3 | 0.00 | e | 3 | 1.92 | c |
| NARASIN + Example No. 56 | | | | | | | | | | | | | | | | | | | |
| 60+2 | 3 | 0.0 | a | 3 | 0.0 | a | 3 | 279.5 | a-b | 3 | 1.571 | a-b | 3 | 0.92 | c-e | 3 | 3.75 | a-b |
| 60+4 | 3 | 0.0 | a | 3 | 0.0 | a | 3 | 258.8 | a-c | 3 | 1.659 | a-b | 3 | 1.08 | c-e | 3 | 3.92 | a |
| 60+8 | 3 | 0.0 | a | 3 | 0.0 | a | 3 | 270.8 | a-c | 3 | 1.603 | a-b | 3 | 0.08 | e | 3 | 2.67 | b-c |
| 80+2 | 3 | 8.3 | a | 3 | 8.3 | a | 3 | 240.0 | a-c | 3 | 1.769 | a-b | 3 | 2.08 | c-e | 3 | 4.00 | a |
| 80+4 | 3 | 0.0 | a | 3 | 0.0 | a | 3 | 282.7 | a-b | 3 | 1.620 | a-b | 3 | 0.25 | e | 3 | 3.83 | a |
| 80+8 | 3 | 0.0 | a | 3 | 0.0 | a | 3 | 272.1 | a-c | 3 | 1.610 | a-b | 3 | 0.00 | e | 3 | 2.17 | c |

EXPERIMENT NO. 25
Statistical Analyses of Percent Mortality, Weight Gain, Feed/Gain,
Intestinal and Cecal Lesion Scores of broiler cockerels inoculated with
*E. maxima* and *E. tenella*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 3 | 8.3 a | 3 | 0.0 a | 3 | 265.5 a | 2 | 1.432 d | 3 | 0.00 d | 3 | 0.00 d |
| IC | | | | | | | | | | | | |
| 0 | 3 | 8.3 a | 3 | 8.3 a | 3 | 160.9 d | 2 | 1.880 b-c | 3 | 8.67 a-b | 3 | 3.83 a-b |
| NARASIN | | | | | | | | | | | | |
| 60 | 3 | 8.3 a | 3 | 8.3 a | 3 | 175.4 c-d | 2 | 2.158 a-b | 3 | 7.83 a-b | 3 | 3.75 a-b |
| 80 | 3 | 25.0 a | 3 | 25.0 a | 3 | 212.1 a-d | 1 | 1.774 b-d | 3 | 5.83 a-c | 3 | 3.58 a-b |
| Example No. 57 | | | | | | | | | | | | |
| 2 | 3 | 16.7 a | 3 | 16.7 a | 3 | 148.3 d | 1 | 2.528 a | 3 | 8.25 a-b | 3 | 3.83 a-b |
| 4 | 3 | 25.0 a | 3 | 16.7 a | 3 | 159.8 d | | | 3 | 8.17 a-b | 3 | 3.31 a-b |
| 8 | 3 | 0.0 a | 3 | 0.0 a | 3 | 201.9 a-d | 3 | 1.795 b-d | 3 | 4.50 a-d | 3 | 2.33 c |
| Example No. 56 | | | | | | | | | | | | |
| 2 | 3 | 16.7 a | 3 | 16.7 a | 3 | 146.8 d | 1 | 2.283 a-b | 3 | 8.17 a-b | 3 | 3.67 a-b |
| 4 | 3 | 8.3 a | 3 | 8.3 a | 3 | 156.9 d | 2 | 2.205 a-b | 3 | 8.42 a-b | 3 | 3.92 a |
| 8 | 3 | 8.3 a | 3 | 8.3 a | 3 | 158.3 d | 2 | 2.027 b-c | 3 | 8.92 a | 3 | 3.67 a-b |
| NARASIN + Example No. 57 | | | | | | | | | | | | |
| 60+2 | 3 | 0.0 a | 3 | 0.0 a | 3 | 191.1 b-d | 3 | 1.839 b-c | 3 | 4.08 a-d | 3 | 3.67 a-b |
| 60+4 | 3 | 8.3 a | 3 | 8.3 a | 3 | 248.0 a-b | 2 | 1.618 c-d | 3 | 3.58 b-d | 3 | 3.83 a-b |
| 60+8 | 3 | 0.0 a | 3 | 0.0 a | 3 | 241.7 a-c | 3 | 1.619 c-d | 3 | 2.33 c-d | 3 | 2.25 c |
| 80+2 | 3 | 16.7 a | 3 | 16.7 a | 3 | 200.8 a-d | 2 | 1.890 b-c | 3 | 6.00 a-c | 3 | 3.83 a-b |
| 80+4 | 3 | 8.3 a | 3 | 8.3 a | 3 | 231.2 a-c | 2 | 1.784 b-d | 3 | 4.00 a-d | 3 | 3.58 a-b |
| 80+8 | 3 | 0.0 a | 3 | 0.0 a | 3 | 238.6 a-c | 3 | 1.624 c-d | 3 | 0.67 d | 3 | 2.25 c |
| NARASIN + Example No. 56 | | | | | | | | | | | | |
| 60+2 | 3 | 16.7 a | 3 | 8.3 a | 3 | 179.6 c-d | 2 | 1.799 b-d | 3 | 6.44 a-c | 3 | 3.75 a-b |
| 60+4 | 3 | 8.3 a | 3 | 8.3 a | 3 | 213.1 a-d | 2 | 1.809 b-d | 3 | 6.42 a-c | 3 | 3.83 a-b |
| 60+8 | 3 | 0.0 a | 3 | 0.0 a | 3 | 239.2 a-c | 3 | 1.649 c-d | 3 | 3.58 b-d | 3 | 2.83 b-c |
| 80+2 | 3 | 8.3 a | 3 | 8.3 a | 3 | 191.4 b-d | 2 | 1.766 b-d | 3 | 7.08 a-c | 3 | 4.00 a |
| 80+4 | 3 | 8.3 a | 3 | 0.0 a | 3 | 246.6 a-b | 2 | 1.729 c-d | 3 | 5.22 a-c | 3 | 3.72 a-b |
| 80+8 | 3 | 16.7 a | 3 | 8.3 a | 3 | 229.3 a-c | 1 | 1.555 c-d | 3 | 0.17 d | 3 | 2.47 c |

EXPERIMENT NO. 26
Statistical Analyses of Percent Mortality, Weight Gain, Feed/Gain, Intestinal and Cecal Lesion Scores of broiler cockerels inoculated with *E. tenella* and *E. acervulina*

| Treatment | | Mortality Mean | | | | | Wt. Gain | | Feed/Gain | | Lesion Scores | | | | |
|---|---|---|---|---|---|---|---|---|---|---|---|---|---|---|---|
| | | | | | | | | | | | Intestinal | | Cecal | | |
| PPM | # | Total % | | # | % DTC | | # | Mean | # | Mean | # | Mean | | # | Mean | |
| NC | | | | | | | | | | | | | | | | |
| 0 | 3 | 0.0 | h | 3 | 0.0 | h | 3 | 313.9 | a | 3 | 1.511 | h | 3 | 0.00 | e | 3 | 0.00 | h |
| IC | | | | | | | | | | | | | | | | |
| 0 | 3 | 16.7 | a–d | 3 | 16.7 | a–c | 3 | 242.4 | e–h | 2 | 1.800 | a–b | 3 | 3.83 | a | 3 | 3.50 | a–e |
| A80190 | | | | | | | | | | | | | | | | |
| 4 | 3 | 8.3 | a–h | 3 | 8.3 | a–h | 3 | 264.0 | a–h | 2 | 1.711 | a–e | 3 | 3.58 | a | 3 | 3.67 | a–e |
| 8 | 3 | 16.7 | a–d | 3 | 16.7 | a–c | 3 | 261.1 | a–h | 1 | 1.511 | h | 3 | 3.67 | a | 3 | 3.33 | a–e |
| 16 | 3 | 0.0 | h | 3 | 0.0 | h | 3 | 267.8 | a–h | 3 | 1.621 | a–h | 3 | 1.83 | a–e | 3 | 3.67 | a–e |
| Example No. 57 | | | | | | | | | | | | | | | | |
| 2 | 3 | 0.0 | h | 3 | 0.0 | h | 3 | 253.4 | b–h | 3 | 1.647 | a–h | 3 | 3.08 | a–b | 3 | 3.67 | a–e |
| 4 | 3 | 0.0 | h | 3 | 0.0 | h | 3 | 251.5 | c–h | 3 | 1.668 | a–g | 3 | 3.17 | a–b | 3 | 3.42 | a–e |
| 8 | 3 | 0.0 | h | 3 | 0.0 | h | 3 | 249.8 | d–h | 3 | 1.665 | a–h | 3 | 1.42 | a–e | 3 | 3.50 | a–e |
| Example No. 56 | | | | | | | | | | | | | | | | |
| 2 | 3 | 8.3 | a–h | 3 | 8.3 | a–h | 3 | 238.8 | f–h | 2 | 1.794 | a–c | 3 | 3.75 | a | 3 | 3.25 | a–e |
| 4 | 3 | 8.3 | a–h | 3 | 0.0 | h | 3 | 273.1 | a–h | 2 | 1.628 | a–h | 3 | 3.00 | a–c | 3 | 3.61 | a–e |
| 8 | 3 | 8.3 | a–h | 3 | 8.3 | a–h | 3 | 267.1 | a–h | 2 | 1.651 | a–h | 3 | 2.25 | a–e | 3 | 3.08 | a–e |
| A80190 + Example No. 57 | | | | | | | | | | | | | | | | |
| 4+2 | 3 | 0.0 | h | 3 | 0.0 | h | 3 | 220.5 | h | 3 | 1.810 | a | 3 | 2.67 | a–d | 3 | 3.67 | a–e |
| 4+4 | 3 | 16.7 | a–d | 3 | 16.7 | a–c | 3 | 272.6 | a–h | 1 | 1.538 | e–h | 3 | 3.17 | a–b | 3 | 3.67 | a–e |
| 4+8 | 3 | 0.0 | h | 3 | 0.0 | h | 3 | 277.3 | a–h | 3 | 1.622 | a–h | 3 | 0.00 | e | 3 | 2.00 | e–g |
| 8+2 | 3 | 0.0 | h | 3 | 0.0 | h | 3 | 297.3 | a–c | 3 | 1.531 | f–h | 3 | 2.00 | a–e | 3 | 3.75 | a–c |
| 8+4 | 3 | 8.3 | a–h | 3 | 8.3 | a–h | 3 | 283.5 | a–g | 2 | 1.545 | c–h | 3 | 1.67 | a–e | 3 | 3.00 | b–e |
| 8+8 | 3 | 0.0 | h | 3 | 0.0 | h | 3 | 281.9 | a–h | 3 | 1.595 | a–h | 3 | 0.25 | d–e | 3 | 2.00 | e–g |
| 16+2 | 3 | 0.0 | h | 3 | 0.0 | h | 3 | 271.5 | a–h | 3 | 1.620 | a–h | 3 | 0.83 | b–e | 3 | 3.42 | a–e |
| 16+4 | 3 | 0.0 | h | 3 | 0.0 | h | 3 | 295.2 | a–d | 3 | 1.537 | e–h | 3 | 1.50 | a–e | 3 | 3.42 | a–e |
| 16+8 | 3 | 8.3 | a–h | 3 | 0.0 | h | 3 | 287.7 | a–f | 2 | 1.598 | a–h | 3 | 0.00 | e | 3 | 0.81 | g–h |
| A80190 + Example No. 56 | | | | | | | | | | | | | | | | |
| 4+2 | 3 | 8.3 | a–h | 3 | 8.3 | a–h | 3 | 265.6 | a–h | 2 | 1.659 | a–h | 3 | 3.33 | a–b | 3 | 3.50 | a–e |
| 4+4 | 3 | 0.0 | h | 3 | 0.0 | h | 3 | 257.3 | a–h | 3 | 1.697 | a–f | 3 | 2.50 | a–e | 3 | 3.92 | a |
| 4+8 | 3 | 8.3 | a–h | 3 | 8.3 | a–h | 3 | 265.8 | a–h | 3 | 1.591 | a–h | 3 | 1.83 | a–e | 3 | 3.75 | a–c |
| 8+2 | 3 | 0.0 | h | 3 | 0.0 | h | 3 | 231.4 | g–h | 3 | 1.766 | a–d | 3 | 2.08 | a–e | 3 | 3.33 | a–e |
| 8+4 | 3 | 0.0 | h | 3 | 0.0 | h | 3 | 259.6 | a–h | 3 | 1.624 | a–h | 3 | 1.33 | a–e | 3 | 3.50 | a–e |
| 8+8 | 3 | 0.0 | h | 3 | 0.0 | h | 3 | 268.2 | a–h | 3 | 1.644 | a–h | 3 | 1.50 | a–e | 3 | 2.67 | c–f |
| 16+2 | 3 | 16.7 | a–d | 3 | 8.3 | a–h | 3 | 291.8 | a–e | 1 | 1.622 | a–h | 3 | 1.25 | a–e | 3 | 3.33 | a–e |
| 16+4 | 3 | 0.0 | h | 3 | 0.0 | h | 3 | 281.7 | a–h | 3 | 1.585 | a–h | 3 | 0.92 | b–e | 3 | 3.08 | a–e |
| 16+8 | 3 | 0.0 | h | 3 | 0.0 | h | 3 | 299.0 | a–b | 3 | 1.556 | b–h | 3 | 0.42 | c–e | 3 | 1.58 | f–g |

EXPERIMENT NO. 27
Statistical Analyses of Percent Mortality, Weight Gain, Feed/Gain, Intestinal and Cecal Lesion Scores of broiler cockerels inoculated with *E. maxima* and *E. tenella*

| Treatment | | Mortality Mean | | | | | Wt. Gain | | Feed/Gain | | Lesion Scores | | | | |
|---|---|---|---|---|---|---|---|---|---|---|---|---|---|---|---|
| | | | | | | | | | | | Intestinal | | Cecal | | |
| PPM | # | Total % | | # | % DTC | | # | Mean | # | Mean | # | Mean | | # | Mean | |
| NC | | | | | | | | | | | | | | | | |
| 0 | 3 | 0.0 | h | 3 | 0.0 | h | 3 | 271.4 | a | 3 | 1.522 | h | 3 | 0.00 | f | 3 | 0.00 | g |
| IC | | | | | | | | | | | | | | | | |
| 0 | 3 | 8.3 | a–h | 3 | 8.3 | a–h | 3 | 151.7 | h | 2 | 2.374 | a | 3 | 7.67 | a–d | 3 | 3.42 | a–d |
| A80190 | | | | | | | | | | | | | | | | |
| 4 | 3 | 0.0 | h | 3 | 0.0 | h | 3 | 199.9 | a–h | 3 | 1.903 | b–e | 3 | 8.17 | a–d | 3 | 3.58 | a–d |
| 8 | 3 | 8.3 | a–h | 3 | 8.3 | a–h | 3 | 190.1 | b–h | 2 | 1.791 | b–h | 3 | 8.50 | a–d | 3 | 3.75 | a–d |
| 16 | 3 | 0.0 | h | 3 | 0.0 | h | 3 | 190.8 | a–h | 3 | 1.882 | b–f | 3 | 8.00 | a–d | 3 | 3.75 | a–d |
| Example No. 57 | | | | | | | | | | | | | | | | |
| 2 | 3 | 16.7 | a–e | 3 | 8.3 | a–h | 3 | 171.1 | f–h | 1 | 1.610 | c–h | 3 | 9.22 | a | 3 | 4.00 | a |

| | | | | | | | | | | | | | | | | | | |
|---|---|---|---|---|---|---|---|---|---|---|---|---|---|---|---|---|---|---|
| 4 | 3 | 8.3 | a-h | 3 | 0.0 | h | 3 | 218.6 | a-h | 2 | 1.688 | b-h | 3 | 8.50 | a-d | 3 | 3.75 | a-d |
| 8 | 3 | 0.0 | h | 3 | 0.0 | h | 3 | 223.8 | a-h | 3 | 1.689 | b-h | 3 | 6.42 | a-d | 3 | 2.92 | a-d |
| Example No. 56 | | | | | | | | | | | | | | | | | | |
| 2 | 3 | 8.3 | a-h | 3 | 8.3 | a-h | 3 | 164.4 | g-h | 2 | 2.079 | a-b | 3 | 8.00 | a-d | 3 | 3.67 | a-d |
| 4 | 3 | 0.0 | h | 3 | 0.0 | h | 3 | 182.6 | e-h | 3 | 1.949 | b-c | 3 | 8.33 | a-d | 3 | 3.75 | a-d |
| 8 | 3 | 0.0 | h | 3 | 0.0 | h | 3 | 224.0 | a-h | 3 | 1.670 | b-h | 3 | 6.25 | a-d | 3 | 3.33 | a-d |
| A80190 + Example No. 57 | | | | | | | | | | | | | | | | | | |
| 4+2 | 3 | 8.3 | a-h | 3 | 8.3 | a-h | 3 | 188.4 | d-h | 2 | 1.924 | b-d | 3 | 7.92 | a-d | 3 | 3.58 | a-d |
| 4+4 | 3 | 16.7 | a-e | 3 | 8.3 | a-h | 3 | 204.8 | a-h | 2 | 1.793 | b-h | 3 | 6.08 | b-d | 3 | 3.67 | a-d |
| 4+8 | 3 | 8.3 | a-h | 3 | 0.0 | h | 3 | 229.2 | a-h | 2 | 1.623 | b-h | 3 | 3.92 | d-e | 3 | 2.78 | c-d |
| 8+2 | 3 | 0.0 | h | 3 | 0.0 | h | 3 | 199.9 | a-h | 3 | 1.817 | b-h | 3 | 8.83 | a-b | 3 | 3.58 | a-d |
| 8+4 | 3 | 16.7 | a-e | 3 | 16.7 | a-b | 3 | 239.5 | a-f | 1 | 1.567 | e-h | 3 | 6.42 | a-d | 3 | 3.33 | a-d |
| 8+8 | 3 | 0.0 | h | 3 | 0.0 | h | 3 | 260.8 | a-b | 3 | 1.549 | g-h | 3 | 1.33 | e-f | 3 | 1.83 | e-f |
| 16+2 | 3 | 8.3 | a-h | 3 | 8.3 | a-h | 3 | 228.4 | a-h | 2 | 1.739 | b-h | 3 | 6.83 | a-d | 3 | 3.42 | a-d |
| 16+4 | 3 | 0.0 | h | 3 | 0.0 | h | 3 | 238.3 | a-g | 3 | 1.660 | b-h | 3 | 7.08 | a-d | 3 | 3.42 | a-d |
| 16+8 | 3 | 0.0 | h | 3 | 0.0 | h | 3 | 237.5 | a-g | 3 | 1.562 | f-h | 3 | 0.83 | e-f | 3 | 1.25 | f |
| A80190 + Example No. 56 | | | | | | | | | | | | | | | | | | |
| 4+2 | 3 | 8.3 | a-h | 3 | 8.3 | a-h | 3 | 190.1 | c-h | 2 | 1.841 | b-g | 3 | 6.92 | a-d | 3 | 2.83 | b-d |
| 4+4 | 3 | 0.0 | h | 3 | 0.0 | h | 3 | 230.1 | a-h | 3 | 1.638 | b-h | 3 | 8.17 | a-d | 3 | 3.08 | a-d |
| 4+8 | 3 | 8.3 | a-h | 3 | 0.0 | h | 3 | 241.4 | a-d | 2 | 1.586 | d-h | 3 | 6.97 | a-d | 3 | 3.36 | a-d |
| 8+2 | 3 | 8.3 | a-h | 3 | 8.3 | a-h | 3 | 199.2 | a-h | 2 | 1.828 | b-h | 3 | 7.42 | a-d | 3 | 3.75 | a-d |
| 8+4 | 3 | 0.0 | h | 3 | 0.0 | h | 3 | 212.1 | a-h | 3 | 1.714 | b-h | 3 | 8.00 | a-d | 3 | 3.58 | a-d |
| 8+8 | 3 | 0.0 | h | 3 | 0.0 | h | 3 | 240.1 | a-e | 3 | 1.615 | b-h | 3 | 4.00 | c-e | 3 | 2.50 | d-e |
| 16+2 | 3 | 16.7 | a-e | 3 | 16.7 | a-b | 3 | 238.0 | a-g | 2 | 1.691 | b-h | 3 | 7.50 | a-d | 3 | 3.67 | a-d |
| 16+4 | 3 | 0.0 | h | 3 | 0.0 | h | 3 | 236.4 | a-g | 3 | 1.640 | b-h | 3 | 7.17 | a-d | 3 | 3.50 | a-d |
| 16+8 | 3 | 16.7 | a-e | 3 | 8.3 | a-h | 3 | 256.3 | a-c | 2 | 1.622 | b-h | 3 | 1.75 | e-f | 3 | 1.69 | e-f |

EXPERIMENT NO. 28
Statistical Analyses of Percent Mortality, Weight Gain, Feed/Gain,
Intestinal and Cecal Lesion Scores of broiler cockerels inoculated with
*E. tenella* and *E. acervulina*

| Treatment | Mortality Mean | | | | | | Wt. Gain | | Feed/Gain | | | Lesion Scores | | | | | |
|---|---|---|---|---|---|---|---|---|---|---|---|---|---|---|---|---|---|
| | | | | | | | | | | | | Intestinal | | | Cecal | | |
| PPM | # | Total % | | # | % DTC | | # | Mean | # | Mean | | # | Mean | | # | Mean | |
| NC | | | | | | | | | | | | | | | | | |
| 0 | 3 | 0.0 | h | 3 | 0.0 | h | 3 | 308.2 | a | 3 | 1.475 | c-d | 3 | 0.00 | h | 3 | 0.00 | f |
| IC | | | | | | | | | | | | | | | | | |
| 0 | 3 | 8.3 | a-h | 3 | 8.3 | a-h | 3 | 214.7 | e-h | 2 | 1.872 | b | 3 | 6.33 | a-b | 3 | 3.58 | a-b |
| A80190 | | | | | | | | | | | | | | | | | |
| 4 | 3 | 33.3 | a | 3 | 25.0 | a-d | 3 | 193.0 | g-h | | | | 3 | 7.00 | a | 3 | 3.44 | a-b |
| 8 | 3 | 16.7 | a-h | 3 | 0.0 | h | 3 | 274.0 | a-f | 1 | 1.570 | b-d | 3 | 4.39 | a-e | 3 | 2.83 | a-b |
| 16 | 3 | 25.0 | a-e | 3 | 16.7 | a-g | 3 | 212.0 | f-h | 2 | 1.590 | b-d | 3 | 3.61 | a-h | 3 | 2.89 | a-b |
| Example No. 57 | | | | | | | | | | | | | | | | | | |
| 2 | 3 | 8.3 | a-h | 3 | 8.3 | a-h | 3 | 168.0 | h | 2 | 2.331 | a | 3 | 4.00 | a-f | 3 | 3.50 | a-b |
| 4 | 3 | 16.7 | a-h | 3 | 16.7 | a-g | 3 | 222.2 | c-h | 2 | 1.922 | b | 3 | 5.08 | a-c | 3 | 3.58 | a-b |
| 8 | 3 | 8.3 | a-h | 3 | 8.3 | a-h | 3 | 261.3 | a-f | 2 | 1.541 | c-d | 3 | 2.42 | c-h | 3 | 3.08 | a-b |
| Example No. 56 | | | | | | | | | | | | | | | | | | |
| 2 | 3 | 8.3 | a-h | 3 | 8.3 | a-h | 3 | 242.9 | a-g | 2 | 1.888 | b | 3 | 4.75 | a-d | 3 | 3.67 | a-b |
| 4 | 3 | 16.7 | a-h | 3 | 16.7 | a-g | 3 | 217.8 | d-h | 1 | 1.622 | b-d | 3 | 5.42 | a-c | 3 | 3.42 | a-b |
| 8 | 3 | 16.7 | a-h | 3 | 8.3 | a-h | 3 | 226.8 | b-g | 2 | 1.726 | b-d | 3 | 3.75 | a-g | 3 | 3.19 | a-b |
| A80190 + Example No. 57 | | | | | | | | | | | | | | | | | | |
| 4+2 | 3 | 25.0 | a-e | 3 | 25.0 | a-d | 3 | 245.4 | a-g | 1 | 1.814 | b-c | 3 | 4.94 | a-c | 3 | 3.56 | a-b |
| 4+4 | 3 | 8.3 | a-h | 3 | 8.3 | a-h | 3 | 262.9 | a-f | 2 | 1.684 | b-d | 3 | 3.25 | b-h | 3 | 3.33 | a-b |
| 4+8 | 3 | 0.0 | h | 3 | 0.0 | h | 3 | 282.8 | a-e | 3 | 1.584 | b-d | 3 | 0.08 | h | 3 | 2.25 | b-d |
| 8+2 | 3 | 25.0 | a-e | 3 | 25.0 | a-d | 3 | 243.0 | a-g | | | | 3 | 3.92 | a-f | 3 | 3.42 | a-b |
| 8+4 | 3 | 8.3 | a-h | 3 | 0.0 | h | 3 | 271.7 | a-f | 2 | 1.609 | b-d | 3 | 1.19 | e-h | 3 | 3.03 | a-b |
| 8+8 | 3 | 8.3 | a-h | 3 | 0.0 | h | 3 | 275.1 | a-f | 2 | 1.570 | b-d | 3 | 0.00 | h | 3 | 1.36 | c-e |
| 16+2 | 3 | 8.3 | a-h | 3 | 8.3 | a-h | 3 | 255.9 | a-g | 2 | 1.725 | b-d | 3 | 3.08 | b-h | 3 | 3.33 | a-b |
| 16+4 | 3 | 0.0 | h | 3 | 0.0 | h | 3 | 289.6 | a-b | 3 | 1.543 | c-d | 3 | 0.00 | h | 3 | 1.25 | d-e |
| 16+8 | 3 | 0.0 | h | 3 | 0.0 | h | 3 | 282.4 | a-f | 3 | 1.619 | b-d | 3 | 0.00 | h | 3 | 0.17 | f |
| A80190 + Example No. 56 | | | | | | | | | | | | | | | | | | |
| 4+2 | 3 | 25.0 | a-e | 3 | 25.0 | a-d | 3 | 249.5 | a-g | 1 | 1.468 | d | 3 | 5.17 | a-c | 3 | 3.42 | a-b |
| 4+4 | 3 | 0.0 | h | 3 | 0.0 | h | 3 | 273.3 | a-f | 3 | 1.589 | b-d | 3 | 2.75 | b-h | 3 | 3.25 | a-b |
| 4+8 | 3 | 8.3 | a-h | 3 | 0.0 | h | 3 | 237.5 | a-g | 2 | 1.663 | b-d | 3 | 1.00 | e-h | 3 | 2.94 | a-b |
| 8+2 | 3 | 8.3 | a-h | 3 | 8.3 | a-h | 3 | 243.8 | a-g | 2 | 1.787 | b-d | 3 | 3.33 | b-h | 3 | 3.67 | a-b |
| 8+4 | 3 | 8.3 | a-h | 3 | 8.3 | a-h | 3 | 246.1 | a-g | 2 | 1.661 | b-d | 3 | 3.25 | b-h | 3 | 3.33 | a-b |

-continued

| | | | | | | | | | | | | | | | | |
|---|---|---|---|---|---|---|---|---|---|---|---|---|---|---|---|---|
| 8+8 | 3 | 0.0 | h | 3 | 0.0 | h | 3 | 270.0 | a–f | 3 | 1.550 | c–d | 3 | 0.58 | f–h | 3 | 2.42 | a–c |
| 16+2 | 3 | 0.0 | h | 3 | 0.0 | h | 3 | 272.7 | a–f | 3 | 1.580 | b–d | 3 | 1.33 | d–h | 3 | 2.42 | a–c |
| 16+4 | 3 | 0.0 | h | 3 | 0.0 | h | 3 | 289.3 | a–c | 3 | 1.480 | c–d | 3 | 0.42 | f–h | 3 | 1.50 | c–e |
| 16+8 | 3 | 0.0 | h | 3 | 0.0 | h | 3 | 283.8 | a–d | 3 | 1.494 | c–d | 3 | 0.25 | g–h | 3 | 0.83 | e–f |

EXPERIMENT NO. 29
Statistical Analyses of Percent Mortality, Weight Gain, Feed/Gain,
Intestinal and Cecal Lesion Scores of broiler cockerels inoculated with
*E. tenella* and *E. maxima*

| Treatment | Mortality Mean | | | | | | Wt. Gain | | | Feed/Gain | | | Lesion Scores | | | | | |
|---|---|---|---|---|---|---|---|---|---|---|---|---|---|---|---|---|---|---|
| | | | | | | | | | | | | | Intestinal | | | Cecal | | |
| PPM | # | Total % | | # | % DTC | | # | Mean | | # | Mean | | # | Mean | | # | Mean | |
| NC | | | | | | | | | | | | | | | | | | |
| 0 | 3 | 0.0 | h | 3 | 0.0 | h | 3 | 320.3 | a | 3 | 1.523 | d–e | 3 | 0.00 | g | 3 | 0.00 | g |
| IC | | | | | | | | | | | | | | | | | | |
| 0 | 3 | 16.7 | a–h | 3 | 16.7 | a–h | 3 | 182.6 | h–j | 2 | 1.973 | a–b | 3 | 9.08 | a | 3 | 3.75 | a–e |
| A80190 | | | | | | | | | | | | | | | | | | |
| 4 | 3 | 25.0 | a–h | 3 | 25.0 | a–g | 3 | 217.8 | c–j | 2 | 1.883 | a–e | 3 | 9.00 | a | 3 | 3.75 | a–e |
| 8 | 3 | 25.0 | a–h | 3 | 25.0 | a–g | 3 | 213.1 | c–j | 2 | 1.955 | a–c | 3 | 7.50 | a–d | 3 | 3.83 | a–e |
| 16 | 3 | 25.0 | a–h | 3 | 16.7 | a–h | 3 | 208.4 | d–j | 1 | 1.943 | a–d | 3 | 7.75 | a–d | 3 | 4.00 | a |
| Example No. 57 | | | | | | | | | | | | | | | | | | |
| 2 | 3 | 25.0 | a–h | 3 | 25.0 | a–g | 3 | 161.4 | j | 1 | 2.083 | a | 3 | 8.58 | a–b | 3 | 3.83 | a–e |
| 4 | 3 | 41.7 | a–b | 3 | 33.3 | a–b | 3 | 172.2 | i–j | | | | 3 | 7.89 | a–d | 3 | 3.56 | a–e |
| 8 | 3 | 8.3 | b–h | 3 | 8.3 | a–h | 3 | 237.4 | b–j | 2 | 1.793 | a–e | 3 | 7.17 | a–d | 3 | 3.67 | a–e |
| Example No. 56 | | | | | | | | | | | | | | | | | | |
| 2 | 3 | 25.0 | a–h | 3 | 25.0 | a–g | 3 | 173.8 | i–j | 1 | 1.789 | a–e | 3 | 7.42 | a–d | 3 | 3.75 | a–e |
| 4 | 3 | 50.0 | a | 3 | 50.0 | a | 3 | 192.9 | f–j | | | | 3 | 7.25 | a–d | 3 | 3.83 | a–e |
| 8 | 3 | 0.0 | h | 3 | 0.0 | h | 3 | 190.1 | g–j | 3 | 2.087 | a | 3 | 6.83 | a–e | 3 | 3.33 | a–e |
| A80190 + Example No. 57 | | | | | | | | | | | | | | | | | | |
| 4+2 | 3 | 25.0 | a–h | 3 | 25.0 | a–g | 3 | 216.5 | c–j | 1 | 1.701 | a–e | 3 | 8.25 | a–c | 3 | 3.92 | a–b |
| 4+4 | 3 | 8.3 | b–h | 3 | 8.3 | a–h | 3 | 239.4 | b–j | 2 | 1.820 | a–e | 3 | 6.00 | a–e | 3 | 3.67 | a–e |
| 4+8 | 3 | 0.0 | h | 3 | 0.0 | h | 3 | 270.4 | a–f | 3 | 1.616 | b–e | 3 | 0.17 | g | 3 | 3.17 | a–e |
| 8+2 | 3 | 25.0 | a–h | 3 | 8.3 | a–h | 3 | 221.0 | c–j | 1 | 1.831 | b–e | 3 | 7.69 | a–d | 3 | 3.89 | a–c |
| 8+4 | 3 | 16.7 | a–h | 3 | 8.3 | a–h | 3 | 250.7 | a–i | 1 | 1.709 | a–e | 3 | 4.56 | b–f | 3 | 3.72 | a–e |
| 8+8 | 3 | 0.0 | h | 3 | 0.0 | h | 3 | 287.0 | a–d | 3 | 1.554 | d–e | 3 | 0.33 | g | 3 | 2.08 | e–f |
| 16+2 | 3 | 16.7 | a–h | 3 | 16.7 | a–h | 3 | 275.2 | a–e | 1 | 1.628 | a–e | 3 | 4.25 | c–f | 3 | 2.75 | b–e |
| 16+4 | 3 | 16.7 | a–h | 3 | 8.3 | a–h | 3 | 263.4 | a–g | 1 | 1.649 | a–e | 3 | 3.17 | e–g | 3 | 2.94 | a–e |
| 16+8 | 3 | 8.3 | b–h | 3 | 0.0 | h | 3 | 291.4 | a–c | 2 | 1.557 | c–e | 3 | 0.00 | g | 3 | 0.44 | g |
| A80190 + Example No. 56 | | | | | | | | | | | | | | | | | | |
| 4+2 | 3 | 25.0 | a–h | 3 | 16.7 | a–h | 3 | 218.1 | c–j | 1 | 1.723 | a–e | 3 | 8.39 | a–c | 3 | 3.44 | a–e |
| 4+4 | 3 | 16.7 | a–h | 3 | 16.7 | a–h | 3 | 232.5 | b–j | 1 | 1.873 | a–e | 3 | 7.75 | a–d | 3 | 3.75 | a–e |
| 4+8 | 3 | 8.3 | b–h | 3 | 8.3 | a–h | 3 | 260.9 | a–h | 2 | 1.584 | b–e | 3 | 4.00 | d–f | 3 | 3.50 | a–e |
| 8+2 | 3 | 8.3 | b–h | 3 | 8.3 | a–h | 3 | 206.1 | e–j | 2 | 1.873 | a–e | 3 | 8.08 | a–d | 3 | 3.58 | a–e |
| 8+4 | 3 | 0.0 | h | 3 | 0.0 | h | 3 | 230.4 | c–j | 3 | 1.752 | a–e | 3 | 5.58 | a–e | 3 | 3.58 | a–e |
| 8+8 | 3 | 0.0 | h | 3 | 0.0 | h | 3 | 292.6 | a–c | 3 | 1.517 | e | 3 | 1.42 | f–g | 3 | 2.08 | e–f |
| 16+2 | 3 | 8.3 | b–h | 3 | 8.3 | a–h | 3 | 248.7 | a–i | 2 | 1.744 | a–e | 3 | 5.25 | a–e | 3 | 3.25 | a–e |
| 16+4 | 3 | 8.3 | b–h | 3 | 0.0 | h | 3 | 267.5 | a–g | 2 | 1.542 | d–e | 3 | 3.22 | e–g | 3 | 2.47 | c–f |
| 16+8 | 3 | 8.3 | b–h | 3 | 0.0 | h | 3 | 308.1 | a–b | 2 | 1.537 | d–e | 3 | 0.17 | g | 3 | 1.17 | f–g |

EXPERIMENT NO. 30
Statistical Analyses of Percent Mortality, Weight Gain, Feed/Gain,
Intestinal and Cecal Lesion Scores of broiler cockerels inoculated with
*E. tenella* and *E. acervulina*

| Treatment | Mortality Mean | | | | | | Wt. Gain | | | Feed/Gain | | | Lesion Scores | | | | | |
|---|---|---|---|---|---|---|---|---|---|---|---|---|---|---|---|---|---|---|
| | | | | | | | | | | | | | Intestinal | | | Cecal | | |
| PPM | # | Total % | | # | % DTC | | # | Mean | | # | Mean | | # | Mean | | # | Mean | |
| NC | | | | | | | | | | | | | | | | | | |
| 0 | 4 | 0.0 | e | 4 | 0.0 | a | 4 | 330.6 | a | 4 | 1.394 | d | 4 | 0.00 | f | 4 | 0.00 | e |
| IC | | | | | | | | | | | | | | | | | | |
| 0 | 4 | 0.0 | e | 4 | 0.0 | a | 4 | 276.3 | d–e | 4 | 1.641 | a–b | 4 | 5.88 | a | 4 | 3.56 | a–b |
| A80190 | | | | | | | | | | | | | | | | | | |
| 10 | 4 | 0.0 | e | 4 | 0.0 | a | 4 | 293.4 | a–e | 4 | 1.515 | a–d | 4 | 5.19 | a–b | 4 | 3.00 | a–c |

-continued

| | | | | | | | | | | | | | | | | | |
|---|---|---|---|---|---|---|---|---|---|---|---|---|---|---|---|---|---|
| 20 | 4 | 0.0 | e | 4 | 0.0 | a | 4 | 300.4 | a-e | 4 | 1.449 | c-d | 4 | 3.56 | b-d | 4 | 3.00 | a-c |
| 30 | 4 | 12.5 | a-c | 4 | 0.0 | a | 4 | 313.9 | a-c | 3 | 1.450 | c-d | 4 | 2.06 | d-f | 4 | 3.00 | a-c |
| 40 | 4 | 0.0 | e | 4 | 0.0 | a | 4 | 321.9 | a-b | 4 | 1.391 | d | 4 | 2.38 | c-e | 4 | 2.44 | a-c |

Example No. 57

| | | | | | | | | | | | | | | | | | |
|---|---|---|---|---|---|---|---|---|---|---|---|---|---|---|---|---|---|
| 2 | 4 | 0.0 | e | 4 | 0.0 | a | 4 | 270.8 | e | 4 | 1.662 | a | 4 | 5.81 | a | 4 | 3.69 | a |
| 4 | 4 | 0.0 | e | 4 | 0.0 | a | 4 | 284.4 | a-e | 4 | 1.583 | a-c | 4 | 4.81 | a-b | 4 | 3.56 | a-b |
| 6 | 4 | 0.0 | e | 4 | 0.0 | a | 4 | 277.8 | b-e | 4 | 1.568 | a-d | 4 | 4.75 | a-b | 4 | 2.38 | a-c |
| 8 | 4 | 12.5 | a-c | 4 | 0.0 | a | 4 | 277.2 | b-e | 2 | 1.617 | a-c | 4 | 4.06 | a-c | 4 | 2.48 | a-c |

A80190 + Example No. 57

| | | | | | | | | | | | | | | | | | |
|---|---|---|---|---|---|---|---|---|---|---|---|---|---|---|---|---|---|
| 10+2 | 4 | 0.0 | e | 4 | 0.0 | a | 4 | 283.6 | a-e | 4 | 1.543 | a-d | 4 | 4.06 | a-c | 4 | 3.13 | a-c |
| 10+4 | 4 | 0.0 | e | 4 | 0.0 | a | 4 | 301.3 | a-e | 4 | 1.437 | c-d | 4 | 2.44 | c-e | 4 | 2.69 | a-c |
| 10+6 | 4 | 6.3 | a-e | 4 | 0.0 | a | 4 | 276.5 | b-e | 3 | 1.559 | a-d | 4 | 2.04 | d-f | 4 | 2.29 | b-c |
| 10+8 | 4 | 0.0 | e | 4 | 0.0 | a | 4 | 280.6 | a-e | 4 | 1.566 | a-d | 4 | 1.19 | e-f | 4 | 1.00 | d-e |
| 20+2 | 4 | 0.0 | e | 4 | 0.0 | a | 4 | 306.9 | a-e | 4 | 1.430 | c-d | 4 | 1.63 | e-f | 4 | 2.56 | a-c |
| 20+4 | 4 | 0.0 | e | 4 | 0.0 | a | 4 | 291.8 | a-e | 4 | 1.514 | a-d | 4 | 1.69 | e-f | 4 | 1.75 | c-d |
| 20+6 | 4 | 0.0 | e | 4 | 0.0 | a | 4 | 289.5 | a-e | 4 | 1.508 | a-d | 4 | 0.88 | e-f | 4 | 1.00 | d-e |
| 20+8 | 4 | 6.3 | a-e | 4 | 0.0 | a | 4 | 276.5 | c-e | 3 | 1.498 | a-d | 4 | 0.29 | f | 4 | 1.13 | d-e |
| 30+2 | 4 | 12.5 | a-c | 4 | 0.0 | a | 4 | 296.3 | a-e | 2 | 1.487 | a-d | 4 | 1.71 | e-f | 4 | 2.52 | a-c |
| 30+4 | 4 | 0.0 | e | 4 | 0.0 | a | 4 | 289.7 | a-e | 4 | 1.504 | a-d | 4 | 1.06 | e-f | 4 | 1.13 | d-e |
| 30+6 | 4 | 0.0 | e | 4 | 0.0 | a | 4 | 303.2 | a-e | 4 | 1.520 | a-d | 4 | 0.25 | f | 4 | 0.56 | d-e |
| 30+8 | 4 | 0.0 | e | 4 | 0.0 | a | 4 | 278.3 | b-e | 4 | a.528 | a-d | 4 | 0.19 | f | 4 | 0.44 | e |
| 40+2 | 4 | 0.0 | e | 4 | 0.0 | a | 4 | 303.3 | a-e | 4 | 1.448 | c-d | 4 | 0.81 | e-f | 4 | 1.75 | c-d |
| 40+4 | 4 | 0.0 | e | 4 | 0.0 | a | 4 | 311.1 | a-d | 4 | 1.451 | b-d | 4 | 0.06 | f | 4 | 0.19 | e |
| 40+6 | 4 | 0.0 | e | 4 | 0.0 | a | 4 | 286.8 | a-e | 4 | 1.571 | a-d | 4 | 0.19 | f | 4 | 0.25 | e |
| 40+8 | 4 | 0.0 | e | 4 | 0.0 | a | 4 | 296.6 | a-e | 4 | 1.475 | b-d | 4 | 0.00 | f | 4 | 0.00 | e |

EXPERIMENT NO. 31
Statistical Analyses of Percent Mortality, Weight Gain, Feed/Gain,
Intestinal and Cecal Lesion Scores of broiler cockerels inoculated with
*E. tenella* and *E. acervulina*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 4 | 0.0 | e | 4 | 0.0 | e | 4 | 332.1 | a | 4 | 1.439 | f | 4 | 0.00 | g | 4 | 0.00 | g |
| IC | | | | | | | | | | | | |
| 0 | 4 | 0.0 | e | 4 | 0.0 | e | 4 | 283.9 | a-e | 4 | 1.688 | a-c | 4 | 5.56 | a | 4 | 3.00 | a-c |

A80190 + Example No. 57

| | | | | | | | | | | | | | | | | | |
|---|---|---|---|---|---|---|---|---|---|---|---|---|---|---|---|---|---|
| 2+2 | 4 | 6.3 | a-e | 4 | 0.0 | e | 4 | 285.4 | a-e | 3 | 1.621 | a-f | 4 | 5.31 | a | 4 | 3.21 | a-b |
| 2+4 | 4 | 0.0 | e | 4 | 0.0 | e | 4 | 280.3 | a-e | 4 | 1.758 | a | 4 | 3.94 | a-c | 4 | 3.13 | a-c |
| 2+8 | 4 | 0.0 | e | 4 | 0.0 | e | 4 | 280.8 | a-e | 4 | 1.637 | a-e | 4 | 2.31 | c-g | 4 | 2.00 | b-d |
| 4+2 | 4 | 0.0 | e | 4 | 0.0 | e | 4 | 285.4 | a-e | 4 | 1.657 | a-d | 4 | 4.69 | a-b | 4 | 3.06 | a-c |
| 4+4 | 4 | 0.0 | e | 4 | 0.0 | e | 4 | 301.2 | a-e | 4 | 1.545 | c-f | 4 | 3.50 | a-d | 4 | 3.50 | a |
| 4+8 | 4 | 0.0 | e | 4 | 0.0 | e | 4 | 289.6 | a-e | 4 | 1.605 | a-f | 4 | 1.25 | d-g | 4 | 1.38 | d-f |
| 8+2 | 4 | 0.0 | e | 4 | 0.0 | e | 4 | 284.8 | a-e | 4 | 1.604 | a-f | 4 | 4.06 | a-c | 4 | 3.38 | a |
| 8+4 | 4 | 0.0 | e | 4 | 0.0 | e | 4 | 296.9 | a-e | 4 | 1.574 | b-f | 4 | 3.13 | b-c | 4 | 3.13 | a-c |
| 8+8 | 4 | 0.0 | e | 4 | 0.0 | e | 4 | 274.3 | d-e | 4 | 1.572 | b-f | 4 | 0.81 | e-g | 4 | 0.75 | e-g |
| 16+2 | 4 | 0.0 | e | 4 | 0.0 | e | 4 | 323.2 | a-b | 4 | 1.476 | e-f | 4 | 2.81 | bn-f | 4 | 3.38 | a |
| 16+4 | 4 | 0.0 | e | 4 | 0.0 | e | 4 | 298.3 | a-e | 4 | 1.635 | a-e | 4 | 2.13 | c-g | 4 | 3.13 | a-c |
| 16+8 | 4 | 0.0 | e | 4 | 0.0 | e | 4 | 274.6 | c-e | 4 | 1.558 | b-f | 4 | 0.56 | f-g | 4 | 0.56 | e-g |

A82810 + Example No. 57

| | | | | | | | | | | | | | | | | | |
|---|---|---|---|---|---|---|---|---|---|---|---|---|---|---|---|---|---|
| 2+2 | 4 | 0.0 | e | 4 | 0.0 | e | 4 | 296.0 | a-e | 4 | 1.567 | b-f | 4 | 3.50 | a-d | 4 | 3.13 | a-c |
| 2+4 | 4 | 0.0 | e | 4 | 0.0 | e | 4 | 300.3 | a-e | 4 | 1.549 | c-f | 4 | 4.06 | a-c | 4 | 3.06 | a-c |
| 2+8 | 4 | 6.3 | a-e | 4 | 0.0 | e | 4 | 290.6 | a-e | 3 | 1.614 | a-f | 4 | 0.06 | g | 4 | 0.38 | e-g |
| 4+2 | 4 | 6.3 | a-e | 4 | 0.0 | e | 4 | 320.4 | a-c | 3 | 1.513 | c-f | 4 | 2.54 | b-f | 4 | 3.06 | a-c |
| 4+4 | 4 | 0.0 | e | 4 | 0.0 | e | 4 | 305.3 | a-e | 4 | 1.538 | c-f | 4 | 1.88 | c-g | 4 | 1.88 | c-d |
| 4+8 | 4 | 0.0 | e | 4 | 0.0 | e | 4 | 291.1 | a-e | 4 | 1.600 | a-f | 4 | 0.00 | g | 4 | 0.25 | e-g |
| 8+2 | 4 | 0.0 | e | 4 | 0.0 | e | 4 | 312.3 | a-d | 4 | 1.506 | d-f | 4 | 2.94 | b-e | 4 | 1.50 | d-f |
| 8+4 | 4 | 6.3 | a-e | 4 | 6.3 | a | 4 | 303.1 | a-e | 3 | 1.553 | b-f | 4 | 1.25 | d-g | 4 | 1.44 | d-f |
| 8+8 | 4 | 0.0 | e | 4 | 0.0 | e | 4 | 282.1 | a-e | 4 | 1.579 | b-f | 4 | 0.19 | g | 4 | 0.19 | f-g |
| 16+2 | 4 | 0.0 | e | 4 | 0.0 | e | 4 | 276.6 | b-e | 4 | 1.616 | a-f | 4 | 0.06 | g | 4 | 0.38 | e-g |
| 16+4 | 4 | 6.3 | a-e | 4 | 0.0 | e | 4 | 308.3 | a-e | 3 | 1.526 | c-f | 4 | 1.06 | e-g | 4 | 0.56 | e-g |
| 16+8 | 4 | 0.0 | e | 4 | 0.0 | e | 4 | 256.4 | e | 4 | 1.732 | a-b | 4 | 0.00 | g | 4 | 0.00 | g |

EXPERIMENT NO. 32
Statistical Analyses of Percent Mortality, Weight Gain, Feed/Gain,
Intestinal and Cecal Lesion Scores of broiler cockerels inoculated with
*E. tenella* and *E. maxima*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 4 | 0.0 e | 4 | 0.0 a | 4 | 318.6 a | 4 | 1.467 b–e | 4 | 1.63 i–j | 4 | 0.13 g |
| IC | | | | | | | | | | | | |
| 0 | 4 | 6.3 a–c | 4 | 0.0 a | 4 | 274.0 b–f | 3 | 1.588 a–e | 4 | 8.29 a | 4 | 3.29 a |
| A80190 + Example No. 57 | | | | | | | | | | | | |
| 2+2 | 4 | 0.0 e | 4 | 0.0 a | 4 | 258.3 f | 4 | 1.599 a–c | 4 | 7.88 a–b | 4 | 2.94 a–c |
| 2+4 | 4 | 0.0 e | 4 | 0.0 a | 4 | 256.2 f | 4 | 1.651 a | 4 | 6.31 a–f | 4 | 3.31 a |
| 2+8 | 4 | 0.0 e | 4 | 0.0 a | 4 | 269.0 d–f | 4 | 1.582 a–e | 4 | 5.13 a–h | 4 | 2.50 a–d |
| 4+2 | 4 | 6.3 a–c | 4 | 0.0 a | 4 | 272.1 c–f | 3 | 1.611 a–b | 4 | 7.31 a–c | 4 | 3.56 a |
| 4+4 | 4 | 0.0 e | 4 | 0.0 a | 4 | 292.7 a–f | 4 | 1.528 a–e | 4 | 6.25 a–f | 4 | 3.19 a–b |
| 4+8 | 4 | 0.0 e | 4 | 0.0 a | 4 | 280.0 b–f | 4 | 1.578 a–e | 4 | 4.50 c–i | 4 | 2.06 b–d |
| 8+2 | 4 | 0.0 e | 4 | 0.0 a | 4 | 265.8 e–f | 4 | 1.577 a–e | 4 | 7.44 a–c | 4 | 3.00 a–c |
| 8+4 | 4 | 0.0 e | 4 | 0.0 a | 4 | 275.5 b–f | 4 | 1.542 a–e | 4 | 6.13 a–f | 4 | 2.88 a–c |
| 8+8 | 4 | 0.0 e | 4 | 0.0 a | 4 | 274.7 b–f | 4 | 1.571 a–c | 4 | 3.69 d–j | 4 | 0.94 e–g |
| 16+2 | 4 | 0.0 e | 4 | 0.0 a | 4 | 285.9 a–f | 4 | 1.560 a–e | 4 | 7.06 a–c | 4 | 3.00 a–c |
| 16+4 | 4 | 0.0 e | 4 | 0.0 a | 4 | 296.9 a–e | 4 | 1.512 a–e | 4 | 5.44 a–g | 4 | 2.06 b–d |
| 16+8 | 4 | 0.0 e | 4 | 0.0 a | 4 | 286.8 a–f | 4 | 1.566 a–e | 4 | 3.50 e–j | 4 | 0.88 e–g |
| A82810 + Example No. 57 | | | | | | | | | | | | |
| 2+2 | 4 | 0.0 e | 4 | 0.0 a | 4 | 289.0 a–f | 4 | 1.573 a–e | 4 | 7.13 a–c | 4 | 3.38 a |
| 2+4 | 4 | 0.0 e | 4 | 0.0 a | 4 | 301.3 a–e | 4 | 1.505 a–e | 4 | 6.50 a–e | 4 | 3.25 a |
| 2+8 | 4 | 0.0 e | 4 | 0.0 a | 4 | 285.5 a–f | 4 | 1.595 a–e | 4 | 3.19 f–j | 4 | 0.88 e–g |
| 4+2 | 4 | 0.0 e | 4 | 0.0 a | 4 | 306.3 a–d | 4 | 1.490 a–e | 4 | 6.81 a–d | 4 | 3.31 a |
| 4+4 | 4 | 0.0 e | 4 | 0.0 a | 4 | 309.1 a–c | 4 | 1.455 c–e | 4 | 4.81 b–h | 4 | 1.63 d–f |
| 4+8 | 4 | 0.0 e | 4 | 0.0 a | 4 | 287.3 a–f | 4 | 1.488 a–e | 4 | 2.88 g–j | 4 | 0.63 f–g |
| 8+2 | 4 | 6.3 a–c | 4 | 0.0 a | 4 | 311.7 a–b | 3 | 1.450 d–e | 4 | 6.04 a–f | 4 | 1.88 c–e |
| 8+4 | 4 | 0.0 e | 4 | 0.0 a | 4 | 305.3 a–d | 4 | 1.445 e | 4 | 3.75 d–j | 4 | 0.81 e–g |
| 8+8 | 4 | 0.0 e | 4 | 0.0 a | 4 | 281.6 a–f | 4 | 1.513 a–e | 4 | 1.56 i–j | 4 | 0.56 f–g |
| 16+2 | 4 | 0.0 e | 4 | 0.0 a | 4 | 290.0 a–f | 4 | 1.535 a–e | 4 | 3.81 d–j | 4 | 0.56 f–g |
| 16+4 | 4 | 0.0 e | 4 | 0.0 a | 4 | 282.4 a–f | 4 | 1.568 a–e | 4 | 2.06 h–j | 4 | 0.50 f–g |
| 16+8 | 4 | 0.0 e | 4 | 0.0 a | 4 | 265.6 e–f | 4 | 1.596 a–d | 4 | 0.75 j | 4 | 0.00 g |

EXPERIMENT NO. 33
Statistical Analyses of Percent Mortality, Weight Gain, Feed/Gain,
Intestinal and Cecal Lesion Scores of broiler cockerels inoculated with
*E. tenella* and *E. maxima*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 4 | 0.0 e | 4 | 0.0 a | 4 | 341.1 a | 4 | 1.395 c–e | 4 | 2.00 d–f | 4 | 0.06 f |
| IC | | | | | | | | | | | | |
| 0 | 4 | 0.0 e | 4 | 0.0 a | 4 | 314.8 a–d | 4 | 1.439 a–e | 4 | 6.44 a | 4 | 2.44 a–b |
| A80190 | | | | | | | | | | | | |
| 10 | 4 | 0.0 e | 4 | 0.0 a | 4 | 325.6 a–c | 4 | 1.429 a–e | 4 | 5.88 a–b | 4 | 2.69 a |
| 20 | 4 | 0.0 e | 4 | 0.0 a | 4 | 310.7 a–e | 4 | 1.377 e | 4 | 5.69 a–b | 4 | 2.44 a–b |
| 30 | 4 | 0.0 e | 4 | 0.0 a | 4 | 294.6 b–e | 4 | 1.430 a–e | 4 | 5.56 a–c | 4 | 2.31 a–b |
| 40 | 4 | 0.0 e | 4 | 0.0 a | 4 | 308.6 a–e | 4 | 1.436 a–e | 4 | 4.69 a–f | 4 | 2.06 a–b |
| Example No. 57 | | | | | | | | | | | | |
| 2 | 4 | 0.0 e | 4 | 0.0 a | 4 | 296.5 a–e | 4 | 1.466 a–e | 4 | 5.31 a–d | 4 | 2.19 a–b |
| 4 | 4 | 0.0 e | 4 | 0.0 a | 4 | 283.2 b–e | 4 | 1.500 a–e | 4 | 5.81 a–b | 4 | 2.19 a–b |
| 6 | 4 | 0.0 e | 4 | 0.0 a | 4 | 290.4 b–e | 4 | 1.470 a–e | 4 | 6.50 a | 4 | 2.31 a–b |
| 8 | 4 | 0.0 e | 4 | 0.0 a | 4 | 267.3 e | 4 | 1.593 a | 4 | 3.88 a–f | 4 | 1.25 b–f |
| A80190 + Example No. 57 | | | | | | | | | | | | |
| 10+2 | 4 | 0.0 e | 4 | 0.0 a | 4 | 314.7 a–d | 4 | 1.437 a–e | 4 | 5.44 a–c | 4 | 2.19 a–b |
| 10+4 | 4 | 0.0 e | 4 | 0.0 a | 4 | 296.7 a–e | 4 | 1.481 a–e | 4 | 5.00 a–e | 4 | 2.13 a–b |
| 10+6 | 4 | 0.0 e | 4 | 0.0 a | 4 | 295.1 b–e | 4 | 1.550 a–c | 4 | 4.75 a–f | 4 | 2.13 a–b |

-continued

| | | | | | | | | | | | | | | | | |
|---|---|---|---|---|---|---|---|---|---|---|---|---|---|---|---|---|
| 10+8 | 4 | 0.0 | e | 4 | 0.0 | a | 4 | 280.6 | c-e | 4 | 1.566 | a-b | 4 | 2.69 | b-f | 4 | 0.56 | c-f |
| 20+2 | 4 | 0.0 | e | 4 | 0.0 | a | 4 | 305.7 | a-e | 4 | 1.408 | b-e | 4 | 4.81 | a-f | 4 | 2.19 | a-b |
| 20+4 | 4 | 0.0 | e | 4 | 0.0 | a | 4 | 304.9 | a-e | 4 | 1.465 | a-e | 4 | 3.50 | a-f | 4 | 1.44 | a-e |
| 20+6 | 4 | 0.0 | e | 4 | 0.0 | a | 4 | 298.7 | a-e | 4 | 1.452 | a-e | 4 | 4.44 | a-f | 4 | 1.50 | a-d |
| 20+8 | 4 | 0.0 | e | 4 | 0.0 | a | 4 | 288.0 | b-e | 4 | 1.515 | a-e | 4 | 2.56 | b-f | 4 | 0.19 | f |
| 30+2 | 4 | 0.0 | e | 4 | 0.0 | a | 4 | 308.7 | a-e | 4 | 1.414 | a-e | 4 | 4.44 | a-f | 4 | 1.69 | a-c |
| 30+4 | 4 | 0.0 | e | 4 | 0.0 | a | 4 | 297.7 | a-e | 4 | 1.456 | a-e | 4 | 4.06 | a-f | 4 | 0.75 | c-f |
| 30+6 | 4 | 0.0 | e | 4 | 0.0 | a | 4 | 296.6 | a-e | 4 | 1.484 | a-e | 4 | 2.19 | c-f | 4 | 0.44 | d-f |
| 30+8 | 4 | 0.0 | e | 4 | 0.0 | a | 4 | 280.2 | d-e | 4 | 1.494 | a-e | 4 | 1.50 | f | 4 | 0.13 | f |
| 40+2 | 4 | 0.0 | e | 4 | 0.0 | a | 4 | 327.7 | a-b | 4 | 1.377 | e | 4 | 4.50 | a-f | 4 | 0.81 | c-f |
| 40+4 | 4 | 6.3 | a | 4 | 0.0 | a | 4 | 302.8 | a-e | 3 | 1.450 | a-e | 4 | 3.60 | a-f | 4 | 0.69 | c-f |
| 40+6 | 4 | 0.0 | e | 4 | 0.0 | a | 4 | 301.6 | a-e | 4 | 1.537 | a-d | 4 | 1.88 | e-f | 4 | 0.31 | e-f |
| 40+8 | 4 | 0.0 | e | 4 | 0.0 | a | 4 | 294.0 | b-e | 4 | 1.533 | a-e | 4 | 1.63 | e-f | 4 | 0.25 | f |

EXPERIMENT NO. 34
Statistical Analyses of Percent Mortality, Weight Gain, Feed/Gain,
Intestinal and Cecal Lesion Scores of broiler cockerels inoculated with
*E. tenella* and *E. acervulina*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 4 | 0.0 | a | 4 | 0.0 | a | 4 | 326.7 | a | 4 | 1.352 | d | 4 | 0.00 | f | 4 | 0.00 | e |
| IC | | | | | | | | | | | | |
| 0 | 4 | 0.0 | a | 4 | 0.0 | a | 4 | 279.3 | b-e | 4 | 1.613 | a-c | 4 | 5.88 | a | 4 | 3.50 | a-b |
| A80190 | | | | | | | | | | | | |
| 20 | 4 | 0.0 | a | 4 | 0.0 | a | 4 | 299.3 | a-e | 4 | 1.549 | a-c | 4 | 3.75 | c | 4 | 3.50 | a-b |
| 40 | 4 | 0.0 | a | 4 | 0.0 | a | 4 | 317.5 | a-b | 4 | 1.447 | b-d | 4 | 0.94 | e-f | 4 | 1.13 | d |
| 60 | 4 | 6.3 | a | 4 | 0.0 | a | 4 | 287.7 | a-e | 3 | 1.547 | a-c | 4 | 0.35 | f | 4 | 0.58 | d-e |
| Example No. 57 | | | | | | | | | | | | |
| 2 | 4 | 0.0 | a | 4 | 0.0 | a | 4 | 266.2 | c-e | 4 | 1.625 | a-b | 4 | 5.75 | a | 4 | 3.63 | a |
| 3 | 4 | 0.0 | a | 4 | 0.0 | a | 4 | 274.2 | b-e | 4 | 1.635 | a | 4 | 5,19 | a-b | 4 | 3.44 | a-b |
| 4 | 4 | 6.3 | a | 4 | 6.3 | a | 4 | 262.1 | d-e | 3 | 1.617 | a-c | 4 | 5.56 | a | 4 | 3.19 | a-b |
| 5 | 4 | 0.0 | a | 4 | 0.0 | a | 4 | 267.3 | c-e | 4 | 1.579 | a-c | 4 | 4.63 | b | 4 | 3.50 | a-b |
| A80190 + Example No. 57 | | | | | | | | | | | | |
| 20+2 | 4 | 0.0 | a | 4 | 0.0 | a | 4 | 295.5 | a-e | 4 | 1.507 | a-d | 4 | 2.19 | d | 4 | 3.56 | a-b |
| 20+3 | 4 | 6.3 | a | 4 | 0.0 | a | 4 | 294.2 | a-e | 4 | 1.493 | a-d | 4 | 1.50 | d-e | 4 | 2.65 | b-c |
| 20+4 | 4 | 0.0 | a | 4 | 0.0 | a | 4 | 312.6 | a-c | 4 | 1.450 | b-d | 4 | 1.19 | e-f | 4 | 2.06 | c |
| 20+5 | 4 | 0.0 | a | 4 | 0.0 | a | 4 | 297.3 | a-e | 4 | 1.472 | a-d | 4 | 0.38 | f | 4 | 1.19 | d |
| 40+2 | 4 | 0.0 | a | 4 | 0.0 | a | 4 | 311.5 | a-c | 3 | 1.432 | c-d | 4 | 0.19 | f | 4 | 0.69 | d-e |
| 40+3 | 4 | 0.0 | a | 4 | 0.0 | a | 4 | 306.4 | a-d | 4 | 1.448 | b-d | 4 | 0.63 | e-f | 4 | 0.50 | d-e |
| 40+4 | 4 | 0.0 | a | 4 | 0.0 | a | 4 | 271.3 | b-e | 4 | 1.580 | a-c | 4 | 0.31 | f | 4 | 0.44 | d-e |
| 40+5 | 4 | 0.0 | a | 4 | 0.0 | a | 4 | 297.4 | a-e | 4 | 1.436 | c-d | 4 | 0.13 | f | 4 | 0.25 | d-e |
| 60+2 | 4 | 12.5 | a | 4 | 0.0 | a | 4 | 279.5 | b-e | 2 | 1.381 | c-d | 4 | 0.00 | f | 4 | 0.13 | e |
| 60+3 | 4 | 6.3 | a | 4 | 0.0 | a | 4 | 277.9 | b-e | 3 | 1.555 | a-c | 4 | 0.13 | f | 4 | 0.15 | e |
| 60+4 | 4 | 0.0 | a | 4 | 0.0 | a | 4 | 254.1 | e | 4 | 1.634 | a | 4 | 0.00 | f | 4 | 0.06 | e |
| 60+5 | 4 | 0.0 | a | 4 | 0.0 | a | 4 | 260.6 | d-e | 4 | 1.590 | a-c | 4 | 0.00 | f | 4 | 0.00 | e |

EXPERIMENT NO. 35
Statistical Analyses of Percent Mortality, Weight Gain, Feed/Gain,
Intestinal and Cecal Lesion Scores of broiler cockerels inoculated with
*E. tenella* and *E. maxima*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 4 | 0.0 | b | 4 | 0.0 | a | 4 | 332.1 | a-c | 4 | 1.482 | a-c | 4 | 0.81 | e | 4 | 0.00 | f |
| IC | | | | | | | | | | | | |
| 0 | 4 | 0.0 | b | 4 | 0.0 | a | 4 | 308.2 | a-d | 4 | 1.523 | a-c | 4 | 7.13 | a | 4 | 2.56 | a-b |
| A80190 | | | | | | | | | | | | |
| 20 | 4 | 0.0 | b | 4 | 0.0 | a | 4 | 312.4 | a-d | 4 | 1.544 | a-c | 4 | 5.81 | a-b | 4 | 2.13 | b-c |
| 40 | 4 | 0.0 | b | 4 | 0.0 | a | 4 | 338.1 | a-b | 4 | 1.405 | b-c | 4 | 4.06 | b-d | 4 | 1.19 | d-e |
| 60 | 4 | 0.0 | b | 4 | 0.0 | a | 4 | 277.1 | d | 4 | 1.655 | a | 4 | 1.94 | d-e | 4 | 0.63 | e-f |

| Example No. 57 | | | | | | | | | | | | | | | | | |
|---|---|---|---|---|---|---|---|---|---|---|---|---|---|---|---|---|---|
| 2 | 4 | 18.8 | a | 4 | 12.5 | a | 4 | 282.4 | d | 2 | 1.609 | a–c | 4 | 6.65 | a–b | 4 | 3.27 | a |
| 3 | 4 | 6.3 | a–b | 4 | 6.3 | a | 4 | 275.5 | d | 3 | 1.526 | a–c | 4 | 6.56 | a–b | 4 | 2.75 | a–b |
| 4 | 4 | 0.0 | b | 4 | 0.0 | a | 4 | 285.3 | d | 4 | 1.554 | a–c | 4 | 5.81 | a–b | 4 | 2.38 | b |
| 5 | 4 | 0.0 | b | 4 | 0.0 | a | 4 | 296.8 | b–d | 4 | 1.542 | a–c | 4 | 5.69 | a–b | 4 | 2.06 | b–d |
| A80190 + Example No. 57 | | | | | | | | | | | | | | | | | |
| 20+2 | 4 | 6.3 | a–b | 4 | 0.0 | a | 4 | 314.7 | a–d | 3 | 1.523 | a–c | 3 | 5.06 | a–c | 4 | 1.92 | b–d |
| 20+3 | 4 | 0.0 | b | 4 | 0.0 | a | 4 | 312.2 | a–d | 4 | 1.501 | a–c | 4 | 4.94 | a–c | 4 | 1.81 | b–d |
| 20+4 | 4 | 0.0 | b | 4 | 0.0 | a | 4 | 318.4 | a–d | 4 | 1.493 | a–c | 4 | 4.25 | a–d | 4 | 1.25 | c–e |
| 20+5 | 4 | 0.0 | b | 4 | 0.0 | a | 4 | 309.1 | a–d | 4 | 1.493 | a–c | 4 | 2.88 | c–e | 4 | 0.81 | e–f |
| 40+2 | 4 | 0.0 | b | 4 | 0.0 | a | 4 | 346.9 | a | 4 | 1.381 | c | 4 | 2.19 | d–e | 4 | 0.63 | e–f |
| 40+3 | 4 | 0.0 | b | 4 | 0.0 | a | 4 | 313.5 | a–d | 4 | 1.500 | a–c | 4 | 2.06 | d–e | 4 | 0.31 | e–f |
| 40+4 | 4 | 0.0 | b | 4 | 0.0 | a | 4 | 308.3 | a–d | 4 | 1.487 | a–c | 4 | 2.00 | d–e | 4 | 0.44 | e–f |
| 40+5 | 4 | 0.0 | b | 4 | 0.0 | a | 4 | 289.5 | c–d | 3 | 1.536 | a–c | 4 | 1.13 | e | 4 | 0.13 | f |
| 60+2 | 4 | 6.3 | a–b | 4 | 0.0 | a | 4 | 300.6 | b–d | 3 | 1.612 | a–b | 4 | 1.27 | e | 4 | 0.29 | e–f |
| 60+3 | 4 | 0.0 | b | 4 | 0.0 | a | 4 | 296.1 | b–d | 4 | 1.546 | a–c | 4 | 0.56 | e | 4 | 0.25 | e–f |
| 60+4 | 4 | 0.0 | b | 4 | 0.0 | a | 4 | 289.3 | c–d | 4 | 1.621 | a | 4 | 0.13 | e | 4 | 0.00 | f |
| 60+5 | 4 | 0.0 | b | 4 | 0.0 | a | 4 | 275.6 | d | 4 | 1.624 | a | 4 | 0.75 | e | 4 | 0.06 | f |

EXPERIMENT NO. 36
Statistical Analyses of Percent Mortality, Weight Gain, Feed/Gain,
Intestinal and Cecal Lesion Scores of broiler cockerels inoculated with
*E. tenella* and *E. acervulina*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 4 | 6.3 | a | 4 | 0.0 | a | 4 | 318.4 | a | 4 | 1.358 | d | 4 | 0.00 | f | 4 | 0.00 | e |
| IC | | | | | | | | | | | | |
| 0 | 4 | 0.0 | a | 4 | 0.0 | a | 4 | 257.7 | c–d | 4 | 1.676 | a–b | 4 | 5.75 | a | 4 | 3.50 | a |
| Monensin | | | | | | | | | | | | |
| 20 | 4 | 6.3 | a | 4 | 0.0 | a | 4 | 277.0 | a–d | 4 | 1.604 | a–c | 4 | 4.44 | a–b | 4 | 3.21 | a–b |
| 40 | 4 | 0.0 | a | 4 | 0.0 | a | 4 | 280.0 | a–d | 4 | 1.550 | a–d | 4 | 3.38 | b–c | 4 | 3.38 | a |
| 60 | 4 | 0.0 | a | 4 | 0.0 | a | 4 | 281.8 | a–d | 4 | 1.527 | a–d | 4 | 3.25 | b–c | 4 | 3.56 | a |
| 80 | 4 | 0.0 | a | 4 | 0.0 | a | 4 | 306.3 | a–b | 4 | 1.445 | c–d | 4 | 2.25 | c–e | 4 | 3.19 | a–b |
| Example No. 57 | | | | | | | | | | | | |
| 2 | 4 | 0.0 | a | 4 | 0.0 | a | 4 | 249.3 | d | 4 | 1.695 | a | 4 | 5.88 | a | 4 | 3.38 | a |
| 4 | 4 | 0.0 | a | 4 | 0.0 | a | 4 | 270.2 | b–d | 4 | 1.594 | a–c | 4 | 5.31 | a | 4 | 2.81 | a–c |
| 6 | 4 | 0.0 | a | 4 | 0.0 | a | 4 | 263.5 | b–d | 4 | 1.588 | a–c | 4 | 4.44 | a–b | 4 | 3.13 | a–b |
| Monensin + Example No. 57 | | | | | | | | | | | | |
| 20+2 | 4 | 0.0 | a | 4 | 0.0 | a | 4 | 289.0 | a–d | 4 | 1.497 | a–d | 4 | 2.81 | b–d | 4 | 3.44 | a |
| 20+4 | 4 | 0.0 | a | 4 | 0.0 | a | 4 | 291.9 | a–d | 4 | 1.450 | c–d | 4 | 3.25 | b–c | 4 | 3.13 | a–b |
| 20+6 | 4 | 0.0 | a | 4 | 0.0 | a | 4 | 277.9 | a–d | 4 | 1.556 | a–d | 4 | 2.06 | c–e | 4 | 1.81 | c–d |
| 40+2 | 4 | 0.0 | a | 4 | 0.0 | a | 4 | 289.8 | a–d | 4 | 1.492 | a–d | 4 | 2.94 | b–d | 4 | 3.19 | a–b |
| 40+4 | 4 | 0.0 | a | 4 | 0.0 | a | 4 | 298.7 | a–c | 4 | 1.463 | b–d | 4 | 2.31 | c–e | 4 | 2.50 | a–d |
| 40+6 | 4 | 0.0 | a | 4 | 0.0 | a | 4 | 285.0 | a–d | 4 | 1.515 | a–d | 4 | 1.19 | d–f | 4 | 2.38 | a–d |
| 60+2 | 4 | 0.0 | a | 4 | 0.0 | a | 4 | 304.9 | a–c | 4 | 1.425 | c–d | 4 | 2.19 | c–e | 4 | 2.94 | a–c |
| 60+4 | 4 | 0.0 | a | 4 | 0.0 | a | 4 | 289.7 | a–d | 4 | 1.470 | b–d | 4 | 2.13 | c–e | 4 | 2.69 | a–c |
| 60+6 | 4 | 0.0 | a | 4 | 0.0 | a | 4 | 275.0 | a–d | 4 | 1.565 | a–d | 4 | 0.56 | e–f | 4 | 1.88 | b–d |
| 80+2 | 4 | 0.0 | a | 4 | 0.0 | a | 4 | 293.5 | a–d | 4 | 1.470 | b–d | 4 | 1.88 | c–e | 4 | 3.50 | a |
| 80+4 | 4 | 0.0 | a | 4 | 0.0 | a | 4 | 301.5 | a–c | 4 | 1.487 | a–d | 4 | 1.06 | d–f | 4 | 2.75 | a–c |
| 80+6 | 4 | 0.0 | a | 4 | 0.0 | a | 4 | 286.9 | a–d | 4 | 1.460 | b–d | 4 | 0.63 | e–f | 4 | 1.50 | d |

EXPERIMENT NO. 37
Statistical Analyses of Percent Mortality, Weight Gain, Feed/Gain,
Intestinal and Cecal Lesion Scores of broiler cockerels inoculated with
*E. tenella* and *E. maxima*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 4 | 0.0 | b | 4 | 0.0 | b | 4 | 322.4 | a | 4 | 1.473 | g | 4 | 0.00 | e | 4 | 0.00 | b |

-continued

| | # | Total % | | # | % DTC | | # | Mean | | # | Mean | | # | Mean | | # | Mean | |
|---|---|---|---|---|---|---|---|---|---|---|---|---|---|---|---|---|---|---|
| IC | | | | | | | | | | | | | | | | | | |
| 0 | 4 | 43.8 | a | 4 | 43.8 | a | 4 | 145.9 | g–h | 4 | 2.438 | b–c | 4 | 8.06 | a | 4 | 3.94 | a |
| Monensin | | | | | | | | | | | | | | | | | | |
| 20 | 4 | 37.5 | a–b | 4 | 27.5 | a–b | 4 | 165.9 | f–h | 4 | 2.364 | b–d | 4 | 8.13 | a | 4 | 3.81 | a |
| 40 | 4 | 25.0 | a–b | 4 | 25.0 | a–b | 4 | 177.1 | e–h | 4 | 2.306 | b–e | 4 | 8.19 | a | 4 | 3.75 | a |
| 60 | 4 | 6.3 | a–b | 4 | 6.3 | a–b | 4 | 180.6 | e–h | 4 | 2.252 | b–f | 4 | 7.63 | a | 4 | 3.63 | a |
| 80 | 4 | 18.8 | a–b | 4 | 18.8 | a–b | 4 | 162.1 | f–h | 4 | 2.126 | b–f | 4 | 7.56 | a | 4 | 3.81 | a |
| Example No. 57 | | | | | | | | | | | | | | | | | | |
| 2 | 4 | 43.8 | a | 4 | 43.8 | a | 4 | 141.8 | g–h | 4 | 2.623 | a–b | 4 | 7.69 | a | 4 | 3.81 | a |
| 4 | 4 | 27.5 | a–b | 4 | 37.5 | a–b | 4 | 172.8 | f–h | 4 | 2.310 | b–e | 4 | 6.44 | a–d | 4 | 3.88 | a |
| 6 | 4 | 12.5 | a–b | 4 | 112.5 | a–b | 4 | 179.1 | e–h | 4 | 2.169 | b–f | 4 | 7.31 | a–b | 4 | 3.69 | a |
| Monensin + Example No. 57 | | | | | | | | | | | | | | | | | | |
| 20+2 | 4 | 12.5 | a–b | 4 | 12.5 | a–b | 4 | 133.7 | h | 4 | 2.892 | a | 4 | 7.94 | a | 4 | 3.94 | a |
| 20+4 | 4 | 18.8 | a–b | 4 | 18.8 | a–b | 4 | 194.0 | d–h | 4 | 2.128 | b–f | 4 | 6.94 | a–c | 4 | 3.94 | a |
| 20+6 | 4 | 12.5 | a–b | 4 | 12.5 | a–b | 4 | 221.9 | b–f | 4 | 1.814 | c–g | 4 | 6.81 | a–c | 4 | 3.63 | a |
| 40+2 | 4 | 6.3 | a–b | 4 | 6.3 | a–b | 4 | 180.0 | e–h | 4 | 2.182 | b–f | 4 | 7.94 | a | 4 | 3.75 | a |
| 40+4 | 4 | 6.3 | a–b | 4 | 6.3 | a–b | 4 | 205.5 | c–g | 4 | 2.099 | b–f | 4 | 7.69 | a | 4 | 4.00 | a |
| 40+6 | 4 | 6.3 | a–b | 4 | 6.3 | a–b | 4 | 247.9 | b–d | 4 | 1.716 | d–g | 4 | 6.25 | a–d | 4 | 3.81 | a |
| 60+2 | 4 | 12.5 | a–b | 4 | 12.5 | a–b | 4 | 228.2 | b–f | 4 | 1.815 | c–g | 4 | 7.19 | a–b | 4 | 3.94 | a |
| 60+4 | 4 | 12.5 | a–b | 4 | 6.3 | a–b | 4 | 243.8 | b–e | 4 | 1.770 | d–g | 4 | 6.90 | a–c | 4 | 3.75 | a |
| 60+6 | 4 | 6.3 | a–b | 4 | 6.3 | a–b | 4 | 266.7 | b–c | 3 | 1.651 | e–g | 4 | 5.06 | c–d | 4 | 3.94 | a |
| 80+2 | 4 | 31.3 | a–b | 4 | 31.3 | a–b | 4 | 209.9 | b–g | 4 | 1.994 | b–g | 4 | 6.94 | a–c | 4 | 3.81 | a |
| 80+4 | 4 | 0.0 | b | 4 | 0.0 | b | 4 | 261.1 | b–c | 4 | 1.612 | f–g | 4 | 5.50 | b–d | 4 | 3.81 | a |
| 80+6 | 4 | 0.0 | b | 4 | 0.0 | b | 4 | 274.5 | b | 4 | 1.653 | e–g | 4 | 4.94 | d | 4 | 3.69 | a |

EXPERIMENT NO. 38
Statistical Analyses of Percent Mortality, Weight Gain, Feed/Gain,
Intestinal and Cecal Lesion Scores of broiler cockerels inoculated with
*E. acervulina*, *E. tenella* and *E. maxima*

| Treatment | Mortality Mean | | | | | | Wt. Gain | | Feed/Gain | | Lesion Scores | | | |
|---|---|---|---|---|---|---|---|---|---|---|---|---|---|---|
| | | | | | | | | | | | Intestinal | | Cecal | |
| PPM | # | Total % | | # | % DTC | | # | Mean | # | Mean | # | Mean | # | Mean |
| NC | | | | | | | | | | | | | | |
| 0 | 4 | 0.0 | a | 4 | 0.0 | a | 4 | 321.1 | a–b | 4 | 1.488 | b | 4 | 0.00 | b | 4 | 0.00 | c |
| IC | | | | | | | | | | | | | | |
| 0 | 4 | 6.3 | a | 4 | 0.0 | a | 4 | 214.4 | c | 4 | 1.960 | a | 4 | 8.00 | a | 4 | 3.73 | a |
| A80190 | | | | | | | | | | | | | | |
| 30 | 4 | 0.0 | a | 4 | 0.0 | a | 4 | 334.0 | a | 4 | 1.437 | b | 4 | 0.25 | b | 4 | 0.25 | c |
| 40 | 4 | 0.0 | a | 4 | 0.0 | a | 4 | 330.8 | a | 4 | 1.430 | b | 4 | 0.25 | b | 4 | 0.00 | c |
| 50 | 4 | 0.0 | a | 4 | 0.0 | a | 4 | 306.1 | a–b | 4 | 1.480 | b | 4 | 0.00 | b | 4 | 0.00 | c |
| Example No. 57 | | | | | | | | | | | | | | |
| 2 | 4 | 6.3 | a | 4 | 6.3 | a | 4 | 223.5 | c | 4 | 1.852 | a | 4 | 8.06 | a | 4 | 3.50 | a–b |
| 3 | 4 | 6.3 | a | 4 | 0.0 | a | 4 | 218.0 | c | 4 | 1.897 | a | 4 | 8.44 | a | 4 | 3.08 | b |
| 4 | 4 | 0.0 | a | 4 | 0.0 | a | 4 | 228.1 | c | 4 | 1.892 | a | 4 | 8.06 | a | 4 | 3.69 | a |
| A80190 + Example No. 57 | | | | | | | | | | | | | | |
| 30+2 | 4 | 0.0 | a | 4 | 0.0 | a | 4 | 324.7 | a–b | 4 | 1.407 | b | 4 | 0.00 | b | 4 | 0.25 | c |
| 30+3 | 4 | 0.0 | a | 4 | 0.0 | a | 4 | 315.3 | a–b | 4 | 1.459 | b | 4 | 0.00 | b | 4 | 0.13 | c |
| 30+4 | 4 | 0.0 | a | 4 | 0.0 | a | 4 | 317.1 | a–b | 4 | 1.424 | b | 4 | 0.00 | b | 4 | 0.00 | c |
| 40+2 | 4 | 0.0 | a | 4 | 0.0 | a | 4 | 329.2 | a | 4 | 1.414 | b | 4 | 0.00 | b | 4 | 0.00 | c |
| 40+3 | 4 | 0.0 | a | 4 | 0.0 | a | 4 | 292.5 | a–b | 4 | 1.503 | b | 4 | 0.00 | b | 4 | 0.00 | c |
| 40+4 | 4 | 0.0 | a | 4 | 0.0 | a | 4 | 285.1 | b | 4 | 1.562 | b | 4 | 0.00 | b | 3 | 0.00 | c |
| 50+2 | 4 | 0.0 | a | 4 | 0.0 | a | 4 | 304.3 | a–b | 4 | 1.497 | b | 4 | 0.00 | b | 4 | 0.00 | c |
| 50+3 | 4 | 0.0 | a | 4 | 0.0 | a | 4 | 304.4 | a–b | 4 | 1.487 | b | 4 | 0.00 | b | 4 | 0.00 | c |
| 50+4 | 4 | 0.0 | a | 4 | 0.0 | a | 4 | 303.6 | a–b | 4 | 1.522 | b | 4 | 0.00 | b | 4 | 0.00 | c |

EXPERIMENT NO. 39
Statistical Analyses of Percent Mortality, Weight Gain, Feed/Gain,
Intestinal and Cecal Lesion Scores of broiler cockerels inoculated with
*E. acervulina, E. maxima* and *E. tenella*

| Treatment | | Mortality Mean | | | | | Wt. Gain | | | Feed/Gain | | | Lesion Scores | | | | |
|---|---|---|---|---|---|---|---|---|---|---|---|---|---|---|---|---|---|
| | | | | | | | | | | | | | Intestinal | | | Cecal | |
| PPM | # | Total % | | # | % DTC | | # | Mean | | # | Mean | | # | Mean | | # | Mean |
| NC | | | | | | | | | | | | | | | | | |
| 0 | 4 | 0.0 | a | 4 | 0.0 | b | 4 | 316.7 | a | 4 | 1.414 | b | 4 | 0.00 | d | 4 | 0.00 | f |
| IC | | | | | | | | | | | | | | | | | | |
| 0 | 4 | 25.0 | a | 4 | 25.0 | a | 4 | 169.3 | c | 4 | 2.188 | a | 4 | 8.75 | a | 4 | 3.81 | a |
| A80190 | | | | | | | | | | | | | | | | | | |
| 30 | 4 | 0.0 | a | 4 | 0.0 | b | 4 | 256.0 | b | 4 | 1.586 | b | 4 | 7.63 | a | 4 | 3.69 | a |
| 40 | 4 | 0.0 | a | 4 | 0.0 | b | 4 | 274.8 | a–b | 4 | 1.572 | b | 4 | 5.31 | b | 4 | 2.75 | a–d |
| 50 | 4 | 6.3 | a | 4 | 0.0 | b | 4 | 290.1 | a–b | 4 | 1.487 | b | 4 | 2.90 | b–d | 4 | 2.17 | b–e |
| Example No. 57 | | | | | | | | | | | | | | | | | | |
| 2 | 4 | 12.5 | a | 4 | 12.5 | a–b | 4 | 185.7 | c | 4 | 2.039 | a | 4 | 8.50 | a | 4 | 3.50 | a–b |
| 3 | 4 | 18.8 | a | 4 | 12.5 | a–b | 4 | 189.1 | c | 4 | 2.091 | a | 4 | 8.65 | a | 4 | 3.75 | a |
| 4 | 4 | 18.8 | a | 4 | 18.8 | a–b | 4 | 161.3 | c | 4 | 2.222 | a | 4 | 8.25 | a | 4 | 3.81 | a |
| A80190 + Example No. 57 | | | | | | | | | | | | | | | | | | |
| 30+2 | 4 | 0.0 | a | 4 | 0.0 | b | 4 | 269.6 | a–b | 4 | 1.597 | b | 4 | 5.25 | b | 4 | 3.06 | a–c |
| 30+3 | 4 | 0.0 | a | 4 | 0.0 | b | 4 | 295.6 | a–b | 4 | 1.477 | b | 4 | 3.38 | b–c | 4 | 2.81 | a–d |
| 30+4 | 4 | 0.0 | a | 4 | 0.0 | b | 4 | 294.5 | a–b | 4 | 1.481 | b | 4 | 1.19 | c–d | 4 | 1.75 | c–e |
| 40+2 | 4 | 0.0 | a | 4 | 0.0 | b | 4 | 269.1 | a–b | 4 | 1.647 | b | 4 | 3.50 | b–c | 4 | 2.50 | a–d |
| 40+3 | 4 | 12.5 | a | 4 | 6.3 | a–b | 4 | 290.7 | a–b | 4 | 1.489 | b | 4 | 1.60 | c–d | 4 | 1.56 | d–e |
| 40+4 | 4 | 0.0 | a | 4 | 0.0 | b | 4 | 300.0 | a–b | 4 | 1.493 | b | 4 | 0.00 | d | 4 | 1.44 | d–e |
| 50+2 | 4 | 0.0 | a | 4 | 0.0 | b | 4 | 266.7 | a–b | 4 | 1.584 | b | 4 | 0.19 | d | 4 | 0.88 | e–f |
| 50+3 | 4 | 0.0 | a | 4 | 0.0 | b | 4 | 268.7 | a–b | 4 | 1.608 | b | 4 | 0.25 | d | 4 | 0.75 | e–f |
| 50+4 | 4 | 0.0 | a | 4 | 0.0 | b | 4 | 273.4 | a–b | 4 | 1.556 | b | 4 | 0.00 | d | 4 | 0.88 | e–f |

EXPERIMENT NO. 40
Statistical Analyses of Percent Mortality, Weight Gain, Feed/Gain,
Intestinal and Cecal Lesion Scores of broiler cockerels inoculated with
*E. acervulina* and *E. tenella*

| Treatment | | Mortality Mean | | | | | Wt. Gain | | | Feed/Gain | | | Lesion Scores | | | | |
|---|---|---|---|---|---|---|---|---|---|---|---|---|---|---|---|---|---|
| | | | | | | | | | | | | | Intestinal | | | Cecal | |
| PPM | # | Total % | | # | % DTC | | # | Mean | | # | Mean | | # | Mean | | # | Mean |
| NC | | | | | | | | | | | | | | | | | | |
| 0 | 3 | 0.0 | a | 3 | 0.0 | a | 3 | 333.5 | a | 3 | 1.400 | d | 3 | 0.00 | c | 3 | 0.00 | g |
| IC | | | | | | | | | | | | | | | | | | |
| 0 | 3 | 0.0 | a | 3 | 0.0 | a | 3 | 235.5 | e–f | 3 | 1.747 | c | 3 | 8.58 | a | 3 | 3.33 | a |
| A204 | | | | | | | | | | | | | | | | | | |
| 2 | 3 | 0.0 | a | 3 | 0.0 | a | 3 | 247.8 | d–e | 3 | 1.670 | c | 3 | 4.33 | b | 3 | 3.33 | a |
| 4 | 3 | 0.0 | a | 3 | 0.0 | a | 3 | 278.9 | b–d | 3 | 1.680 | c | 3 | 3.83 | b | 3 | 3.33 | a |
| 8 | 3 | 0.0 | a | 3 | 0.0 | a | 3 | 312.7 | a–b | 3 | 1.487 | c–d | 3 | 0.17 | c | 3 | 3.00 | a |
| Example No. 39 | | | | | | | | | | | | | | | | | | |
| 2 | 3 | 0.0 | a | 3 | 0.0 | a | 3 | 269.0 | c–d | 3 | 1.653 | c–d | 3 | 0.33 | c | 3 | 3.50 | a |
| 4 | 3 | 8.3 | a | 3 | 0.0 | a | 3 | 271.7 | b–d | 2 | 1.612 | c–d | 3 | 0.08 | c | 3 | 1.89 | b–c |
| 8 | 3 | 0.0 | a | 3 | 0.0 | a | 3 | 207.7 | f–g | 3 | 1.936 | b | 3 | 0.00 | c | 3 | 0.92 | d–f |
| A204 + Example No. 39 | | | | | | | | | | | | | | | | | | |
| 2+2 | 3 | 0.0 | a | 3 | 0.0 | a | 3 | 300.6 | a–c | 3 | 1.554 | c–d | 3 | 0.00 | c | 3 | 3.17 | a |
| 2+4 | 3 | 0.0 | a | 3 | 0.0 | a | 3 | 280.2 | b–d | 3 | 1.592 | c–d | 3 | 0.00 | c | 3 | 1.50 | c–d |
| 2+8 | 3 | 0.0 | a | 3 | 0.0 | a | 3 | 205.4 | f–g | 3 | 2.008 | a–b | 3 | 0.00 | c | 3 | 0.67 | e–g |
| 4+2 | 3 | 0.0 | a | 3 | 0.0 | a | 3 | 286.3 | b–d | 3 | 1.553 | c–d | 3 | 0.00 | c | 3 | 2.16 | b |
| 4+4 | 3 | 0.0 | a | 3 | 0.0 | a | 3 | 279.3 | b–d | 3 | 1.573 | c–d | 3 | 0.00 | c | 3 | 1.17 | d–e |
| 4+8 | 3 | 0.0 | a | 3 | 0.0 | a | 3 | 195.0 | g | 3 | 1.984 | a–b | 3 | 0.00 | c | 3 | 0.17 | f–g |
| 8+2 | 3 | 0.0 | a | 3 | 0.0 | a | 3 | 308.8 | a–c | 3 | 1.491 | c–d | 3 | 0.00 | c | 3 | 0.67 | e–g |
| 8+4 | 3 | 0.0 | a | 3 | 0.0 | a | 3 | 292.3 | b–c | 3 | 1.596 | c–d | 3 | 0.00 | c | 3 | 0.33 | f–g |
| 8+8 | 3 | 8.3 | a | 3 | 0.0 | a | 3 | 199.3 | g | 2 | 2.187 | a | 3 | 0.00 | c | 3 | 0.00 | g |

EXPERIMENT NO. 41
Statistical Analyses of Percent Mortality, Weight Gain, Feed/Gain,
Intestinal and Cecal Lesion Scores of broiler cockerels inoculated with
E. acervulina and E. tenella

| Treatment | | Mortality Mean | | | | Wt. Gain | | Feed/Gain | | | Lesion Scores | | | | |
|---|---|---|---|---|---|---|---|---|---|---|---|---|---|---|---|
| | | | | | | | | | | | Intestinal | | | Cecal | |
| PPM | # | Total % | | # | % DTC | | # | Mean | # | Mean | # | Mean | # | Mean | |
| NC | | | | | | | | | | | | | | | |
| 0 | 3 | 0.0 | a | 3 | 0.0 | a | 3 | 308.8 a | 3 | 1.485 b | 3 | 0.00 c | 3 | 0.00 | b |
| IC | | | | | | | | | | | | | | | |
| 0 | 3 | 0.0 | a | 3 | 0.0 | a | 3 | 247.1 c-e | 3 | 1.722 a-b | 3 | 5.25 a | 3 | 3.42 | a |
| A82810 | | | | | | | | | | | | | | | |
| 1 | 3 | 0.0 | a | 3 | 0.0 | a | 3 | 238.1 c-e | 3 | 1.797 a-b | 3 | 2.75 b | 3 | 3.17 | a |
| 3 | 3 | 0.0 | a | 3 | 0.0 | a | 3 | 295.2 a-b | 3 | 1.544 a-b | 3 | 1.50 c | 3 | 2.67 | a |
| 5 | 3 | 8.3 | a | 3 | 0.0 | a | 3 | 301.8 a | 2 | 1.466 b | 3 | 0.17 c | 3 | 0.42 | b |
| Example No. 39 | | | | | | | | | | | | | | | |
| 2 | 3 | 0.0 | a | 3 | 0.0 | a | 3 | 235.3 c-e | 3 | 1.789 a-b | 3 | 1.25 c | 3 | 3.42 | a |
| 4 | 3 | 0.0 | a | 3 | 0.0 | a | 3 | 246.0 c-e | 3 | 1.766 a-b | 3 | 0.00 c | 3 | 2.58 | a |
| 8 | 3 | 16.7 | a | 3 | 0.0 | a | 3 | 219.3 d-e | 2 | 1.875 a | 3 | 0.00 c | 3 | 0.83 | b |
| A82810 + Example No. 39 | | | | | | | | | | | | | | | |
| 1+2 | 3 | 0.0 | a | 3 | 0.0 | a | 3 | 290.9 a-b | 3 | 1.499 b | 3 | 0.33 c | 3 | 2.75 | a |
| 1+4 | 3 | 0.0 | a | 3 | 0.0 | a | 3 | 253.3 b-e | 3 | 1.689 a-b | 3 | 0.00 c | 3 | 0.83 | b |
| 1+8 | 3 | 0.0 | a | 3 | 0.0 | a | 3 | 221.4 d-e | 3 | 1.902 a | 3 | 0.00 c | 3 | 0.00 | b |
| 3+2 | 3 | 0.0 | a | 3 | 0.0 | a | 3 | 265.9 a-d | 3 | 1.673 a-b | 3 | 0.08 c | 3 | 1.17 | b |
| 3+4 | 3 | 25.0 | a | 3 | 0.0 | a | 3 | 269.3 a-c | 1 | 1.829 a-b | 3 | 0.00 c | 3 | 0.00 | b |
| 3+8 | 3 | 16.7 | a | 3 | 0.0 | a | 3 | 209.0 e | 1 | 1.829 a-b | 3 | 0.00 c | 3 | 0.00 | b |
| 5+2 | 3 | 0.0 | a | 3 | 0.0 | a | 3 | 292.1 a-b | 3 | 1.551 a-b | 3 | 0.00 c | 3 | 0.33 | b |
| 5+4 | 3 | 8.3 | a | 3 | 0.0 | a | 3 | 277.1 a-c | 2 | 1.620 a-b | 3 | 0.00 c | 3 | 0.08 | b |
| 5+8 | 3 | 0.0 | a | 3 | 0.0 | a | 3 | 230.9 c-e | 3 | 1.790 a-b | 3 | 0.00 c | 3 | 0.00 | b |

EXPERIMENT NO. 42
Statistical Analyses of Percent Mortality, Weight Gain, Feed/Gain,
Intestinal and Cecal Lesion Scores of broiler cockerels inoculated with
E. acervulina and E. tenella

| Treatment | | Mortality Mean | | | | Wt. Gain | | Feed/Gain | | | Lesion Scores | | | | |
|---|---|---|---|---|---|---|---|---|---|---|---|---|---|---|---|
| | | | | | | | | | | | Intestinal | | | Cecal | |
| PPM | # | Total % | | # | % DTC | | # | Mean | # | Mean | # | Mean | # | Mean | |
| NC | | | | | | | | | | | | | | | |
| 0 | 3 | 0.0 | a | 3 | 0.0 | a | 3 | 261.9 a-b | 3 | 1.467 b | 3 | 0.00 b | 3 | 0.00 | c |
| IC | | | | | | | | | | | | | | | |
| 0 | 3 | 16.7 | a | 3 | 0.0 | a | 3 | 227.8 a-c | 1 | 1.735 a-b | 3 | 4.50 a | 3 | 2.67 | a |
| A82810 | | | | | | | | | | | | | | | |
| 1 | 3 | 0.0 | a | 3 | 0.0 | a | 3 | 233.8 a-c | 3 | 1.628 a-b | 3 | 5.67 a | 3 | 3.00 | a |
| 3 | 3 | 0.0 | a | 3 | 0.0 | a | 3 | 270.5 a | 3 | 1.507 b | 3 | 1.08 b | 3 | 1.83 | a-b |
| 5 | 3 | 16.7 | a | 3 | 0.0 | a | 3 | 255.7 a-b | 2 | 1.541 a-b | 3 | 0.42 b | 3 | 0.92 | b-c |
| Example No. 57 | | | | | | | | | | | | | | | |
| 3 | 3 | 0.0 | a | 3 | 0.0 | a | 3 | 200.8 b-c | 3 | 1.774 a-b | 3 | 4.75 a | 3 | 3.08 | a |
| 6 | 3 | 0.0 | a | 3 | 0.0 | a | 3 | 218.5 a-c | 3 | 1.730 a-b | 3 | 1.00 b | 3 | 2.50 | a |
| 12 | 3 | 0.0 | a | 3 | 0.0 | a | 3 | 203.0 a-c | 3 | 1.783 a-b | 3 | 0.00 b | 3 | 1.17 | b-c |
| A82810 + Example No. 57 | | | | | | | | | | | | | | | |
| 1+3 | 3 | 8.3 | a | 3 | 8.3 | a | 3 | 256.1 a-b | 2 | 1.559 a-b | 3 | 2.33 b | 3 | 2.67 | a |
| 1+6 | 3 | 0.0 | a | 3 | 0.0 | a | 3 | 255.8 a-b | 3 | 1.561 a-b | 3 | 0.25 b | 3 | 1.17 | b-c |
| 1+12 | 3 | 33.3 | a | 3 | 0.0 | a | 3 | 178.8 c | 1 | 2.051 a | 3 | 0.00 b | 3 | 0.17 | c |
| 3+3 | 3 | 0.0 | a | 3 | 0.0 | a | 3 | 261.0 a-b | 3 | 1.524 a-b | 3 | 0.25 b | 3 | 1.00 | b-c |
| 3+6 | 3 | 0.0 | a | 3 | 0.0 | a | 3 | 231.2 a-c | 3 | 1.646 a-b | 3 | 0.00 b | 3 | 0.42 | b-c |
| 3+12 | 3 | 0.0 | a | 3 | 0.0 | a | 3 | 217.3 a-c | 3 | 1.716 a-b | 3 | 0.00 b | 3 | 0.08 | c |
| 5+3 | 3 | 0.0 | a | 3 | 0.0 | a | 3 | 245.9 a-b | 3 | 1.567 a-b | 3 | 0.00 b | 3 | 0.58 | b-c |
| 5+6 | 3 | 16.7 | a | 3 | 0.0 | a | 3 | 247.6 a-b | 1 | 1.513 a-b | 3 | 0.00 b | 3 | 0.11 | c |
| 5+12 | 3 | 0.0 | a | 3 | 0.0 | a | 3 | 194.6 b-c | 3 | 1.889 a | 3 | 0.00 b | 3 | 0.08 | c |

EXPERIMENT NO. 43
Statistical Analyses of Percent Mortality, Weight Gain, Feed/Gain,
Intestinal and Cecal Lesion Scores of broiler cockerels inoculated with
*E. maxima* and *E. tenella*

| Treatment | | Mortality Mean | | | | Wt. Gain | | Feed/Gain | | Lesion Scores | | | | | |
|---|---|---|---|---|---|---|---|---|---|---|---|---|---|---|---|
| | | | | | | | | | | Intestinal | | | Cecal | | |
| PPM | # | Total % | | # | % DTC | | # | Mean | # | Mean | # | Mean | | # | Mean | |
| NC | | | | | | | | | | | | | | | | |
| 0 | 2 | 0.0 | a | 2 | 0.0 | b | 2 | 313.8 a | 2 | 1.548 c | 2 | 0.00 | c | 2 | 0.00 | d |
| IC | | | | | | | | | | | | | | | | |
| 0 | 3 | 8.3 | a | 3 | 8.3 | b | 3 | 168.3 d | 2 | 2.404 a | 3 | 8.58 | a | 3 | 3.58 | a |
| A82810 | | | | | | | | | | | | | | | | |
| 1 | 3 | 8.3 | a | 3 | 8.3 | b | 3 | 188.8 c–d | 2 | 2.037 b | 3 | 8.42 | a | 3 | 3.42 | a |
| 3 | 3 | 8.3 | a | 3 | 0.0 | b | 3 | 286.9 a | 2 | 1.588 c | 3 | 5.78 | b | 3 | 2.25 | b–c |
| 5 | 3 | 8.3 | a | 3 | 0.0 | b | 3 | 300.6 a | 2 | 1.505 c | 3 | 2.75 | c | 3 | 1.14 | d |
| Example No. 57 | | | | | | | | | | | | | | | | |
| 3 | 3 | 33.3 | a | 3 | 33.3 | a | 3 | 191.8 c–d | 1 | 1.873 b–c | 3 | 7.50 | a–b | 3 | 3.42 | a |
| 6 | 3 | 0.0 | a | 3 | 0.0 | b | 3 | 227.9 b–c | 3 | 1.828 b–c | 3 | 5.42 | b | 3 | 3.42 | a |
| 12 | 3 | 8.3 | a | 3 | 0.0 | b | 3 | 253.8 a–b | 2 | 1.740 b–c | 3 | 0.50 | c | 3 | 1.42 | c–d |
| A82810 + Example No. 57 | | | | | | | | | | | | | | | | |
| 1+3 | 3 | 16.7 | a | 3 | 8.3 | b | 3 | 266.2 a–b | 1 | 1.701 b–c | 3 | 3.11 | c | 3 | 3.64 | a |
| 1+6 | 3 | 0.0 | a | 3 | 0.0 | b | 3 | 255.5 a–b | 3 | 1.673 c | 3 | 2.50 | c | 3 | 2.50 | a–b |
| 1+12 | 3 | 8.3 | a | 3 | 0.0 | b | 3 | 249.4 a–b | 2 | 1.776 b–c | 3 | 0.00 | c | 3 | 1.06 | d |
| 3+3 | 3 | 0.0 | a | 3 | 0.0 | b | 3 | 286.6 a | 3 | 1.537 c | 3 | 0.92 | c | 3 | 1.50 | c–d |
| 3+6 | 3 | 0.0 | a | 3 | 0.0 | b | 3 | 284.5 a | 3 | 1.556 c | 3 | 0.17 | c | 3 | 0.92 | d |
| 3+12 | 3 | 8.3 | a | 3 | 0.0 | b | 3 | 263.4 a–b | 2 | 1.746 b–c | 3 | 0.08 | c | 3 | 0.17 | d |
| 5+3 | 3 | 0.0 | a | 3 | 0.0 | b | 3 | 310.1 a | 3 | 1.517 c | 3 | 0.00 | c | 3 | 0.67 | d |
| 5+6 | 3 | 0.0 | a | 3 | 0.0 | b | 3 | 289.3 a | 3 | 1.571 c | 3 | 0.00 | c | 3 | 0.25 | d |
| 5+12 | 3 | 8.3 | a | 3 | 0.0 | b | 3 | 292.5 a | 2 | 1.577 c | 3 | 0.00 | c | 3 | 0.00 | d |

EXPERIMENT NO. 44
Statistical Analyses of Percent Mortality, Weight Gain, Feed/Gain,
Intestinal and Cecal Lesion Scores of broiler cockerels inoculated with
*E. acervulina*, *E. maxima* and *E. tenella*

| Treatment | | Mortality Mean | | | | | Wt. Gain | | Feed/Gain | | Lesion Scores | | | | | |
|---|---|---|---|---|---|---|---|---|---|---|---|---|---|---|---|---|
| | | | | | | | | | | | Intestinal | | | Cecal | | |
| PPM | # | Total % | | # | % DTC | | # | Mean | | # | Mean | | # | Mean | # | Mean |
| NC | | | | | | | | | | | | | | | | | |
| 0 | 4 | 0.0 | c | 4 | 0.0 | b | 4 | 220.8 | a | 4 | 1.466 | c | 3 | 0.00 d | 4 | 0.00 d |
| IC | | | | | | | | | | | | | | | | | |
| 0 | 4 | 55.0 | b | 4 | 55.0 | a | 3 | 74.2 | c | | | | 3 | 3.64 b | 3 | 3.81 a |
| Example No. 5 | | | | | | | | | | | | | | | | | |
| 30 | 4 | 100.0 | a | 4 | 0.0 | b | | | | | | | | | | |
| 20 | 4 | 95.0 | a | 4 | 5.0 | b | 1 | 89.0 | c | | | | 1 | 0.00 d | 1 | 0.00 d |
| 10 | 4 | 5.0 | c | 4 | 0.0 | b | 4 | 144.6 | b | 3 | 2.138 | a | 4 | 0.00 d | 4 | 1.59 c |

EXPERIMENT NO. 45
Statistical Analyses of Percent Mortality, Weight Gain, Feed/Gain,
Intestinal and Cecal Lesion Scores of broiler cockerels inoculated with
*E. tenella*, *E. acervulina* and *E. maxima*

| Treatment | | Mortality Mean | | | | | Wt. Gain | | Feed/Gain | | Lesion Scores | | | | |
|---|---|---|---|---|---|---|---|---|---|---|---|---|---|---|---|
| | | | | | | | | | | | Intestinal | | Cecal | | |
| PPM | # | Total % | | # | % DTC | | # | Mean | | # | Mean | | # | Mean | # | Mean |
| NC | | | | | | | | | | | | | | | | |
| 0 | 3 | 0.0 | c | 3 | 0.0 | a | 3 | 236.7 | a | 3 | 1.551 b | 3 | 0.00 c | 3 | 0.00 b |
| IC | | | | | | | | | | | | | | | | |
| 0 | 3 | 13.3 | c | 3 | 13.3 | a | 3 | 160.7 | b | 1 | 1.950 a | 3 | 3.62 a | 3 | 2.93 a |

-continued

| Example No. 5 | | | | | | | | | | | | | | | | | | |
|---|---|---|---|---|---|---|---|---|---|---|---|---|---|---|---|---|---|---|
| 10 | 3 | 13.3 | c | 3 | 13.3 | a | 3 | 153.7 | b | 1 | 2.176 | a | 3 | 0.25 | c | 3 | 2.30 | a |
| 7.5 | 3 | 13.3 | c | 3 | 13.3 | a | 3 | 164.9 | b | 2 | 2.050 | a | 3 | 0.47 | c | 3 | 1.82 | a |
| 5 | 3 | 26.7 | b–c | 3 | 26.7 | a | 3 | 163.5 | b | 1 | 2.177 | a | 3 | 1.51 | b | 3 | 2.78 | a |
| 2.5 | 3 | 20.0 | c | 3 | 20.0 | a | 3 | 156.3 | b | | | | 3 | 1.92 | b | 3 | 2.33 | a |
| Example No. 90 | | | | | | | | | | | | | | | | | | |
| 75 | 3 | 100.0 | a | 3 | 0.0 | a | | | | | | | | | | | | |
| 50 | 3 | 46.7 | b | 3 | 0.0 | a | 3 | 70.4 | c | | | | 3 | 0.00 | c | 3 | 0.00 | b |
| 25 | 3 | 0.0 | c | 3 | 0.0 | a | 3 | 172.3 | b | 3 | 1.968 | a | 3 | 0.00 | c | 3 | 0.67 | b |

EXPERIMENT NO. 46
Statistical Analyses of Percent Mortality, Weight Gain, Feed/Gain,
Intestinal and Cecal Lesion Scores of broiler cockerels inoculated with
*E. tenella*, *E. acervulina* and *E. maxima*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 3 | 6.7 a | 3 | 0.0 a | 3 | 296.0 a | 2 | 1.289 c | 3 | 0.00 b | 3 | 0.00 d |
| IC | | | | | | | | | | | | |
| 0 | 3 | 26.7 a | 3 | 26.7 a | 3 | 166.7 b | | | 3 | 8.11 a | 3 | 3.83 a |
| Example No. 94 | | | | | | | | | | | | |
| 5 | 2 | 0.0 a | 2 | 0.0 a | 2 | 218.8 b | 2 | 1.462 b–c | 2 | 1.60 b | 2 | 3.20 a |
| 3.5 | 2 | 10.0 a | 2 | 10.0 a | 2 | 208.4 b | 1 | 1.440 c | 2 | 1.52 b | 2 | 3.65 a |
| 2 | 2 | 40.0 a | 2 | 40.0 a | 2 | 165.1 b | | | 2 | 7.00 a | 2 | 3.67 a |
| Example No. 98 | | | | | | | | | | | | |
| 5 | 2 | 0.0 a | 2 | 0.0 a | 2 | 220.3 b | 2 | 1.478 b–c | 2 | 0.30 b | 2 | 2.50 b |
| 3.5 | 2 | 30.0 a | 2 | 30.0 a | 2 | 232.4 b | 1 | 1.614 b–c | 2 | 1.30 b | 2 | 3.80 a |
| 2 | 2 | 20.0 a | 2 | 20.0 a | 2 | 201.0 b | 1 | 1.491 b–c | 2 | 5.67 a | 2 | 3.47 a |
| Example No. 5 | | | | | | | | | | | | |
| 7.5 | 2 | 0.0 a | 2 | 0.0 a | 2 | 210.4 b | 2 | 1.557 b–c | 2 | 0.40 b | 2 | 2.00 b |
| 5 | 2 | 0.0 a | 2 | 0.0 a | 2 | 233.2 b | 2 | 1.440 c | 2 | 0.30 b | 2 | 2.60 b |
| 2.5 | 2 | 10.0 a | 2 | 10.0 a | 2 | 184.8 b | 1 | 1.779 a–b | 2 | 1.70 b | 2 | 3.65 a |

EXPERIMENT NO. 47
Statistical Analyses of Percent Mortality, Weight Gain, Feed/Gain,
Intestinal and Cecal Lesion Scores of broiler cockerels inoculated with
*E. acervulina* and *E. tenella*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 3 | 25.0 a | 3 | 0.0 a | 3 | 318.5 a | 1 | 1.425 c | 3 | 0.00 d | 3 | 0.00 c |
| IC | | | | | | | | | | | | |
| 0 | 3 | 41.7 a | 3 | 33.3 a | 3 | 229.6 c | | | 3 | 8.17 a–b | 3 | 3.22 a–b |
| A80190 | | | | | | | | | | | | |
| 8 | 3 | 16.7 a | 3 | 0.0 a | 3 | 240.8 b–c | 2 | 1.591 b–c | 3 | 7.50 b | 3 | 2.83 a–b |
| Example No. 5 | | | | | | | | | | | | |
| 2.5 | 3 | 8.3 a | 3 | 8.3 a | 3 | 213.0 c | 2 | 1.852 a | 3 | 9.00 a | 3 | 3.17 a–b |
| 5 | 3 | 0.0 a | 3 | 0.0 a | 3 | 242.5 b–c | 3 | 1.653 b | 3 | 0.25 d | 3 | 3.50 a |
| A80190 + Example No. 5 | | | | | | | | | | | | |
| 8+2.5 | 3 | 0.0 a | 3 | 0.0 a | 3 | 274.3 a–c | 3 | 1.488 c | 3 | 1.58 c | 3 | 2.92 a–b |
| 8+5 | 3 | 0.0 a | 3 | 0.0 a | 3 | 297.8 a–b | 3 | 1.440 c | 3 | 0.00 d | 3 | 1.92 b |

EXPERIMENT NO. 48
Statistical Analyses of Percent Mortality, Weight Gain, Feed/Gain,
Intestinal and Cecal Lesion Scores of broiler cockerels inoculated with
*E. acervulina* and *E. tenella*

| Treatment | | Mortality Mean | | | | Wt. Gain | | Feed/Gain | | Lesion Scores | | | |
|---|---|---|---|---|---|---|---|---|---|---|---|---|---|
| | | | | | | | | | | Intestinal | | Cecal | |
| PPM | # | Total % | | # | % DTC | | # | Mean | # | Mean | # | Mean | # | Mean |

| PPM | # | Total % | | # | % DTC | | # | Mean | | # | Mean | | # | Mean | | # | Mean | |
|---|---|---|---|---|---|---|---|---|---|---|---|---|---|---|---|---|---|---|
| NC | | | | | | | | | | | | | | | | | | |
| 0 | 3 | 0.0 | a | 3 | 0.0 | a | 3 | 321.8 | a | 3 | 1.391 | c | 3 | 0.00 | b | 3 | 0.00 | c |
| IC | | | | | | | | | | | | | | | | | | |
| 0 | 3 | 0.0 | a | 3 | 0.0 | a | 3 | 199.5 | f | 3 | 1.852 | a | 3 | 6.08 | a | 3 | 2.92 | a–b |
| A204 | | | | | | | | | | | | | | | | | | |
| 2 | 3 | 0.0 | a | 3 | 0.0 | a | 3 | 252.2 | c–e | 3 | 1.649 | a–c | 3 | 4.00 | a | 3 | 3.42 | a |
| 4 | 3 | 0.0 | a | 3 | 0.0 | a | 3 | 247.8 | d–e | 3 | 1.686 | a–b | 3 | 6.50 | a | 3 | 3.08 | a–b |
| 8 | 3 | 0.0 | a | 3 | 0.0 | a | 3 | 271.0 | c–e | 3 | 1.489 | b–c | 3 | 0.92 | b | 3 | 3.58 | a |
| Example No. 5 | | | | | | | | | | | | | | | | | | |
| 2 | 3 | 0.0 | a | 3 | 0.0 | a | 3 | 245.8 | d–e | 3 | 1.652 | a–c | 3 | 4.17 | a | 3 | 3.08 | a–b |
| 4 | 3 | 0.0 | a | 3 | 0.0 | a | 3 | 243.8 | d–e | 3 | 1.676 | a–c | 3 | 0.25 | b | 3 | 3.17 | a–b |
| 8 | 3 | 0.0 | a | 3 | 0.0 | a | 3 | 234.3 | d–e | 3 | 1.671 | a–c | 3 | 0.08 | b | 3 | 2.33 | a–b |
| A204 + Example No. 5 | | | | | | | | | | | | | | | | | | |
| 2+2 | 3 | 8.3 | a | 3 | 8.3 | a | 3 | 265.2 | c–e | 2 | 1.576 | a–c | 3 | 0.83 | b | 3 | 3.25 | a |
| 2+4 | 3 | 0.0 | a | 3 | 0.0 | a | 3 | 276.0 | c–e | 3 | 1.491 | b–c | 3 | 0.08 | b | 3 | 3.50 | a |
| 2+8 | 3 | 0.0 | a | 3 | 0.0 | a | 3 | 246.8 | d–e | 3 | 1.637 | a–c | 3 | 0.00 | b | 3 | 0.67 | c |
| 4+2 | 3 | 8.3 | a | 3 | 0.0 | a | 3 | 262.4 | c–e | 2 | 1.574 | a–c | 3 | 0.00 | b | 3 | 2.81 | a–b |
| 4+4 | 3 | 0.0 | a | 3 | 0.0 | a | 3 | 280.7 | b–d | 3 | 1.540 | b–c | 3 | 0.00 | b | 3 | 1.83 | b |
| 4+8 | 3 | 8.3 | a | 3 | 0.0 | a | 3 | 229.7 | e | 2 | 1.683 | a–c | 3 | 0.00 | b | 3 | 0.53 | c |
| 8+2 | 3 | 16.7 | a | 3 | 0.0 | a | 3 | 312.7 | a–b | 2 | 1.442 | b–c | 3 | 0.00 | b | 3 | 2.58 | a–b |
| 8+4 | 3 | 0.0 | a | 3 | 0.0 | a | 3 | 293.3 | a–c | 3 | 1.496 | b–c | 3 | 0.00 | b | 3 | 0.92 | c |
| 8+8 | 3 | 0.0 | a | 3 | 0.0 | a | 3 | 24.63 | d–e | 3 | 1.659 | a–c | 3 | 0.00 | b | 3 | 0.25 | c |

EXPERIMENT NO. 49
Statistical Analyses of Percent Mortality, Weight Gain, Feed/Gain,
Intestinal and Cecal Lesion Scores of broiler cockerels inoculated with
*E. acervulina* and *E. tenella*

| PPM | # | Total % | | # | % DTC | | # | Mean | | # | Mean | | # | Mean | | # | Mean | |
|---|---|---|---|---|---|---|---|---|---|---|---|---|---|---|---|---|---|---|
| NC | | | | | | | | | | | | | | | | | | |
| 0 | 3 | 8.3 | b–c | 3 | 0.0 | a | 3 | 325.5 | a | 2 | 1.359 | c | 3 | 0.00 | c | 3 | 0.00 | c |
| IC | | | | | | | | | | | | | | | | | | |
| 0 | 3 | 0.0 | c | 3 | 0.0 | a | 3 | 257.4 | c | 3 | 1.687 | b | 3 | 6.58 | a | 3 | 3.33 | a |
| A82810 | | | | | | | | | | | | | | | | | | |
| 1 | 3 | 0.0 | c | 3 | 0.0 | a | 3 | 262.1 | c | 3 | 1.638 | b–c | 3 | 6.17 | a | 3 | 3.42 | a |
| 3 | 3 | 0.0 | c | 3 | 0.0 | a | 3 | 288.0 | a–c | 3 | 1.506 | b–c | 3 | 2.75 | b | 3 | 2.92 | a |
| 5 | 3 | 0.0 | c | 3 | 0.0 | a | 3 | 319.8 | a–b | 3 | 1.424 | b–c | 3 | 0.92 | b–c | 3 | 1.75 | b |
| Example No. 113 | | | | | | | | | | | | | | | | | | |
| 6 | 3 | 8.3 | b–c | 3 | 0.0 | a | 3 | 255.2 | c | 2 | 1.662 | b–c | 3 | 0.17 | b–c | 3 | 2.06 | b |
| 12 | 3 | 41.7 | b | 3 | 0.0 | a | 3 | 179.4 | d | | | | 3 | 0.00 | c | 3 | 0.67 | c |
| 24 | 1 | 75.0 | a | 1 | 0.0 | a | 1 | 53.8 | f | | | | 1 | 0.00 | c | 1 | 0.00 | c |
| A82810 + Example No. 113 | | | | | | | | | | | | | | | | | | |
| 1+6 | 3 | 0.0 | c | 3 | 0.0 | a | 3 | 264.0 | c | 3 | 1.641 | b–c | 3 | 0.00 | c | 3 | 1.00 | c |
| 1+12 | 3 | 25.0 | b–c | 3 | 0.0 | a | 3 | 160.4 | d | 1 | 2.182 | a | 3 | 0.00 | c | 3 | 0.11 | c |
| 3+6 | 3 | 0.0 | c | 3 | 0.0 | a | 3 | 274.2 | b–c | 3 | 1.580 | b–c | 3 | 0.00 | c | 3 | 0.17 | c |
| 3+12 | 3 | 8.3 | b–c | 3 | 0.0 | a | 3 | 184.2 | d | 2 | 2.160 | a | 3 | 0.00 | c | 3 | 0.00 | c |
| 5+6 | 3 | 0.0 | c | 3 | 0.0 | a | 3 | 265.5 | c | 3 | 1.640 | b–c | 3 | 0.00 | c | 3 | 0.08 | c |
| 5+12 | 3 | 33.3 | b–c | 3 | 0.0 | a | 3 | 113.1 | e | | | | 3 | 0.00 | c | 3 | 0.00 | c |

EXPERIMENT NO. 50
Statistical Analyses of Percent Mortality, Weight Gain, Feed/Gain,
Intestinal and Cecal Lesion Scores of broiler cockerels inoculated with
*E. acervulina* and *E. tenella*

| Treatment | | Mortality Mean | | | | | Wt. Gain | | | Feed/Gain | | | Lesion Scores | | | | |
|---|---|---|---|---|---|---|---|---|---|---|---|---|---|---|---|---|---|
| | | | | | | | | | | | | | Intestinal | | | Cecal | |
| PPM | # | Total % | | # | % DTC | | # | Mean | | # | Mean | | # | Mean | | # | Mean |
| NC | | | | | | | | | | | | | | | | | |
| 0 | 3 | 0.0 | a | 3 | 0.0 | a | 3 | 307.9 | a–b | 3 | 1.516 | b–c | 3 | 0.00 | b | 3 | 0.00 | d |
| IC | | | | | | | | | | | | | | | | | | |
| 0 | 3 | 0.0 | a | 3 | 0.0 | a | 3 | 258.3 | b–e | 3 | 1.670 | a–c | 3 | 5.00 | a | 3 | 2.92 | a–b |
| A82810 | | | | | | | | | | | | | | | | | | |
| 1 | 3 | 0.0 | a | 3 | 0.0 | a | 3 | 250.0 | c–e | 3 | 1.692 | a–c | 3 | 3.75 | a | 3 | 2.67 | a–b |
| 3 | 3 | 0.0 | a | 3 | 0.0 | a | 3 | 285.3 | a–d | 3 | 1.599 | a–c | 3 | 1.33 | b | 3 | 2.50 | a–b |
| 5 | 3 | 0.0 | a | 3 | 0.0 | a | 3 | 313.5 | a | 3 | 1.446 | c | 3 | 0.25 | b | 3 | 0.92 | c–d |
| Example No. 113 | | | | | | | | | | | | | | | | | | |
| 2 | 3 | 0.0 | a | 3 | 0.0 | a | 3 | 254.3 | b–e | 3 | 1.714 | a–c | 3 | 3.92 | a | 3 | 3.33 | a |
| 4 | 3 | 8.3 | a | 3 | 0.0 | a | 3 | 285.4 | a–d | 2 | 1.541 | a–c | 3 | 0.39 | b | 3 | 3.19 | a–b |
| 8 | 3 | 0.0 | a | 3 | 0.0 | a | 3 | 239.7 | c–e | 3 | 1.724 | a–b | 3 | 0.00 | b | 3 | 0.42 | c–d |
| A82810 + Example No. 113 | | | | | | | | | | | | | | | | | | |
| 1+2 | 3 | 0.0 | a | 3 | 0.0 | a | 3 | 289.9 | a–d | 3 | 1.527 | a–c | 3 | 0.42 | b | 3 | 1.83 | b–c |
| 1+4 | 3 | 0.0 | a | 3 | 0.0 | a | 3 | 278.3 | a–e | 3 | 1.528 | a–c | 3 | 0.00 | b | 3 | 1.08 | c–d |
| 1+8 | 3 | 0.0 | a | 3 | 0.0 | a | 3 | 236.2 | d–e | 3 | 1.747 | a–b | 3 | 0.00 | b | 3 | 0.33 | c–d |
| 3+2 | 3 | 0.0 | a | 3 | 0.0 | a | 3 | 316.3 | a | 3 | 1.473 | b–c | 3 | 0.00 | b | 3 | 0.83 | c–d |
| 3+4 | 3 | 8.3 | a | 3 | 0.0 | a | 3 | 272.9 | a–e | 2 | 1.482 | b–c | 3 | 0.00 | b | 3 | 0.72 | c–d |
| 3+8 | 3 | 8.3 | a | 3 | 0.0 | a | 3 | 224.6 | e | 2 | 1.821 | a | 3 | 0.00 | b | 3 | 0.00 | d |
| 5+2 | 3 | 0.0 | a | 3 | 0.0 | a | 3 | 293.7 | a–c | 3 | 1.477 | b–c | 3 | 0.00 | b | 3 | 0.58 | c–d |
| 5+4 | 3 | 0.0 | a | 3 | 0.0 | a | 3 | 274.4 | a–e | 3 | 1.568 | a–c | 3 | 0.00 | b | 3 | 0.50 | c–d |
| 5+8 | 3 | 0.0 | a | 3 | 0.0 | a | 3 | 234.9 | d–e | 3 | 1.722 | a–b | 3 | 0.00 | b | 3 | 0.00 | d |

EXPERIMENT NO. 51
Statistical Analyses of Percent Mortality, Weight Gain, Feed/Gain,
Intestinal and Cecal Lesion Scores of broiler cockerels inoculated with
*E. maxima* and *E. tenella*

| Treatment | | Mortality Mean | | | | | Wt. Gain | | | Feed/Gain | | | Lesion Scores | | | | |
|---|---|---|---|---|---|---|---|---|---|---|---|---|---|---|---|---|---|
| | | | | | | | | | | | | | Intestinal | | | Cecal | |
| PPM | # | Total % | | # | % DTC | | # | Mean | | # | Mean | | # | Mean | | # | Mean |
| NC | | | | | | | | | | | | | | | | | |
| 0 | 3 | 0.0 | b | 3 | 0.0 | b | 3 | 345.9 | a | 3 | 1.375 | c | 3 | 0.00 | d | 3 | 0.00 | e |
| IC | | | | | | | | | | | | | | | | | | |
| 0 | 3 | 25.0 | a–b | 3 | 16.7 | b | 3 | 245.9 | a | | | | 3 | 7.64 | a | 3 | 3.67 | a |
| A82810 | | | | | | | | | | | | | | | | | | |
| 1 | 3 | 41.7 | a | 3 | 41.7 | a | 3 | 259.3 | a | | | | 3 | 8.67 | a | 3 | 3.67 | a |
| 3 | 3 | 8.3 | b | 3 | 8.3 | b | 3 | 281.8 | a | 2 | 1.482 | b–c | 3 | 7.00 | a | 3 | 2.58 | b–c |
| 5 | 3 | 0.0 | b | 3 | 0.0 | b | 3 | 270.3 | a | 3 | 1.554 | b–c | 3 | 8.25 | a | 3 | 2.42 | c |
| Example No. 113 | | | | | | | | | | | | | | | | | | |
| 2 | 3 | 0.0 | b | 3 | 0.0 | b | 3 | 190.8 | a | 3 | 1.956 | a | 3 | 7.75 | a | 3 | 3.33 | a–b |
| 4 | 3 | 16.7 | b | 3 | 16.7 | b | 3 | 232.8 | a | 2 | 1.848 | a–b | 3 | 4.08 | b | 3 | 3.67 | a |
| 8 | 3 | 0.0 | b | 3 | 0.0 | b | 3 | 234.1 | a | 3 | 1.786 | a–b | 3 | 0.67 | d | 3 | 1.00 | d–e |
| A82810 + Example No. 113 | | | | | | | | | | | | | | | | | | |
| 1+2 | 3 | 0.0 | b | 3 | 0.0 | b | 3 | 262.0 | a | 3 | 1.674 | a–c | 3 | 3.08 | b–c | 3 | 2.83 | a–c |
| 1+4 | 3 | 8.3 | b | 3 | 0.0 | b | 3 | 281.6 | a | 2 | 1.569 | b–c | 3 | 2.00 | b–d | 3 | 2.39 | c |
| 1+8 | 3 | 0.0 | b | 3 | 0.0 | b | 3 | 233.4 | a | 3 | 1.741 | a–b | 3 | 0.33 | d | 3 | 0.83 | d–e |
| 3+2 | 3 | 0.0 | b | 3 | 0.0 | b | 3 | 313.3 | a | 3 | 1.509 | b–c | 3 | 1.33 | c–d | 3 | 1.08 | d |
| 3+4 | 3 | 0.0 | b | 3 | 0.0 | b | 3 | 300.0 | a | 3 | 1.538 | b–c | 3 | 0.00 | d | 3 | 0.58 | d–e |
| 3+8 | 3 | 0.0 | b | 3 | 0.0 | b | 3 | 251.7 | a | 3 | 1.733 | a–b | 3 | 0.00 | d | 3 | 0.08 | e |
| 5+2 | 3 | 0.0 | b | 3 | 0.0 | b | 3 | 303.4 | a | 3 | 1.478 | b–c | 3 | 0.00 | d | 3 | 0.25 | d–e |
| 5+4 | 3 | 0.0 | b | 3 | 0.0 | b | 3 | 295.4 | a | 3 | 1.541 | b–c | 3 | 0.00 | d | 3 | 0.17 | d–e |
| 5+8 | 3 | 0.0 | b | 3 | 0.0 | b | 3 | 279.8 | a | 3 | 1.664 | a–c | 3 | 0.00 | d | 3 | 0.00 | e |

EXPERIMENT NO. 52
Statistical Analyses of Percent Mortality, Weight Gain, Feed/Gain,
Intestinal and Cecal Lesion Scores of broiler cockerels inoculated with
*E. acervulina* and *E. tenella*

| Treatment | | Mortality Mean | | | | Wt. Gain | | Feed/Gain | | Lesion Scores Intestinal | | Cecal | |
|---|---|---|---|---|---|---|---|---|---|---|---|---|---|
| PPM | # | Total % | | # | % DTC | # | Mean | # | Mean | # | Mean | # | Mean |
| NC | | | | | | | | | | | | | |
| 0 | 3 | 0.0 | a | 3 | 0.0 | a | 3 330.2 a | 3 | 1.346 d | 3 | 0.00 c | 3 | 0.00 c |
| IC | | | | | | | | | | | | | |
| 0 | 3 | 0.0 | a | 3 | 0.0 | a | 3 240.8 c–d | 3 | 1.682 b–d | 3 | 7.92 a | 3 | 3.58 a |
| A204 | | | | | | | | | | | | | |
| 2 | 3 | 8.3 | a | 3 | 8.3 | a | 3 247.4 c–d | 2 | 1.695 b–d | 3 | 7.17 a | 3 | 3.33 a–b |
| 4 | 3 | 0.0 | a | 3 | 0.0 | a | 3 248.1 c–d | 3 | 1.707 b–d | 3 | 4.58 b | 3 | 2.83 a–b |
| 8 | 3 | 0.0 | a | 3 | 0.0 | a | 3 289.4 a–c | 3 | 1.530 c–d | 3 | 0.92 c | 3 | 3.17 a–b |
| Example No. 113 | | | | | | | | | | | | | |
| 2 | 3 | 0.0 | a | 3 | 0.0 | a | 3 228.5 d | 3 | 1.800 b–c | 3 | 5.00 b | 3 | 3.33 a–b |
| 4 | 3 | 0.0 | a | 3 | 0.0 | a | 3 260.6 b–d | 3 | 1.747 b–c | 3 | 0.00 c | 3 | 2.17 b |
| 8 | 3 | 8.3 | a | 3 | 0.0 | a | 3 165.9 e | 2 | 2.232 a | 3 | 0.00 c | 3 | 0.67 c |
| A204 + Example No. 113 | | | | | | | | | | | | | |
| 2+2 | 3 | 0.0 | a | 3 | 0.0 | a | 3 285.7 a–c | 3 | 1.557 c–d | 3 | 0.25 c | 3 | 2.92 a–b |
| 2+4 | 3 | 0.0 | a | 3 | 0.0 | a | 3 281.1 b–d | 3 | 1.634 b–d | 3 | 0.00 c | 3 | 0.75 c |
| 2+8 | 3 | 16.7 | a | 3 | 0.0 | a | 3 190.0 e | 2 | 2.060 a–b | 3 | 0.00 c | 3 | 0.50 c |
| 4+2 | 3 | 8.3 | a | 3 | 0.0 | a | 3 270.2 b–d | 2 | 1.604 b–d | 3 | 0.00 c | 3 | 2.08 b |
| 4+4 | 3 | 0.0 | a | 3 | 0.0 | a | 3 258.9 b–d | 3 | 1.669 b–d | 3 | 0.00 c | 3 | 0.75 c |
| 4+8 | 3 | 16.7 | a | 3 | 0.0 | a | 3 185.4 e | 2 | 2.164 a | 3 | 0.00 c | 3 | 0.00 c |
| 8+2 | 3 | 8.3 | a | 3 | 0.0 | a | 3 306.2 a–b | 2 | 1.546 c–d | 3 | 0.00 c | 3 | 0.67 c |
| 8+4 | 3 | 0.0 | a | 3 | 0.0 | a | 3 272.4 b–d | 3 | 1.672 b–d | 3 | 0.00 c | 3 | 0.33 c |
| 8+8 | 3 | 16.7 | a | 3 | 0.0 | a | 3 177.0 e | 1 | 2.424 a | 3 | 0.00 c | 3 | 0.00 c |

EXPERIMENT NO. 53
Statistical Analyses of Percent Mortality, Weight Gain, Feed/Gain,
Intestinal and Cecal Lesion Scores of broiler cockerels inoculated with
*E. acervulina*, *E. maxima* and *E. tenella*

| Treatment | | Mortality Mean | | | | Wt. Gain | | Feed/Gain | | Lesion Scores Intestinal | | Cecal | |
|---|---|---|---|---|---|---|---|---|---|---|---|---|---|
| PPM | # | Total % | | # | % DTC | # | Mean | # | Mean | # | Mean | # | Mean |
| NC | | | | | | | | | | | | | |
| 0 | 4 | 0.0 | a | 4 | 0.0 | a | 4 325.9 a | 4 | 1.423 c–d | 4 | 0.00 c | 4 | 0.00 f |
| IC | | | | | | | | | | | | | |
| 0 | 4 | 0.0 | a | 4 | 0.0 | a | 4 254.8 c–e | 4 | 1.666 a–c | 4 | 8.81 a | 4 | 3.31 c |
| A80190 | | | | | | | | | | | | | |
| 30 | 4 | 0.0 | a | 4 | 0.0 | a | 4 313.5 a–b | 4 | 1.428 c–d | 4 | 0.00 c | 4 | 0.44 e |
| 40 | 4 | 0.0 | a | 4 | 0.0 | a | 4 317.3 a | 4 | 1.392 d | 4 | 0.00 c | 4 | 0.00 f |
| 50 | 4 | 0.0 | a | 4 | 0.0 | a | 4 309.2 a–b | 4 | 1.462 c–d | 4 | 0.00 c | 4 | 0.00 f |
| Example No. 57 | | | | | | | | | | | | | |
| 2 | 4 | 0.0 | a | 4 | 0.0 | a | 4 221.9 e | 4 | 1.809 a | 4 | 8.50 b | 4 | 3.56 b |
| 3 | 4 | 0.0 | a | 4 | 0.0 | a | 4 232.4 d–e | 4 | 1.730 a–b | 4 | 8.69 a–b | 4 | 3.06 d |
| 4 | 4 | 0.0 | a | 4 | 0.0 | a | 4 222.9 e | 4 | 1.880 a | 4 | 8.88 a | 4 | 3.81 a |
| A80190 + Example No. 57 | | | | | | | | | | | | | |
| 30+2 | 4 | 6.3 | a | 4 | 0.0 | a | 4 307.5 a–b | 4 | 1.520 b–d | 4 | 0.00 c | 4 | 0.00 f |
| 30+3 | 4 | 0.0 | a | 4 | 0.0 | a | 4 292.4 a–c | 4 | 1.533 b–d | 4 | 0.00 c | 4 | 0.00 f |
| 30+4 | 4 | 0.0 | a | 4 | 0.0 | a | 4 306.8 a–b | 4 | 1.472 c–d | 4 | 0.00 c | 4 | 0.00 f |
| 40+2 | 4 | 0.0 | a | 4 | 0.0 | a | 4 285.4 a–c | 4 | 1.468 c–d | 4 | 0.00 c | 4 | 0.00 f |
| 40+3 | 4 | 0.0 | a | 4 | 0.0 | a | 4 298.0 a–c | 4 | 1.498 b–d | 4 | 0.00 c | 4 | 0.00 f |
| 40+4 | 4 | 0.0 | a | 4 | 0.0 | a | 4 287.3 a–c | 4 | 1.538 b–d | 4 | 0.00 c | 4 | 0.00 f |
| 50+2 | 4 | 6.3 | a | 5 | 0.0 | a | 4 299.4 a–c | 4 | 1.524 b–d | 4 | 0.00 c | 4 | 0.00 f |
| 50+3 | 4 | 0.0 | a | 4 | 0.0 | a | 4 255.1 c–e | 4 | 1.781 a | 4 | 0.00 c | 4 | 0.00 f |
| 50+4 | 4 | 0.0 | a | 4 | 0.0 | a | 4 267.0 b–d | 4 | 1.672 a–c | 4 | 0.00 c | 4 | 0.00 f |

EXPERIMENT NO. 54
Statistical Analyses of Percent Mortality, Weight Gain, Feed/Gain,
Intestinal and Cecal Lesion Scores of broiler cockerels inoculated with
*E. acervulina, E. maxima* and *E. tenella*

| Treatment | | Mortality Mean | | | | Wt. Gain | | Feed/Gain | | Intestinal Lesion | | Cecal Lesion | |
|---|---|---|---|---|---|---|---|---|---|---|---|---|---|
| PPM | # | Total % | | # | % DTC | # | Mean | # | Mean | # | Mean | # | Mean |
| NC | | | | | | | | | | | | | |
| 0 | 4 | 0.0 | a | 4 | 0.0 a | 4 | 322.3 a | 4 | 1.356 e | 4 | 0.00 e | 4 | 0.38 d |
| IC | | | | | | | | | | | | | |
| 0 | 4 | 18.8 | a | 4 | 18.8 a | 4 | 203.6 c | 4 | 1.865 b–d | 4 | 8.44 a | 4 | 3.44 a |
| A80190 | | | | | | | | | | | | | |
| 30 | 4 | 6.3 | a | 4 | 0.0 a | 4 | 259.4 b | 4 | 1.624 c–e | 4 | 6.90 a–b | 4 | 3.54 a |
| 40 | 4 | 0.0 | a | 4 | 0.0 a | 4 | 229.6 b–c | 4 | 1.670 b–e | 4 | 5.13 b–c | 4 | 2.81 a–b |
| 50 | 4 | 0.0 | a | 4 | 0.0 a | 4 | 285.5 a–b | 4 | 1.449 e | 4 | 1.94 d–e | 4 | 2.00 b–c |
| Example No. 57 | | | | | | | | | | | | | |
| 2 | 4 | 6.3 | a | 4 | 6.3 a | 4 | 186.4 c–d | 4 | 1.955 b | 4 | 8.81 a | 4 | 3.56 a |
| 3 | 4 | 12.5 | a | 4 | 12.5 a | 4 | 203.0 c | 4 | 1.885 b–c | 4 | 8.31 a | 4 | 3.75 a |
| 4 | 4 | 6.3 | a | 5 | 6.3 a | 4 | 151.9 d | 4 | 2.285 a | 4 | 8.81 a | 4 | 3.88 a |
| A80190 + Example No. 57 | | | | | | | | | | | | | |
| 30+2 | 4 | 0.0 | a | 4 | 0.0 a | 4 | 260.5 b | 4 | 1.589 c–e | 4 | 3.75 c–d | 4 | 3.56 a |
| 30+3 | 4 | 6.3 | a | 4 | 0.0 a | 4 | 270.8 a–b | 4 | 1.490 d–e | 4 | 3.08 c–e | 4 | 3.19 a–b |
| 30+4 | 4 | 0.0 | a | 4 | 0.0 a | 4 | 274.6 a–b | 4 | 1.495 d–e | 4 | 0.81 e | 4 | 2.00 b–c |
| 40+2 | 4 | 6.3 | a | 4 | 6.3 a | 4 | 256.9 b | 4 | 1.549 c–e | 4 | 3.81 c–d | 4 | 2.75 a–b |
| 40+3 | 4 | 0.0 | a | 4 | 0.0 a | 4 | 290.2 a–b | 4 | 1.486 d–e | 4 | 0.94 e | 4 | 1.50 c–d |
| 40+4 | 4 | 0.0 | a | 4 | 0.0 a | 4 | 276.8 a–b | 4 | 1.554 c–e | 4 | 0.31 e | 4 | 1.44 c–d |
| 50+2 | 4 | 0.0 | a | 4 | 0.0 a | 4 | 287.8 a–b | 4 | 1.486 d–e | 4 | 0.13 e | 4 | 1.31 c–d |
| 50+3 | 4 | 0.0 | a | 4 | 0.0 a | 4 | 271.2 a–b | 4 | 1.615 c–e | 4 | 0.13 e | 4 | 0.88 c–d |
| 50+4 | 4 | 0.0 | a | 4 | 0.0 a | 4 | 263.4 b | 4 | 1.566 c–e | 4 | 0.50 e | 4 | 0.63 d |

EXPERIMENT NO. 55
Statistical Analyses of Percent Mortality, Weight Gain, Feed/Gain,
Intestinal and Cecal Lesion Scores of broiler cockerels inoculated with
*E. tenella, E. acervulina* and *E. maxima*

| Treatment | | Mortality Mean | | | | Wt. Gain | | Feed/Gain | | Intestinal Lesion | | Cecal Lesion | |
|---|---|---|---|---|---|---|---|---|---|---|---|---|---|
| PPM | # | Total % | | # | % DTC | # | Mean | # | Mean | # | Mean | # | Mean |
| NC | | | | | | | | | | | | | |
| 0 | 3 | 0.0 | b | 3 | 0.0 b | 3 | 218.8 a | 3 | 1.285 d | 3 | 0.00 b | 3 | 0.00 d |
| IC | | | | | | | | | | | | | |
| 0 | 3 | 40.0 | a–b | 3 | 40.0 a | 3 | 105.2 c | | | 3 | 1.50 a | 3 | 3.44 a |
| Example No. 22 | | | | | | | | | | | | | |
| 15 | 3 | 86.7 | a | 3 | 0.0 b | 1 | 5.9 e | | | 1 | 0.00 b | 1 | 0.00 d |
| 10 | 3 | 53.3 | a–b | 3 | 0.0 b | 2 | 84.4 c–d | 1 | 2.352 a | 2 | 0.00 b | 2 | 0.00 d |
| 5 | 3 | 13.3 | b | 3 | 0.0 b | 3 | 144.6 b | 1 | 1.675 b–c | 3 | 0.08 b | 3 | 2.05 b |
| Example No. 15 | | | | | | | | | | | | | |
| 15 | 3 | 6.7 | b | 3 | 0.0 b | 3 | 146.4 b | 2 | 1.811 b | 3 | 0.00 b | 3 | 1.77 b–c |
| 10 | 3 | 0.0 | b | 3 | 0.0 b | 3 | 160.1 b | 3 | 1.588 c | 3 | 0.00 b | 3 | 3.27 a |
| 5 | 3 | 26.7 | b | 3 | 26.7 a–b | 3 | 132.3 b | 1 | 1.747 b | 3 | 0.00 b | 3 | 3.60 a |

EXPERIMENT NO. 56
Statistical Analyses of Percent Mortality, Weight Gain, Feed/Gain,
Intestinal and Cecal Lesion Scores of broiler cockerels inoculated with
*E. acervulina* and *E. tenella*

| Treatment | | Mortality Mean | | | | Wt. Gain | | Feed/Gain | | Lesion Scores | | | |
|---|---|---|---|---|---|---|---|---|---|---|---|---|---|
| | | | | | | | | | | Intestinal | | Cecal | |
| PPM | # | Total % | | # | % DTC | # | Mean | # | Mean | # | Mean | # | Mean |
| NC | | | | | | | | | | | | | |
| 0 | 3 | 8.3 | b | 3 | 0.0 a | 3 | 323.0 a | 2 | 1.396 d | 3 | 0.00 c | 3 | 0.22 c |
| IC | | | | | | | | | | | | | |
| 0 | 3 | 16.7 | b | 3 | 16.7 a | 3 | 195.7 e | 2 | 2.032 a | 3 | 7.67 a | 3 | 3.75 a |
| A82810 | | | | | | | | | | | | | |
| 1 | 3 | 8.3 | b | 3 | 8.3 a | 3 | 202.0 e | 2 | 2.032 a | 3 | 7.42 a | 3 | 3.50 a |
| 3 | 3 | 0.0 | b | 3 | 0.0 a | 3 | 278.3 a–d | 3 | 1.565 b–d | 3 | 2.33 b | 3 | 3.00 a |
| 5 | 3 | 0.0 | b | 3 | 0.0 a | 3 | 317.3 a | 3 | 1.448 c–d | 3 | 0.50 c | 3 | 1.50 b |
| Example No. 36 | | | | | | | | | | | | | |
| 6 | 3 | 33.3 | a | 3 | 25.0 a | 3 | 211.6 e | | | 3 | 7.08 a | 3 | 3.69 a |
| 12 | 3 | 0.0 | b | 3 | 0.0 a | 3 | 256.2 c–d | 3 | 1.701 b | 3 | 0.58 c | 3 | 3.58 a |
| 24 | 3 | 0.0 | b | 3 | 0.0 a | 3 | 232.1 d–e | 3 | 1.832 a | 3 | 0.00 c | 3 | 1.42 b |
| A82810 + Example 36 | | | | | | | | | | | | | |
| 1+6 | 3 | 0.0 | b | 3 | 0.0 a | 3 | 268.7 b–d | 3 | 1.533 b–d | 3 | 0.17 c | 3 | 2.92 a |
| 1+12 | 3 | 0.0 | b | 3 | 0.0 a | 3 | 270.8 b–d | 3 | 1.609 b–d | 3 | 0.00 c | 3 | 0.75 b–c |
| 1+24 | 3 | 0.0 | b | 3 | 0.0 a | 3 | 212.1 e | 3 | 1.902 a | 3 | 0.00 c | 3 | 1.08 b–c |
| 3+6 | 3 | 0.0 | b | 3 | 0.0 a | 3 | 311.0 a–b | 3 | 1.478 c–d | 3 | 0.00 c | 3 | 0.92 b–c |
| 3+12 | 3 | 0.0 | b | 3 | 0.0 a | 3 | 278.8 a–d | 3 | 1.581 b–d | 3 | 0.00 c | 3 | 0.17 c |
| 3+24 | 3 | 0.0 | b | 3 | 0.0 a | 3 | 214.1 e | 3 | 1.954 a | 3 | 0.00 c | 3 | 0.17 c |
| 5+6 | 3 | 0.0 | b | 3 | 0.0 a | 3 | 290.9 a–c | 3 | 1.501 c–d | 3 | 0.00 c | 3 | 0.17 c |
| 5+12 | 3 | 0.0 | b | 3 | 0.0 a | 3 | 269.5 b–d | 3 | 1.620 b–c | 3 | 0.00 c | 3 | 0.25 c |
| 5+24 | 3 | 8.3 | b | 3 | 0.0 a | 3 | 205.8 e | 2 | 1.974 a | 3 | 0.00 c | 3 | 0.19 c |

EXPERIMENT NO. 57
Statistical Analyses of Percent Mortality, Weight Gain, Feed/Gain,
Intestinal and Cecal Lesion Scores of broiler cockerels inoculated with
*E. acervulina*, *E. maxima* and *E. tenella*

| Treatment | | Mortality Mean | | | | Wt. Gain | | Feed/Gain | | Lesion Scores | | | |
|---|---|---|---|---|---|---|---|---|---|---|---|---|---|
| | | | | | | | | | | Intestinal | | Cecal | |
| PPM | # | Total % | | # | % DTC | # | Mean | # | Mean | # | Mean | # | Mean |
| NC | | | | | | | | | | | | | |
| 0 | 4 | 0.0 | d | 4 | 0.0 a | 4 | 224.4 a | 4 | 1.655 f | 4 | 0.00 b | 4 | 0.00 f |
| IC | | | | | | | | | | | | | |
| 0 | 4 | 15.0 | d | 4 | 5.0 a | 4 | 117.2 d–f | 1 | 2.602 c | 4 | 6.43 a | 4 | 3.17 a–b |
| Example No. 94 | | | | | | | | | | | | | |
| 20 | 4 | 95.0 | a | 4 | 0.0 a | 1 | 108.4 d–f | | | 1 | 0.00 b | 1 | 0.00 f |
| 15 | 4 | 20.0 | c–d | 4 | 0.0 a | 4 | 106.0 e–f | 1 | 3.461 a | 4 | 0.00 b | 4 | 0.31 e–f |
| 12.5 | 4 | 0.0 | d | 4 | 0.0 a | 4 | 127.4 d–f | 4 | 2.543 c | 4 | 0.00 b | 4 | 0.25 e–f |
| 10 | 4 | 10.0 | d | 4 | 0.0 a | 4 | 147.8 c–f | 3 | 2.023 e | 4 | 0.00 b | 4 | 1.63 c–e |
| 5 | 4 | 5.0 | d | 4 | 5.0 a | 4 | 199.2 a–b | 3 | 1.917 e | 4 | 0.00 b | 4 | 2.16 c–d |
| Example No. 98 | | | | | | | | | | | | | |
| 20 | 4 | 90.0 | a | 4 | 0.0 a | 2 | 14.9 g | | | 2 | 0.00 b | 2 | 1.00 d–f |
| 15 | 4 | 55.0 | b | 4 | 0.0 a | 4 | 94.6 f | | | 4 | 0.00 b | 4 | 0.38 3–f |
| 12.5 | 4 | 35.0 | c | 4 | 0.0 a | 4 | 101.9 e–f | | | 4 | 0.00 b | 4 | 0.90 d–f |
| 10 | 4 | 0.0 | d | 4 | 0.0 a | 4 | 142.4 c–f | 4 | 2.260 d | 4 | 0.00 b | 4 | 1.30 d–f |
| 5 | 4 | 0.0 | d | 4 | 0.0 a | 4 | 183.1 b–c | 4 | 1.854 e | 4 | 0.00 b | 4 | 2.35 b–c |
| NC (Equal volume of ACETONE added) | | | | | | | | | | | | | |
| 0 | 2 | 0.0 | d | 2 | 0.0 a | 2 | 235.5 a | 2 | 1.521 f | 2 | 0.00 b | 2 | 0.00 f |
| IC (Equal volume of ACETONE added) | | | | | | | | | | | | | |
| 0 | 2 | 10.0 | d | 2 | 10.0 a | 2 | 101.1 e–f | 1 | 2.931 b | 2 | 6.25 a | 2 | 3.80 a |
| Example No. 94 (Dissolved in ACETONE) | | | | | | | | | | | | | |
| 20 | 2 | 100.0 | a | 2 | 0.0 a | | | | | | | | |
| 15 | 2 | 40.0 | b–c | 2 | 0.0 a | 2 | 94.4 f | | | 2 | 0.00 b | 2 | 0.50 e–f |

-continued

| | | | | | | | | | | | | | | | | |
|---|---|---|---|---|---|---|---|---|---|---|---|---|---|---|---|---|
| 10 | 2 | 0.0 | d | 2 | 0.0 | a | 2 | 166.5 | b–e | 2 | 2.003 | e | 2 | 0.00 | b | 2 | 1.30 | d–f |
| 5 | 2 | 0.0 | d | 2 | 0.0 | a | 2 | 169.5 | b–d | 2 | 1.986 | e | 2 | 0.60 | b | 2 | 2.20 | b–d |

EXPERIMENT NO. 58
Statistical Analyses of Percent Mortality, Weight Gain, Feed/Gain,
Intestinal and Cecal Lesion Scores of broiler cockerels inoculated with
*E. acervulina* and *E. tenella*

| Treatment | Mortality Mean | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 3 | 0.0 a | 3 | 0.0 a | 3 | 322.8 a | 3 | 1.448 c | 3 | 0.00 b | 3 | 0.00 e |
| IC | | | | | | | | | | | | |
| 0 | 3 | 0.0 a | 3 | 0.0 a | 3 | 256.0 b–c | 3 | 1.691 a–c | 3 | 7.42 a | 3 | 2.92 a |
| A204 | | | | | | | | | | | | |
| 2 | 3 | 8.3 a | 3 | 0.0 a | 3 | 263.9 b–c | 2 | 1.744 a–b | 3 | 8.00 a | 3 | 3.25 a |
| 4 | 3 | 8.3 a | 3 | 0.0 a | 3 | 237.1 c | 2 | 1.840 a | 3 | 1.81 b | 3 | 3.03 a |
| 8 | 3 | 8.3 a | 3 | 0.0 a | 3 | 242.9 c | 2 | 1.707 a–c | 3 | 0.00 b | 3 | 2.22 a–c |
| Example No. 108 | | | | | | | | | | | | |
| 2 | 3 | 0.0 a | 3 | 0.0 a | 3 | 237.3 c | 3 | 1.831 a | 3 | 7.75 a | 3 | 3.17 a |
| 4 | 3 | 8.3 a | 3 | 0.0 a | 3 | 237.1 c | 2 | 1.840 a | 3 | 1.81 b | 3 | 3.03 a |
| 8 | 3 | 8.3 a | 3 | 0.0 a | 3 | 242.9 c | 2 | 1.707 a–c | 3 | 0.00 b | 3 | 2.22 a–c |
| A204 + Example No. 108 | | | | | | | | | | | | |
| 2+2 | 3 | 0.0 a | 3 | 0.0 a | 3 | 271.4 b–c | 3 | 1.579 a–c | 3 | 0.92 b | 3 | 3.08 a |
| 2+4 | 3 | 0.0 a | 3 | 0.0 a | 3 | 282.9 a–c | 3 | 1.592 a–c | 3 | 0.00 b | 3 | 2.58 a–b |
| 2+8 | 3 | 0.0 a | 3 | 0.0 a | 3 | 264.3 b–c | 3 | 1.644 a–c | 3 | 0.00 b | 3 | 1.17 c–e |
| 4+2 | 3 | 0.0 a | 3 | 0.0 a | 3 | 305.7 a–b | 3 | 1.509 b–c | 3 | 0.00 b | 3 | 2.42 a–b |
| 4+4 | 3 | 8.3 a | 3 | 0.0 a | 3 | 271.3 b–c | 2 | 1.637 a–c | 3 | 0.00 b | 3 | 1.44 b–d |
| 4+8 | 3 | 0.0 a | 3 | 0.0 a | 3 | 251.8 b–c | 3 | 1.670 a–c | 3 | 0.00 b | 3 | 0.33 d–e |
| 8+2 | 3 | 0.0 a | 3 | 0.0 a | 3 | 290.0 a–c | 3 | 1.448 c | 3 | 0.00 b | 3 | 1.83 a–c |
| 8+4 | 3 | 0.0 a | 3 | 0.0 a | 3 | 269.0 b–c | 3 | 1.508 b–c | 3 | 0.00 b | 3 | 0.50 d–e |
| 8+8 | 3 | 8.3 a | 3 | 0.0 a | 3 | 251.2 b–c | 2 | 1.708 a–c | 3 | 0.00 b | 3 | 0.00 e |

EXPERIMENT NO. 59
Statistical Analyses of Percent Mortality, Weight Gain, Feed/Gain,
Intestinal and Cecal Lesion Scores of broiler cockerels inoculated with
*E. tenella* and *E. acervulina*

| Treatment | Mortality Mean(3) | | | | Wt. Gain(4) | | Feed/Gain(5) | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 4 | 0.0 e | 4 | 0.0 e | 4 | 315.6 a | 4 | 1.457 c–d | 4 | 0.00 g | 4 | 0.00 d |
| IC | | | | | | | | | | | | |
| 0 | 4 | 0.0 e | 4 | 0.0 e | 4 | 242.1 b–d | 4 | 1.736 a–d | 4 | 5.50 a–b | 4 | 3.63 a |
| MADURAMICIN | | | | | | | | | | | | |
| 2 | 4 | 6.3 a–d | 4 | 0.0 e | 4 | 267.2 a–c | 4 | 1.601 c–d | 4 | 5.00 a–c | 4 | 3.48 a |
| 3 | 4 | 0.0 e | 4 | 0.0 e | 4 | 265.0 a–c | 4 | 1.639 b–d | 4 | 4.06 b–d | 4 | 3.50 a |
| 4 | 4 | 0.0 e | 4 | 0.0 e | 4 | 298.7 a | 4 | 1.464 c–d | 4 | 4.31 a–d | 4 | 3.63 a |
| 5 | 4 | 0.0 e | 4 | 0.0 e | 4 | 291.7 a–b | 4 | 1.544 c–d | 4 | 4.19 a–d | 4 | 3.56 a |
| Example No. 57 | | | | | | | | | | | | |
| 2 | 4 | 6.3 a–d | 4 | 6.3 b | 4 | 209.0 d | 4 | 1.893 a | 4 | 6.19 a | 4 | 3.81 a |
| 3 | 4 | 0.0 e | 4 | 0.0 e | 4 | 229.2 c–d | 4 | 1.763 a–c | 4 | 5.75 a–b | 4 | 3.38 a |
| 4 | 4 | 12.5 a | 4 | 12.5 a | 4 | 217.1 d | 4 | 1.848 a–b | 4 | 6.00 a–b | 4 | 3.63 a |
| 5 | 4 | 0.0 e | 4 | 0.0 e | 4 | 233.1 c–d | 4 | 1.869 a–b | 4 | 4.31 a–d | 4 | 3.69 a |
| MADURAMICIN + Example No. 57 | | | | | | | | | | | | |
| 2+2 | 4 | 0.0 e | 4 | 0.0 e | 4 | 281.3 a–b | 4 | 1.544 c–d | 4 | 3.31 c–e | 4 | 3.56 a |
| 2+3 | 4 | 0.0 e | 4 | 0.0 e | 4 | 290.3 a–b | 4 | 1.483 c–d | 4 | 2.50 d–f | 4 | 3.81 a |
| 2+4 | 4 | 0.0 e | 4 | 0.0 e | 4 | 289.4 a–b | 4 | 1.483 c–d | 4 | 1.63 e–g | 4 | 3.56 a |
| 2+5 | 4 | 6.3 a–d | 4 | 0.0 e | 4 | 282.5 a–b | 4 | 1.567 c–d | 4 | 0.77 f–g | 4 | 2.48 a–b |
| 3+2 | 4 | 0.0 e | 4 | 0.0 e | 4 | 291.6 a–b | 4 | 1.591 c–d | 4 | 2.56 d–f | 4 | 3.50 a |
| 3+3 | 4 | 0.0 e | 4 | 0.0 e | 4 | 283.2 a–b | 4 | 1.495 c–d | 4 | 1.75 e–g | 4 | 3.50 a |

-continued

| | | | | | | | | | | | | | | | | |
|---|---|---|---|---|---|---|---|---|---|---|---|---|---|---|---|---|
| 3+4 | 4 | 0.0 | e | 4 | 0.0 | e | 4 | 296.4 | a | 4 | 1.506 | c–d | 4 | 1.81 | e–g | 4 | 2.44 | a–b |
| 3+5 | 4 | 0.0 | e | 4 | 0.0 | e | 4 | 278.4 | a–b | 4 | 1.544 | c–d | 4 | 1.38 | e–g | 4 | 2.19 | b |
| 4+2 | 4 | 0.0 | e | 4 | 0.0 | e | 4 | 302.2 | a | 4 | 1.448 | d | 4 | 1.50 | e–g | 4 | 3.31 | a |
| 4+3 | 4 | 0.0 | e | 4 | 0.0 | e | 4 | 289.5 | a–b | 4 | 1.538 | c–d | 4 | 2.13 | e–g | 4 | 3.50 | a |
| 4+4 | 4 | 0.0 | e | 4 | 0.0 | e | 4 | 283.9 | a–b | 4 | 1.573 | c–d | 4 | 0.44 | f–g | 4 | 2.06 | b |
| 4+5 | 4 | 0.0 | e | 4 | 0.0 | e | 4 | 295.0 | a | 3 | 1.509 | c–d | 4 | 0.69 | f–g | 4 | 1.44 | b–c |
| 5+2 | 4 | 0.0 | e | 4 | 0.0 | e | 4 | 276.4 | a–b | 4 | 1.537 | c–d | 4 | 1.81 | e–g | 4 | 2.50 | a–b |
| 5+3 | 4 | 0.0 | e | 4 | 0.0 | e | 4 | 299.0 | a | 4 | 1.476 | c–d | 4 | 0.94 | f–g | 4 | 2.50 | a–b |
| 5+4 | 4 | 0.0 | e | 4 | 0.0 | e | 4 | 293.2 | a–b | 4 | 1.484 | c–d | 4 | 0.50 | f–g | 4 | 1.38 | b–c |
| 5+5 | 4 | 0.0 | e | 4 | 0.0 | e | 4 | 287.4 | a–b | 4 | 1.575 | c–d | 4 | 0.19 | g | 4 | 1.00 | c |

EXPERIMENT NO. 60
Statistical Analyses of Percent Mortality, Weight Gain, Feed/Gain,
Intestinal and Cecal Lesion Scores of broiler cockerels inoculated with
*E. tenella* and *E. maxima*

| Treatment | Mortality Mean(3) | | | | Wt. Gain(4) | | Feed/Gain(5) | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC | | | | | | | | | | | | |
| 0 | 4 | 0.0 e | 4 | 0.0 e | 4 | 325.8 a | 4 | 1.453 f | 4 | 0.00 j | 4 | 0.00 h |
| IC | | | | | | | | | | | | |
| 0 | 4 | 25.0 a–c | 4 | 18.8 b–c | 4 | 154.5 g | 4 | 2.431 a | 4 | 8.42 a | 4 | 3.83 a |
| MADURAMICIN | | | | | | | | | | | | |
| 2 | 4 | 12.5 b–e | 4 | 12.5 b–e | 4 | 187.8 f–g | 4 | 2.155 b–c | 4 | 8.06 a–b | 4 | 3.69 a–b |
| 3 | 4 | 12.5 b–e | 4 | 12.5 b–e | 4 | 218.7 e–f | 4 | 1.892 c–e | 4 | 7.44 a–b | 4 | 3.75 a–b |
| 4 | 4 | 0.0 e | 4 | 0.0 e | 4 | 223.2 e–f | 4 | 1.799 d–f | 4 | 7.38 a–b | 4 | 3.63 a–c |
| 5 | 4 | 6.3 b–e | 4 | 0.0 e | 4 | 262.1 c–d | 4 | 1.600 e–f | 4 | 6.44 a–c | 4 | 3.88 a |
| Example No. 57 | | | | | | | | | | | | |
| 2 | 4 | 25.0 a–c | 4 | 25.0 a–b | 4 | 163.5 g | 4 | 2.303 a–b | 4 | 8.31 a–b | 4 | 3.88 a |
| 3 | 4 | 37.5 a | 4 | 27.5 a | 4 | 159.4 g | 4 | 2.496 a | 4 | 8.44 a | 4 | 3.94 a |
| 4 | 4 | 6.3 b–e | 4 | 6.3 b–e | 4 | 185.9 f–g | 4 | 2.091 b–d | 4 | 7.31 a–b | 4 | 3.88 a |
| 5 | 4 | 6.3 b–e | 4 | 6.3 b–e | 4 | 203.8 f | 4 | 2.007 c–d | 4 | 7.88 a–b | 4 | 3.50 a–c |
| MADURAMICIN + Example No. 57 | | | | | | | | | | | | |
| 2+2 | 4 | 12.5 b–e | 4 | 12.5 b–e | 4 | 248.7 d–e | 4 | 1.787 d–f | 4 | 6.63 a–c | 4 | 4.00 a |
| 2+3 | 4 | 0.0 e | 4 | 0.0 e | 4 | 297.8 a–c | 4 | 1.443 f | 4 | 5.81 b–d | 4 | 3.31 a–c |
| 2+4 | 4 | 0.0 e | 4 | 0.0 e | 4 | 295.5 a–d | 4 | 1.502 f | 4 | 4.81 c–e | 4 | 3.63 a–c |
| 2+5 | 4 | 0.0 e | 4 | 0.0 e | 4 | 277.6 a–d | 4 | 1.587 e–f | 4 | 3.00 e–h | 4 | 2.44 c–e |
| 3+2 | 4 | 0.0 e | 4 | 0.0 e | 4 | 273.4 b–d | 4 | 1.653 e–f | 4 | 6.38 a–c | 4 | 3.56 a–c |
| 3+3 | 4 | 0.0 e | 4 | 0.0 e | 4 | 290.9 a–d | 4 | 1.580 e–f | 4 | 4.25 c–g | 4 | 3.75 a–b |
| 3+4 | 4 | 0.0 e | 4 | 0.0 e | 4 | 302.0 a–c | 4 | 1.484 f | 4 | 3.69 d–g | 4 | 2.50 b–e |
| 3+5 | 4 | 6.3 b–e | 4 | 0.0 e | 4 | 285.0 a–d | 4 | 1.564 e–f | 4 | 2.06 g–j | 4 | 2.17 d–f |
| 4+2 | 4 | 0.0 e | 4 | 0.0 e | 4 | 291.4 a–d | 4 | 1.514 f | 4 | 4.44 c–g | 4 | 3.63 a–c |
| 4+3 | 4 | 0.0 e | 4 | 0.0 e | 4 | 305.7 a–c | 4 | 1.462 f | 4 | 3.69 d–g | 4 | 3.06 a–d |
| 4+4 | 4 | 0.0 e | 4 | 0.0 e | 4 | 301.6 a–c | 4 | 1.471 f | 4 | 2.25 f–j | 4 | 1.75 e–f |
| 4+5 | 4 | 6.3 b–e | 4 | 0.0 e | 4 | 299.1 a–c | 4 | 1.510 f | 4 | 0.90 h–j | 4 | 1.19 f–g |
| 5+2 | 4 | 6.3 b–e | 4 | 0.0 e | 4 | 313.7 a–c | 4 | 1.463 f | 4 | 4.60 c–f | 4 | 2.52 b–e |
| 5+3 | 4 | 0.0 e | 4 | 0.0 e | 4 | 315.5 a–b | 4 | 1.448 f | 4 | 2.56 e–j | 4 | 1.69 e–f |
| 5+4 | 4 | 0.0 e | 4 | 0.0 e | 4 | 302.4 a–c | 4 | 1.461 f | 4 | 1.00 h–j | 4 | 1.19 f–g |
| 5+5 | 4 | 0.0 e | 4 | 0.0 e | 4 | 284.6 a–d | 4 | 1.591 e–f | 4 | 0.31 i–j | 4 | 0.63 g–h |

EXPERIMENT NO. 61
Statistical Analyses of Percent Mortality, Weight Gain, Feed/Gain,
Intestinal and Cecal Lesion Scores of broiler cockerels inoculated with
*E. acervulina* and *E. tenella*

| Treatment | Mort.(3) | | Wt. Gain(4) | | Feed/Gain(5) | | Lesion Scores | | | |
|---|---|---|---|---|---|---|---|---|---|---|
| | | | | | | | Intestinal | | Cecal | |
| PPM | # | Mean | # | Mean | # | Mean | # | Mean | # | Mean |
| NNC | | | | | | | | | | |
| 0 | 3 | 0.0 a | 3 | 280.7 a | 2 | 1.452 b | 3 | 0.00 d | 3 | 0.00 e |
| IC | | | | | | | | | | |
| 0 | 3 | 0.0 a | 3 | 239.2 a–b | 3 | 1.691 a–b | 3 | 8.00 a | 3 | 2.92 a–b |
| A204 | | | | | | | | | | |
| 2 | 3 | 8.3 1 | 3 | 261.3 a–b | 2 | 1.662 a–b | 3 | 6.75 a | 3 | 3.08 a–b |

-continued

| | | | | | | | | | | | | | | |
|---|---|---|---|---|---|---|---|---|---|---|---|---|---|---|
| 4 | 3 | 0.0 | a | 3 | 235.1 | a–b | 3 | 1.621 | a–b | 3 | 5.00 | b | 3 | 3.42 | a |
| 8 | 3 | 0.0 | a | 3 | 253.1 | a–b | 2 | 1.456 | b | 3 | 1.00 | d | 3 | 2.00 | a–d |
| Example No. 22 | | | | | | | | | | | | | | | |
| 2 | 3 | 8.3 | a | 3 | 258.2 | a–b | 2 | 1.577 | a–b | 3 | 3.00 | c | 3 | 2.92 | a–b |
| 4 | 3 | 0.0 | a | 3 | 261.8 | a–b | 3 | 1.590 | a–b | 3 | 0.00 | d | 3 | 2.17 | a–c |
| 8 | 3 | 0.0 | a | 3 | 171.2 | c | 1 | 1.860 | a–b | 3 | 0.00 | d | 3 | 0.50 | d–e |
| A204 + Example No. 22 | | | | | | | | | | | | | | | |
| 2+2 | 3 | 0.0 | a | 3 | 279.2 | a | 1 | 1.518 | a–b | 3 | 0.28 | d | 3 | 2.81 | a–b |
| 2+4 | 3 | 0.0 | a | 3 | 253.2 | a–b | 3 | 1.577 | a–b | 3 | 0.00 | d | 3 | 0.83 | c–e |
| 2+8 | 3 | 0.0 | a | 3 | 169.2 | c | 2 | 1.798 | a–b | 3 | 0.00 | d | 3 | 0.25 | e |
| 4+2 | 3 | 0.0 | a | 3 | 289.3 | a | 3 | 1.459 | b | 3 | 0.08 | d | 3 | 2.25 | a–c |
| 4+4 | 3 | 0.0 | a | 3 | 256.3 | a–b | 2 | 1.558 | a–b | 3 | 0.00 | d | 3 | 1.58 | b–e |
| 4+8 | 3 | 0.0 | a | 3 | 217.2 | a–c | | | | 3 | 0.00 | d | 3 | 0.44 | d–e |
| 8+2 | 3 | 0.0 | a | 3 | 284.0 | a | 2 | 1.451 | b | 3 | 0.00 | d | 3 | 0.89 | c–e |
| 8+4 | 3 | 0.0 | a | 3 | 255.6 | a–b | 1 | 1.587 | a–b | 3 | 0.00 | d | 3 | 0.08 | e |
| 8+8 | 3 | 0.0 | a | 3 | 195.9 | b–c | 1 | 2.069 | a | 3 | 0.00 | d | 3 | 0.00 | e |

EXPERIMENT NO. 62
Statistical Analyses of Percent Mortality, Weight Gain, Feed/Gain,
Intestinal and Cecal Lesion Scores of broiler cockerels inoculated with
*E. acervulina* and *E. tenella*

| Treatment | Mort.(3) | | Wt. Gain(4) | | Feed/Gain(5) | | Lesion Scores | | | |
|---|---|---|---|---|---|---|---|---|---|---|
| | | | | | | | Intestinal | | Cecal | |
| PPM | # | Mean | # | % DTC | # | Mean | # | Mean | # | Mean |
| NNC | | | | | | | | | | |
| 0 | 3 | 0.0 | a | 3 | 320.1 | a | 3 | 1.454 | b | 3 | 0.00 | d | 3 | 0.00 | c |
| IC | | | | | | | | | | |
| 0 | 3 | 0.0 | a | 3 | 277.3 | c | 3 | 1.787 | a | 3 | 8.08 | a | 3 | 3.42 | a |
| A204 | | | | | | | | | | |
| 2 | 3 | 0.0 | a | 3 | 239.3 | b–c | 3 | 1.787 | a | 3 | 6.33 | b | 3 | 3.42 | a |
| 4 | 3 | 8.3 | a | 3 | 263.5 | a–c | 2 | 1.708 | a–b | 3 | 3.33 | c | 3 | 3.08 | a |
| 8 | 3 | 0.0 | a | 3 | 272.4 | a–c | 3 | 1.619 | a–b | 3 | 0.58 | d | 3 | 3.33 | a |
| Example No. 57 | | | | | | | | | | |
| 2 | 3 | 16.7 | a | 3 | 238.8 | b–c | 2 | 1.675 | a–b | 3 | 5.33 | b | 3 | 3.33 | a |
| 4 | 3 | 0.0 | a | 3 | 236.3 | b–c | 3 | 1.748 | a | 3 | 2.83 | c–d | 3 | 3.00 | a |
| 8 | 3 | 0.0 | a | 3 | 241.1 | b–c | 2 | 1.735 | a–b | 3 | 0.17 | d | 3 | 3.19 | a |
| A204 + Example No. 57 | | | | | | | | | | |
| 2+2 | 3 | 0.0 | a | 3 | 268.6 | a–c | 3 | 1.610 | a–b | 3 | 2.58 | c–d | 3 | 3.00 | a |
| 2+4 | 3 | 0.0 | a | 3 | 278.4 | a–c | 3 | 1.599 | a–b | 3 | 0.25 | d | 3 | 3.08 | a |
| 2+8 | 3 | 0.0 | a | 3 | 253.9 | a–c | 2 | 1.691 | a–b | 3 | 0.00 | d | 3 | 0.97 | b–c |
| 4+2 | 3 | 0.0 | a | 3 | 256.4 | a–c | 3 | 1.624 | a–b | 3 | 0.33 | d | 3 | 3.25 | a |
| 4+4 | 3 | 0.0 | a | 3 | 290.0 | a–c | 3 | 1.543 | a–b | 3 | 0.00 | d | 3 | 2.08 | a–b |
| 4+8 | 3 | 0.0 | a | 3 | 237.9 | b–c | 3 | 1.675 | a–b | 3 | 0.00 | d | 3 | 0.75 | b–c |
| 8+2 | 3 | 0.0 | a | 3 | 290.0 | a–c | 2 | 1.484 | b | 3 | 0.00 | d | 3 | 1.50 | b–c |
| 8+4 | 3 | 0.0 | a | 3 | 304.3 | a–b | 3 | 1.497 | a–b | 3 | 0.00 | d | 3 | 0.58 | c |
| 8+8 | 3 | 0.0 | a | 3 | 265.8 | a–c | 3 | 1.646 | a–b | 3 | 0.00 | d | 3 | 0.33 | c |

We claim:

1. A method of preventing or treating coccidiosis in a fowl which comprises administering to the fowl both a first substance and a second substance, said first substance being a polyether antibiotic and said second substance selected from compounds of the formula

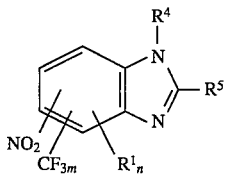

wherein $R^1$ represents bromo or chloro, m represents an integer of 0 or 1 and n represents an integer of from 0 to 3, with the sum of m and n being an integer of from 1 to 3;

$R^4$ represents H, OH, $OCH_3$, or a group hydrolyzable to a foregoing $R^4$ moiety; and $R^5$ represents difluoromethyl, chlorodifluoromethyl, 1, 1, 2,2-tetrafluoroethyl, or a perfluoroalkyl of $C_1$–$C_3$;

and the physiologically acceptable salts thereof; said first and second substance being administered in amounts which, together, are effective to prevent or treat coccidiosis in the fowl.

2. The method of claim 1 wherein the second substance is 1-hydroxy- 4-nitro-6-(trifluoromethyl)-2-(2,2,3,3-tetrafluoroethyl)benzimidazole or a physiologically acceptable salt thereof.

3. The method of claim 2 wherein the first substance is a polyether selected from the group consisting of antibiotic A204,
portmicin,
antibiotic A82810,
maduramicin, and
semduramicin.

4. The method of claim 3 wherein the polyether is portmicin.

5. The method of claim 3 wherein the polyether is antibiotic A82810.

6. The method of claim 1 where the coccidiosis is attributable to a polyether-insensitive strain of Eimeria.

7. The method of claim 6 wherein the second substance is 1-hydroxy- 4-nitro-6-(trifluoromethyl)-2-(2,2,3,3-tetrafluoroethyl)benzimidazole or a physiologically acceptable salt thereof.

8. The method of claim 7 wherein the polyether is selected from the group consisting of
antibiotic A204,
portmicin,
antibiotic A82810,
maduramicin, and
semduramicin.

9. The method of claim 8 wherein the polyether is portmicin.

10. The method of claim 8 wherein the polyether is antibiotic A82810.

* * * * *